(12) United States Patent
Failli et al.

(10) Patent No.: US 7,202,239 B2
(45) Date of Patent: Apr. 10, 2007

(54) CYCLOHEXYLPHENYL CARBOXAMIDES TOCOLYTIC OXYTOCIN RECEPTOR ANTAGONISTS

(75) Inventors: Amedeo Arturo Failli, Princeton Junction, NJ (US); Eugene John Trybulski, Princeton Junction, NJ (US); Jay Scott Shumsky, Hightstown, NJ (US); John Paul Dusza, Nanuet, NY (US); Kevin Anthony Memoli, Cranbury, NJ (US)

(73) Assignee: Wyeth, Madison, NJ (US)

( * ) Notice: Subject to any disclaimer, the term of this patent is extended or adjusted under 35 U.S.C. 154(b) by 615 days.

(21) Appl. No.: 10/119,994

(22) Filed: Apr. 10, 2002

(65) Prior Publication Data

US 2003/0027815 A1 Feb. 6, 2003

Related U.S. Application Data

(60) Provisional application No. 60/283,389, filed on Apr. 12, 2001.

(51) Int. Cl.
*A61P 15/06* (2006.01)
*A61K 31/55* (2006.01)
*C07D 487/12* (2006.01)

(52) U.S. Cl. ..................... 514/220; 540/561
(58) Field of Classification Search ............... 514/220; 540/561
See application file for complete search history.

(56) References Cited

U.S. PATENT DOCUMENTS

| | | | |
|---|---|---|---|
| 4,766,108 A | 8/1988 | Ali ..................... 514/16 |
| 5,055,448 A | 10/1991 | Manning et al. ............ 514/16 |
| 5,070,187 A | 12/1991 | Gavras et al. ............ 530/315 |
| 5,258,510 A | 11/1993 | Ogawa et al. ............ 540/476 |
| 5,436,333 A | 7/1995 | Venkatesan et al. ........ 540/586 |
| 5,459,131 A | 10/1995 | Albright et al. ............ 514/19 |
| 5,466,584 A | 11/1995 | Tanizawa et al. .......... 435/69.1 |
| 5,512,563 A | 4/1996 | Albright et al. ............ 514/217 |
| 5,516,774 A | 5/1996 | Albright et al. ............ 514/220 |
| 5,521,173 A | 5/1996 | Venkatesan et al. ........ 514/220 |
| 5,532,235 A | 7/1996 | Albright et al. ............ 514/215 |
| 5,536,718 A | 7/1996 | Albright et al. ............ 514/220 |
| 5,609,851 A | 3/1997 | Bennani ................. 424/9.454 |
| 5,654,297 A | 8/1997 | Albright et al. ............ 514/215 |
| 5,665,719 A | 9/1997 | Bock et al. ............. 514/227.8 |
| 5,670,509 A | 9/1997 | Evans et al. .............. 514/278 |
| 5,726,172 A | 3/1998 | Sparks et al. ............ 514/230.5 |
| 5,736,540 A | 4/1998 | Albright et al. ............ 514/220 |
| 5,753,644 A | 5/1998 | Ogawa et al. ............ 514/213 |
| 5,756,497 A | 5/1998 | Bell et al. ............... 514/230.5 |
| 5,756,504 A | 5/1998 | Bock et al. ................ 514/252 |
| 5,780,471 A | 7/1998 | Venkatesan et al. ........ 514/250 |
| 5,849,735 A | 12/1998 | Albright et al. ............ 514/220 |
| 5,880,122 A | 3/1999 | Trybulski et al. ............ 514/220 |
| 5,968,930 A | 10/1999 | Albright et al. ............ 514/220 |
| 6,268,359 B1 | 7/2001 | Ogawa et al. ............ 514/215 |
| 6,340,678 B1 | 1/2002 | Matushisa et al. ...... 514/213.01 |
| 2002/0183311 A1 | 12/2002 | Failli et al. ................ 514/220 |
| 2002/0198196 A1 | 12/2002 | Failli et al. ................ 514/220 |
| 2003/0004159 A1 | 1/2003 | Failli et al. ................ 514/220 |
| 2003/0008863 A1 | 1/2003 | Failli et al. ................ 514/220 |
| 2003/0018026 A1 | 1/2003 | Failli et al. ................ 514/220 |
| 2003/0055046 A1 | 3/2003 | Failli et al. ................ 514/220 |
| 2003/0055047 A1 | 3/2003 | Failli et al. ................ 514/220 |

FOREIGN PATENT DOCUMENTS

| | | |
|---|---|---|
| EP | 0 382 185 | 8/1990 |
| EP | 0 470 514 | 2/1992 |
| EP | 0 514 667 | 11/1992 |
| EP | 0 533 240 | 3/1993 |
| EP | 0 533 242 | 3/1993 |
| EP | 0 533 243 | 3/1993 |
| EP | 0 533 244 | 3/1993 |
| EP | 0 620 216 | 10/1994 |
| EP | 0 636 625 B1 | 1/1999 |
| GB | 2 326 410 | 12/1998 |
| GB | 2 326 639 | 12/1998 |
| WO | WO 91/05549 | 5/1991 |
| WO | WO 94/01113 | 1/1994 |
| WO | WO 94/04525 | 3/1994 |
| WO | WO 94/12476 | 6/1994 |
| WO | WO 94/14796 | 7/1994 |

(Continued)

OTHER PUBLICATIONS

Zingg et al., The Oxytocin Receptor, TRENDS in Endocrinology and Metabolism, vol. 14, No. 5, pp. 222-227, Jul. 2003.*

(Continued)

*Primary Examiner*—Brenda Coleman
(74) *Attorney, Agent, or Firm*—Woodcock Washburn LLP

(57) ABSTRACT

The present invention provides novel tricyclic benzodiazepine carboxamides compounds and methods and pharmaceutical compositions utilizing them for the treatment and/or prevention and/or suppression of disorders which may be remedied or alleviated by oxytocin antagonist activity, including prevention and/or suppression suppression of preterm labor, suppression of labor at term prior to caesarean delivery, and for the treatment of dysmenorrhea. These compounds are also useful in enhancing fertility rates, enhancing survival rates and synchronizing estrus in farm animals; and may be useful in the prevention and treatment of disfunctions of the oxytocin system in the central nervous system including obsessive compulsive disorder (OCD) and neuropsychiatric disorders.

21 Claims, No Drawings

FOREIGN PATENT DOCUMENTS

| WO | WO 94/20473 | 9/1994 |
|----|-------------|--------|
| WO | WO 96/09824 | 4/1996 |
| WO | WO 96/22282 | 7/1996 |
| WO | WO 96/22292 | 7/1996 |
| WO | WO 96/22294 | 7/1996 |
| WO | WO 96/22775 | 8/1996 |
| WO | WO 97/25992 | 7/1997 |
| WO | 98/20011    | 5/1998 |
| WO | 99/06409    | 2/1999 |
| WO | WO 99/24051 | 5/1999 |

OTHER PUBLICATIONS

Mats Akerlund, Acta Obstet. Gynecol. Scand., 1987, 459-461, 66.
Mats Akerlund, Reg. Pept., 1993, 187-191, 45.
Ian M. Bell et al., J. Med. Chem., 1998, 2146-2163, 41.
Ya Li Chen et al., Eur. J. Pharmacol., 1999, 25-51, 376.
J.J. Evans et al., J. Endocrinol., 1989, 107-116, 122.
Ben E. Evans et al., J. Med. Chem., 1993, 3993-4006, 36.
Ben E. Evans et al., J. Med. Chem., 1992, 3919-3927, 35.
Anna-Riitta Fuchs et al., Science, 1982, 1396-1398, 215.
Andre Giroux et al., Tetr. Lett., 1997, 3841-3844, 38.
T. Murphy Goodwin et al., Obstet. Gynecol., 1996, 331-336, 88.
Aleksandar Jovanovic et al., Br. J. Pharmacol., 1997, 1468-1474, 12.
Mario Maggi et al., J. Clin. Endocrinol. Metab., 1990, 1142-1154, 70.
A. Okano, J. Reprod. Dev., 1996, 67-70, 42 (Suppl.).
D.J. Pettibone et al., Biochem. Soc. Trans., 1997, 1051-1057, 25(3).
V. Rettori et al., Proc. Nat. Acad. Sci. U.S.A., 1997, 2741-2744, 94.
G. Robinson et al., J. Endocrinol., 1990, 425-432, 125.
Olga Wellnitz et al., J. Dairy Res., 1999, 1-8, 66.
Gabor L. Kovacs et al., Psychoneuroendocrinology, 1998, 945-962, 23(8).
Margaret M. McCarthy et al., Molecular Medicine Today, 1997, 269-275, 3(6).
James. F. Leckman et al., Psychoeuroendocrinology, 1994, 723-749, 19(8).
Banker, G. S. et al., "Modern Pharmaceutics, 3ed.", Marcel Dekker, New York, 1996, p. 596.
PubMed Abstract 12848639, also cited as Acta Obstet Gynecol, 2003, 82(8), 687-704.
PubMed Abstract 12436949, also cited as Prog Brain Res, 2002, 139, 359-65.
PubMed Abstract 9891619, also cited as Clin Perinatol, 1998, 25(4), 859-71.
Wolff, Manfred E., "Burger's Medicinal Chemistry, 5ed, Part 1", John Wiley & Sons, 1995, pp. 975-977.

* cited by examiner

CYCLOHEXYLPHENYL CARBOXAMIDES TOCOLYTIC OXYTOCIN RECEPTOR ANTAGONISTS

This application claims priority from copending provisional application Ser. No. 60/283,389, filed Apr. 12, 2001, the entire disclosure of which is hereby incorporated by reference.

This invention concerns novel tricyclic benzodiazepine carboxamides which act as competitive oxytocin receptor antagonists, as well as methods of their manufacture, methods of treatment and pharmaceutical compositions utilizing these compounds. The compounds of the present invention are useful therapeutic agents in mammals, particularly in humans. More specifically, they are useful in the prevention and/or suppression of preterm labor, for the suppression of labor at term prior to caesarean delivery, to facilitate antinatal transport to a medical facility, and for the treatment of dysmenorrhea. These compounds are also useful in enhancing fertility rates, enhancing survival rates and synchronizing estrus in farm animals and may be useful in the prevention and treatment of disfunctions of the oxytocin system in the central nervous system including obsessive compulsive disorder (OCD) and neuropsychiatric disorders.

BACKGROUND OF THE INVENTION

Premature labor remains the leading cause of perinatal mortality and morbidity. Infant mortality dramatically decreases with increased gestational age. The survival rate of prematurely born infants increases from 20% at 24 weeks to 94% at 30 weeks. Moreover the cost associated with the care of an infant born prematurely is extremely high. While many agents have been developed for the treatment of premature labor in the last 40 years, the incidence of pre-term births and low birth weight infants has remained relatively unchanged. Therefore there remains an unmet need for the development of a safe and effective treatment of preterm labor.

Tocolytic (uterine relaxing) agents currently in use include $\beta_2$ adrenergic receptor agonists such as Ritodrine which is moderately effective in suppressing preterm labor, but it is associated with maternal hypotension, tachycardia, and metabolic side effects. Several other agents have been used to suppress premature labor, including other $\beta_2$ adrenergic agonists (terbutaline, albuterol), magnesium sulfate, NSAIDs (indomethacin), and calcium channel blockers. The consensus is that none of these agents are very effective; there is no clinical evidence showing that these compounds can prolong gestation for more than 7 days (Johnson, *Drugs*, 45, 684–692 (1993)). Furthermore, their safety profile is not ideal. Adverse effects include respiratory depression and cardiac arrest (magnesium sulfate), hemodynamic effects (calcium channel blockers), premature closure of the ductus arteriosus and oligohydramnios (NSAIDs; prostaglandin synthase inhibitors). Therefore, there is an unmet need for safer and more efficacious agents for the treatment of preterm labor with better patient tolerability. Specific requirements with regard to safety include a product with no or low rates of tachycardia, limited anxiety, improved fetal safety, and few, if any, adverse cardiovascular effects.

One target of interest is the oxytocin receptor in the uterus, and a selective oxytocin receptor antagonist has been proposed as an ideal tocolytic agent. While the exact role of oxytocin (OT) in parturition has not been clearly defined, there is evidence strongly suggesting that it may play a critical role in the initiation and progression of labor in humans (Fuchs et al. *Science* 215, 1396–1398 (1982); Maggi et al. *J. Clin. Endocrinol. Metab.* 70, 1142–1154 (1990); Åkerlund, *Reg. Pept* 45, 187–191 (1993); Åkerlund, *Int. Congr. Symp. Semin. Ser., Progress in Endocrinology* 3, 657–660 (1993); Åkerlund et al., in *Oxytocin,* Ed. R. Ivell and J. Russel, Plenum Press, New York, pp 595–600 (1995)). Preliminary clinical trials with oxytocin receptor antagonists support the notion that a blockade of OT receptors reduces uterine myometrial activity and delays the onset of labor (Åkerlund et al., *Br. J. Obst. Gynaecol.* 94, 1040–1044, (1987); Andersen et al., *Am. J. Perinatol.* 6, 196–199 (1989); Melin, *Reg. Pept.* 45, 285–288 (1993)). Thus, a selective oxytocin antagonist is expected to block the major effects of oxytocin exerted mainly on the uterus at term, and to be more efficacious than current therapies for the treatment of preterm labor. By virtue of its direct action on the receptors in the uterus an oxytocin antagonist is also expected to have fewer side effects and an improved safety profile.

The following prior art references describe peptidic oxytocin antagonists: Hruby et al., Structure-Activity Relationships of Neurohypophyseal Peptides, in *The Peptides: Analysis, Synthesis and Biology;* Udenfriend and Meienhofer Eds., Academic Press, New York, Vol. 8, 77–207 (1987); Pettibone et al., *Endocrinology,* 125, 217 (1989); Manning et al., Synthesis and Some Uses of Receptor-Specific Agonists and Antagonists of Vasopressin and Oxytocin, *J. Recept. Res.,* 13, 195–214 (1993); Goodwin et al., Dose Ranging Study of the Oxytocin Antagonist Atosiban in the Treatment of Preterm Labor, *Obstet. Gynecol.,* 88, 331–336 (1996). Peptidic oxytocin antagonists suffer from a lack of oral activity and many of these peptides are non-selective antagonists since they also exhibit vasopressin antagonist activity. Bock et al. [*J. Med. Chem.* 33, 2321 (1990)], Pettibone et al. [*J. Pharm. Exp. Ther.* 256, 304 (1991)], and Williams et al. [*J. Med. Chem.,* 35, 3905 (1992)] have reported on potent hexapeptide oxytocin antagonists which also exhibit weak vasopressin antagonistic activity in binding to $V_1$ and $V_2$ receptors.

Various non-peptidic oxytocin antagonists and/or oxytocin/vasopressin (AVP) antagonists have recently been reported by Pettibone et al., *Endocrinology,* 125, 217 (1989); Yamamura et al., *Science,* 252, 572–574 (1991); Evans et al., *J. Med. Chem.,* 35, 3919–3927 (1992); Pettibone et al., *J. Pharmacol. Exp. Ther,* 264, 308–314 (1992); Ohnishi et al., *J. Clin. Pharmacol.* 33, 230–238, (1993); Evans et al., *J. Med. Chem.* 36, 3993–4006 (1993); Pettibone et al., *Drug Dev. Res.* 30, 129–142 (1993); Freidinger et al., General Strategies in Peptidomimetic Design: Applications to Oxytocin Antagonists, in *Perspect Med. Chem.* 179–193 (1993), Ed. B. Testa, Verlag, Basel, Switzerland; Serradeil-LeGal, *J. Clin. Invest.,* 92, 224–231 (1993); Williams et al., *J. Med. Chem.* 37, 565–571 (1994); Williams et al., *Bioorg. Med. Chem.* 2, 971–985 (1994); Yamamura et al., *Br. J. Pharmacol.,* 105, 546–551 (1995); Pettibone et al., *Advances in Experimental Medicine and Biology* 395, 601–612 (1995); Williams et al., *J. Med. Chem.* 38, 4634–4636 (1995); Hobbs et al., *Biorg. Med. Chem. Lett.* 5, 119 (1995); Williams et al., *Curr. Pharm. Des.* 2, 41–58 (1996); Freidinger et al., *Medicinal Research Reviews,* 17, 1–16 (1997); Pettibone et al., *Biochem. Soc. Trans.* 25 (3), 1051–1057 (1997); Bell et al., *J. Med. Chem.* 41, 2146–2163 (1998); Kuo et al., *Bioorg. Med. Chem. Lett.* 8, 3081–3086 (1998); Williams et al., *Biorg. Med. Chem. Lett.* 9, 1311–1316 (1999).

Certain carbostyril derivatives and bicyclic azepines are disclosed as oxytocin and vasopressin antagonists by Ogawa et al. in WO 94/01113 (1994); benzoxazinones are disclosed as oxytocin and vasopressin receptor antagonists by Sparks et al. in WO 97/25992 (1997); Williams et al. disclose piperidine oxytocin and vasopressin receptor antagonists in WO 96/22775 (1996); Bock et al. disclose benzoxazinone and benzopyrimidinone piperidines useful as oxytocin and vasopressin receptor antagonists in U.S. Pat. No. 5,665,719

(1997); piperazines and spiropiperidines useful as oxytocin and vasopressin receptor antagonists are disclosed by Evans et al. in U.S. Pat. No. 5,670,509 (1997) and by Bock et al. in U.S. Pat. No. 5,756,504 (1998); Bell et al. disclose piperazine oxytocin receptor antagonists in UK Patent Application, GB 2 326 639 A (1998); Bell et al. disclose benzoxazinone and quinolinone oxytocin and vasopressin receptor antagonists in UK Patent Application GB 2 326 410 A (1998); Bell et al. disclose benzoxazinone oxytocin and vasopressin receptor antagonists in U.S. Pat. No. 5,756,497 (1998); Matsuhisa et al. disclose difluoro tetrahydrobenzazepine derivatives as oxytocin antagonists in WO 98/39325 (1998); Ogawa et al. disclose heterocyclic bisamides with vasopressin and oxytocin antagonist activity in U.S. Pat. No. 5,753,644 (1998); and Ogawa et al. disclose benzazepine derivatives with anti-vasopressin activity, oxytocin antagonistic activity and vasopressin agonist activity, useful as vasopressin antagonists, vasopressin agonists and oxytocin antagonists in WO 97/22591 (1997) and U.S. Pat. No. 6,096,736 (2000).

Trybulski et al. disclose 3-carboxamide derivatives of pyrrolobenzodiazepine bisamides with vasopressin antagonist activity in U.S. Pat. No. 5,880,122 (1999); bicyclic thienoazepines with vasopressin and oxytocin receptor antagonist activity are disclosed by Albright et al. in WO 96/22294 (1996) and U.S. Pat. No. 5,654,297 (1997); and tricyclic benzazepines with vasopressin and oxytocin receptor antagonist activity are disclosed by Albright et al. in U.S. Pat. No. 5,849,735 (1998).

Albright et al. broadly disclose tricyclic benzazepine vasopressin antagonists in WO 96/22282A1 (1996).

Venkatesan et al. broadly disclose tricyclic benzazepines with vasopressin and oxytocin antagonist activity in U.S. Pat. No. 5,521,173 (1996), WO 96/22292 (1996), and in U.S. Pat. No. 5,780,471 (1998).

Compounds which behave as potent oxytocin antagonists can bind with high affinity and selectivity to the oxytocin receptors, thus preventing oxytocin from binding to its receptors and exerting its biological and pharmacologic effects in vivo. They can be useful for the treatment and/or prevention and/or suppression of preterm labor, for the suppression of term labor prior to a caesarian delivery, and to facilitate antinatal transport to a medical facility. They also can produce contraception in mammals given that oxytocin antagonists have been shown to inhibit the release of oxytocin-stimulated luteneizing hormone (LH) from pituitary cells (Rettori et al., Proc. Nat. Acad. Sci. U.S.A. 94, 2741–2744 (1997); Evans et al., J. Endocrinol., 122, 107–116 (1989); Robinson et al., J. Endocrinol. 125, 425–432 (1990)).

Oxytocin antagonists have the ability to relax uterine contractions induced by oxytocin in mammals and thus, can be also useful for the treatment of dysmenorrhea, a condition chracterized by pain during menstruation (Åkerlund, Int. Congr. Symp. Semin. Ser., Progress in Endocrinology 3, 657–660 (1993); Åkerlund, Reg. Pept. 45, 187–191 (1993); Melin, Reg. Pept. 45, 285–288 (1993)). Primary dysmenorrhea is associated with ovulatory cycles, and it is the most common complaint of gynecologic patients. Myometrial hypercontractility and decreased blood flow to the uterus are thought to be causative factors for for the symptoms of primary dysmenorrhea (Åkerlund, Acta Obstet. Gynecol. Scand. 66, 459–461 (1987). In particular, vasoconstriction of small uterine arteries by vasopressin and oxytocin is thought to produce tissue ischemia and pain (Jovanovic et al., Br. J. Pharmacol. 12, 1468–1474 (91997); Chen et al., Eur. J. Pharmacol. 376, 25–51 (1999)).

The administration of oxytocin receptor antagonists to farm animals after fertilization have been found to enhance fertility rates by blocking oxytocin induced luteolysis leading to embryonic loss (Hickey et al., WO 96/09824 A2 (1996), Sparks et al., WO 97/25992 A1 (1997); Sparks et al., U.S. Pat. No. 5,726,172 A (1998)). Thus, oxytocin receptor antagonists can be useful in farm animal husbandry to control timing of parturition and delivery of newborns resulting in enhanced survival rates. They can be also useful for the synchronization of estrus by preventing oxytocin induced corpus luteum regression and by delaying estrus (Okano, J. Reprod. Dev. 42 (Suppl.), 67–70 (1996)). Furthermore oxytocin receptor antagonists have been found to have a powerful effect in inhibiting oxytocin-induced milk ejection in dairy cows (Wellnitz et al., Journal of Dairy Research 66, 1–8 (1999)).

Oxytocin is also synthesized in the brain and released in the central nervous system. Recent studies have established the importance of central oxytocin in cognitive, affiliative, sexual and reproductive behavior, and in regulating feeding, grooming and response to stress in animals. Oxytocin may also influence normal behavior in humans. Modulators of oxytocin binding to its receptors in the central nervous system may be useful in the prevention and treatment of disfunctions of the oxytocin system, including obsessive compulsive disorder (OCD) and other neuropsychiatric disorders (Kovacs et al., Psychoneuroendocrinology 23, 945–962 (1998); McCarthy et al., U.K. Mol. Med. Today 3, 269–275 (1997); Bohus, Peptidergic Neuron, [Int Symp. Neurosecretion], 12th (1996), 267–277, Publ. Birkhauser, Basel, Switz.; Leckman et al., Psychoneuroendocrinology 19, 723–749 (1994)).

Compounds which act to competitively inhibit binding of vasopressin to its receptors are useful in the treatment or prevention of state diseases involving vasopressin disorders in mammals, including vasodilation and aquaresis (freewater diuresis), treating hypertension and inhibiting platelet aggregation. They are useful in the treatment of congestive heart failure, cirrhosis with ascites, and in the syndrome of inappropriate secretion of antiduretic hormone (SIADH). Furthermore, vasopressin receptor antagonists have been found to be useful in treating disturbances or illnesses of the inner ear, particularly those related to Meniere's disease (Zenner et al., WO 99/2405-A2 (1999)); and for the prevention and treatment of ocular circulatory disorders, particularly intraocular hypertension or glaucoma and vision disorders such as shortsightedness (Ogawa et al., WO 99/38533-A1 (1999)).

SUMMARY OF THE INVENTION

This invention relates to novel compounds selected from those of Formula (I):

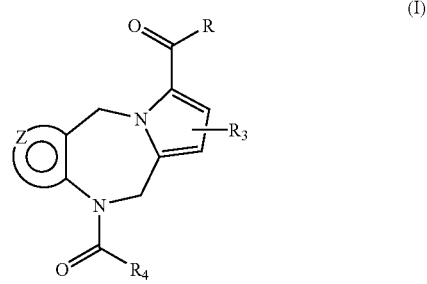

wherein:

-continued

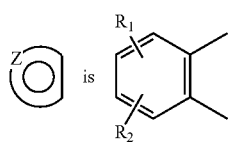 is

R₁ and R₂ are, independently, selected from hydrogen, (C₁–C₆)lower alkyl, halogen, cyano, trifluoromethyl, hydroxy, amino, (C₁–C₆) lower alkylamino, (C₁–C₆) lower alkoxy, (C₁–C₆) lower alkoxycarbonyl, carboxy, —CONH₂, —CONH (C₁–C₆) lower alkyl, or —CON [(C₁–C₆) lower alkyl]₂;

R₃ is a substituent selected from hydrogen, (C₁–C₆) lower alkyl, (C₁–C₆) lower alkoxy, hydroxy, amino, (C₁–C₆) lower alkylamino, —CO lower alkyl (C₁–C₆), or halogen;

R₄ consists of the moiety:

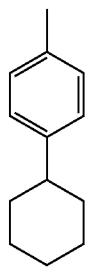

and R is selected from the group of (C₁–C₆) lower alkyl, hydroxy, —O[(C₁–C₆) lower alkyl], aryl (optionally substituted with one to three substituents selected from the group consisting of (C₁–C₆) lower alkyl or halogen), —NHNH2, —NHOR₃₁, —CH=CH—N[R₃₂]₂, or any of the following groups:

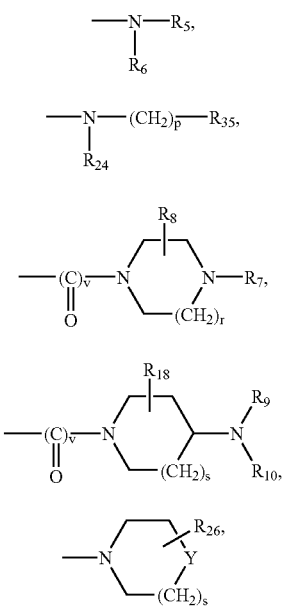

-continued

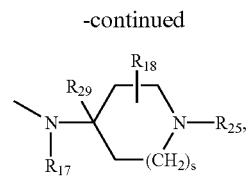  f

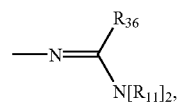  g

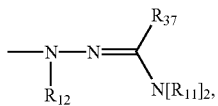  h

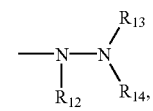  i

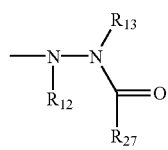  j wherein:
R₅ and R₆ are independently, selected from the group of hydrogen, lower alkyl, (C₃–C₆) lower alkenyl, (C₃–C₈) cycloalkyl optionally mono- or di- (C₁–C₆) lower alkyl substituted, bicycloalkyl including but not limited to adamantanyl, adamantane lower alkyl, bornyl, norbornyl, or quinuclidyl;

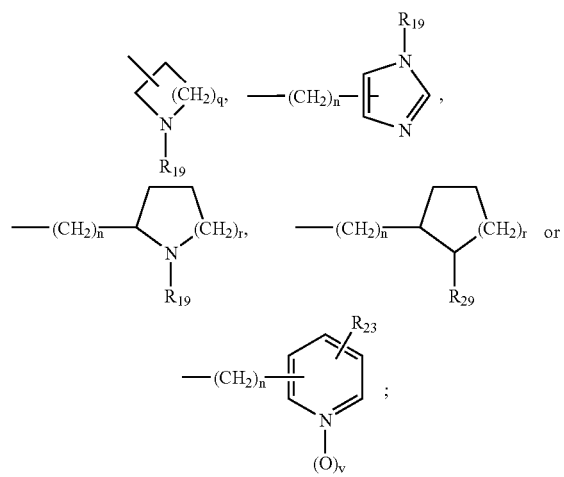

cycloalkyl lower alkyl, halo lower alkyl, cyano lower alkyl, lower alkyl thiol, alkoxycarbonyl lower alkyl, alkylthio lower alkyl, indolyl lower alkyl; aryl, optionally substituted with one to three substituents selected independently, from the group of lower alkyl, hydroxy, lower alkoxy, aryl lower alkoxy, halogen, —CF₃, —OCF₃, —OCF₂H, —OCH₂F, —OCH₂CF₃, —OCF₂CF₃, —OCH₂CHF₂, alkylamido lower alkyl, dialkylamido lower alkyl, morpholinyl, thiomorpholinyl, pyrrolidinyl, piperidinyl, —SCF$_3$, —SO$_2$[lower alkyl], sulfonyl cycloalkyl,

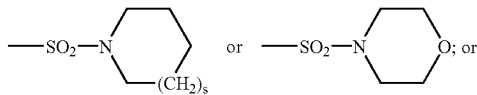

(C$_7$–C$_{12}$) aryl lower alkyl, wherein the aryl moiety is optionally substituted with halogen or alkoxy; with the proviso that R$_5$ and R$_6$ can be taken together with the nitrogen to which they are attached to form an unsaturated heteroaromatic ring containing 2 nitrogen atoms;

R$_7$ is selected from hydrogen, (C$_1$–C$_6$) lower alkyl, (C$_3$–C$_6$) lower alkenyl, (C$_3$–C$_6$) lower alkynyl, (C$_3$–C$_8$) cycloalkyl, —CONH$_2$, —CON[lower alkyl]$_2$, carbonyl lower alkyl, lower alkyl CONH[lower alkyl], lower alkyl CON[lower alkyl]$_2$, cycloalkylamino carbonyl, cycloalkylamino carbonyl lower alkyl, arylamino carbonyl lower alkyl, lower alkoxy carbonyl, lower alkoxy carbonyl lower alkyl, —(CH$_2$)$_p$—N[lower alkyl]$_2$, —(CH$_2$)$_p$—N[lower alkenyl]$_2$, —CH[aryl]$_2$ wherein the aryl is optionally substituted by (C$_1$–C$_6$) lower alkyl or halogen;

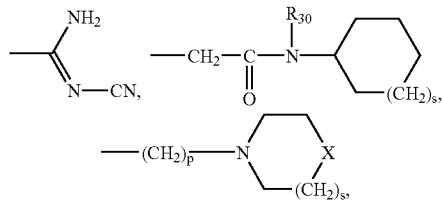

benzodioxolyl, benzodioxolyl lower alkyl, benzodioxanyl, benzodioxanyl lower alkyl, pyridyl, pyrimidinyl, pyridazinyl, furancarbonyl, —SO$_2$[lower alkyl], aryl optionally substituted by one to three substituents selected independently, from the group of hydrogen, halogen, lower alkyl, lower alkenyl, lower alkynyl, lower alkoxy, —CF$_3$, —OCF$_3$, —OCF$_2$H, —OCH$_2$F, —OCH$_2$CF$_3$, —OCF$_2$CF$_3$, —OCH$_2$CHF$_2$, —CO lower alkyl, —CN, nitro, —SCH$_3$, aryl lower alkoxy, aryl lower alkoxy carbonyl, indolyl, morpholino or thiomorpholino; or (C$_7$–C$_{12}$) lower aralkyl wherein the aryl moiety is optionally substituted with halogen, or lower alkoxy; or is a substituent selected from the group of

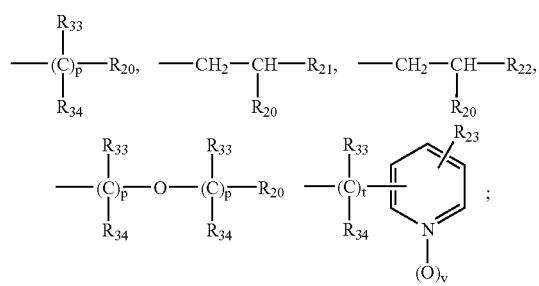

or a substituent selected from the group of

R$_8$ represents one to three substituents selected, independently, from the group of hydrogen or (C$_1$–C$_6$) lower alkyl;

R$_9$ and R$_{10}$ are, independently, selected from the group of hydrogen or (C$_1$–C$_6$) lower alkyl, with the proviso that R$_9$ and R$_{10}$ taken together with the nitrogen to which they are attached may form a 5-membered saturated heterocycle; or 6-membered saturated heterocycle optionally containing one additional O, S, or N[lower alkyl];

R$_{11}$ is (C$_1$–C$_6$) lower alkyl;

R$_{12}$ is selected from the group of hydrogen, or (C$_1$–C$_6$) lower alkyl;

R$_{13}$ and R$_{14}$ are, independently, selected from the group of hydrogen, (C$_1$–C$_6$) lower alkyl, (C$_7$–C$_{11}$) aryl lower alkyl, with the proviso that R$_{13}$ and R$_{14}$ taken together with the nitrogen atom to which they are attached may form a 4 to 8 membered saturated heterocycle, optionally containing one additional O, S or N(lower alkyl), all the above rings being optionally substituted with one or more alkyl groups; or a 5 membered unsaturated heterocycle containing 2 to 3 nitrogen atoms;

R$_{15}$ and R$_{16}$ are, independently, selected from hydrogen, (C$_1$–C$_6$) lower alkyl, or (C$_7$–C$_{12}$) aryl lower alkyl, with the proviso that R$_{15}$ and R$_{16}$ can be taken together with the nitrogen atom to which they are attached to form a 5 to 7 membered saturated heterocycle, optionally containing one additional O or S atom (all of the above rings being optionally substituted with 1 or more alkyl groups); or a 5-membered unsaturated heterocycle containing 1 to 3 nitrogen atoms;

R$_{17}$ is selected from the group of hydrogen, (C$_1$–C$_6$) lower alkyl, or (C$_7$–C$_{12}$) aryl lower alkyl;

R$_{18}$ represents one to three substituents selected, independently, from the group of hydrogen, (C$_1$–C$_6$) lower alkyl, or (C$_7$–C$_{12}$) aryl lower alkyl;

R$_{19}$ is selected from the group of hydrogen, (C$_1$–C$_6$) lower alkyl, or (C$_7$–C$_{12}$) aryl lower alkyl;

R$_{20}$ is selected from the group of hydroxy, lower alkoxy, or OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (c.f. Greene et al., *Protective Groups in Organic Syntheses*, 2$^{nd}$ and 3$^{rd}$ Edns., John Wiley & Sons, New York (1991, 1999));

R$_{21}$ is selected from the group of hydroxy lower alkyl, lower alkoxy lower alkyl, or lower alkyl OP wherein P is a hydroxy protecting group, defined as a group providing temporary protection against undesirable reactions during synthetic procedures and to be selectively removable. Common hydroxy protecting groups include, but are not limited to, tert-butyldimethylsilyl, tert-butyldiphenylsilyl, acetyl, trifluoroacetyl, benzyl, benzoyl, methoxymethyl, methylthiomethyl, and others well known in the art (c.f. Greene et al., *Protective Groups in Organic Syntheses*, 2$^{nd}$ and 3$^{rd}$ Edns., John Wiley & Sons, New York (1991, 1999)), the contents of which are incorporated herein by reference;

R$_{22}$ is (C$_1$–C$_6$) lower alkyl, or (C$_7$–C$_{12}$) aryl lower alkyl;

R$_{23}$ represents one or two substituents selected, independently, from the group of hydrogen, (C$_1$–C$_6$) lower alkyl, halogen, trifluoromethyl, (C$_1$–C$_6$) lower alkoxy, or

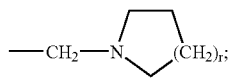

$R_{24}$ is selected from hydrogen, $(C_1-C_6)$ lower alkyl, $(C_1-C_{12})$ aryl lower alkyl, or —$(CH_2)_p$—N (lower alkyl)$_2$;

$R_{25}$ is selected from the group of $(C_1-C_6)$ lower alkyl, $(C_7-C_{12})$ aryl lower alkyl, lower alkoxy carbonyl, or SO$_2$[lower alkyl];

$R_{26}$ is selected from the group of hydrogen, $(C_1-C_6)$ lower alkyl, —N[lower alkyl]$_2$, cycloalkylamino lower alkyl or

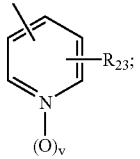

when Y=CH$_2$; or is selected from the group of hydrogen and $(C_1-C_6)$ lower alkyl when Y=X;

$R_{27}$ is either $R_{28}$, or —NHR$_{38}$;

$R_{28}$ is selected from the group of $(C_1-C_6)$ lower alkyl, $(C_3-C_8)$ cycloalkyl, aryl optionally substituted by one to three substituents chosen from the group of halogen or $(C_1-C_6)$ lower alkyl;

$R_{29}$ is selected from the group of hydrogen, or $(C_1-C_6)$ lower alkyl;

$R_{30}$ is selected from the group of hydrogen, or $(C_1-C_6)$ lower alkyl, or $(C_7-C_{12})$ aryl lower alkyl;

$R_{31}$ is selected from the group of hydrogen or $(C_1-C_6)$ lower alkyl;

$R_{32}$ is $(C_1-C_6)$ lower alkyl;

$R_{33}$ and $R_{34}$ are, independently, selected from the group of hydrogen, or $(C_1-C_6)$ lower alkyl, or $(C_7-C_{12})$ aryl lower alkyl;

$R_{35}$ is selected from the group of:

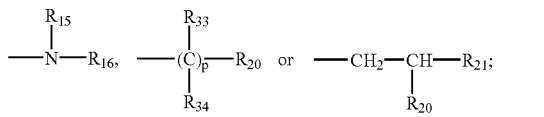

$R_{36}$ and $R_{37}$ are selected, from the group of hydrogen or $(C_1-C_6)$ lower alkyl;

$R_{38}$ is selected from the group of $(C_1-C_6)$ lower alkyl, $(C_3-C_8)$ cycloalkyl; aryl, optionally substituted by one to three substituents chosen from the group of halogen, or $(C_1-C_6)$ lower alkyl;

X is O, S, SO, SO$_2$, or N[lower alkyl];
Y is CH$_2$, or X;
n is an integer from 1 to 4;
p is an integer from 2 to 4;
q is an integer from 1 to 5;
r is an integer from 1 to 2;
s is an integer from 0 to 1;
t is an integer from 0 to 2;
v is an integer from 0 to 1;

and the pharmaceutically acceptable salts, or pro-drug forms thereof.

Preferred compounds within this genus include those of the formula:

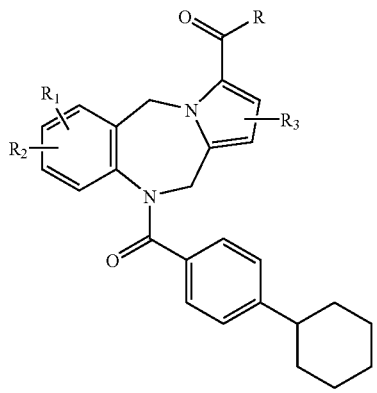

$R^1$ and $R_2$ are, independently, selected from hydrogen, $C_1-C_6$ alkyl, halogen, cyano, trifluoromethyl, hydroxy, amino, $(C_1-C_6)$ alkylamino, $C_1-C_6$ alkoxy, —C(O)O—$(C_1-C_6$ alkyl), carboxy, —CONH$_2$, —CONH$(C_1-C_6)$ lower alkyl, or —CON[$(C_1-C_6)$ lower alkyl]$_2$;

$R_3$ is a substituent selected from hydrogen, $(C_1-C_6)$ lower alkyl, $(C_1-C_6)$ lower alkoxy, hydroxy, amino, $(C_1-C_6)$ lower alkylamino, —CO lower alkyl $(C_1-C_6)$, or halogen;

R is selected from lower alkyl, —NHNH$_2$, —NHOR$_{31}$; or —CH═CH—N[R$_{32}$]$_2$; lower alkoxy; phenyl optionally substituted by from one to three substituents selected from $(C_1-C_6)$ lower alkyl or halogen; or a moiety of the formulae:

a
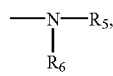

b
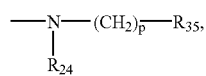

c
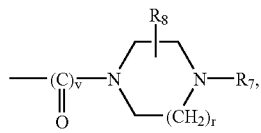

d
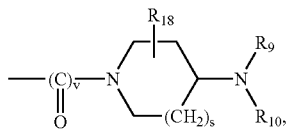

e
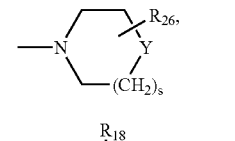

f
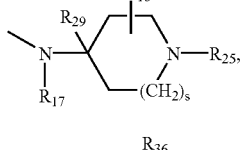

g
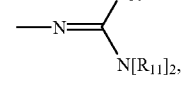

-continued

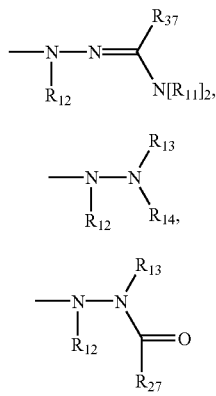

R$_5$ and R$_6$ are independently, selected from the group consisting of hydrogen, lower alkyl, (C$_3$–C$_6$) lower alkenyl, (C$_3$–C$_8$) cycloalkyl optionally mono- or di-(C$_1$–C$_6$) lower alkyl substituted; or phenyl, optionally substituted with one to three substituents selected independently, from the group consisting of lower alkyl, hydroxy, lower alkoxy, aryl lower alkoxy, halogen, —CF$_3$, —OCF$_3$, —OCF$_2$H, —OCH$_2$F, —OCH$_2$CF$_3$, —OCF$_2$CF$_3$, —OCH$_2$CHF$_2$, alkylamido lower alkyl, or dialkylamido lower alkyl; or R$_5$ and R$_6$ can be taken together with the nitrogen to which they are attached to form an unsaturated heteroaromatic ring containing 2 nitrogen atoms;

R$_7$ is selected from the group consisting of hydrogen, (C$_1$–C$_6$) lower alkyl, (C$_3$–C$_6$) lower alkenyl, (C$_3$–C$_6$) lower alkynyl, (C$_3$–C$_8$) cycloalkyl, —CONH$_2$, —CON[lower alkyl]$_2$, carbonyl lower alkyl, lower alkyl CONH[lower alkyl], lower alkyl CON[lower alkyl]$_2$, cycloalkylamino carbonyl; or R$_7$ is —CH[aryl]$_2$ wherein the aryl is phenyl optionally substituted by (C$_1$–C$_6$) lower alkyl, lower alkoxy, or halogen; or R$_7$ is a pyridine or pyrimidine moiety; or R$_7$ is a moiety selected from the group of:

R$_{28}$ is selected from the group consisting of (C$_1$–C$_6$) alkyl, (C$_3$–C$_8$) cycloalkyl, or phenyl optionally substituted by 1 to 3 groups selected from halogen or (C$_1$–C$_6$) alkyl;

R$_{29}$ is selected from the group of hydrogen, or (C$_1$–C$_6$) lower alkyl;

R$_{35}$ is the moiety

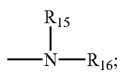

R$_{36}$ and R$_{37}$ are selected, from the group consisting of hydrogen or (C$_1$–C$_6$) lower alkyl;

R$_{38}$ is selected from the group consisting of (C$_1$–C$_6$) lower alkyl, (C$_3$–C$_8$) cycloalkyl; aryl, optionally substituted by one to three substituents chosen from the group consisting of halogen, or (C$_1$–C$_6$) lower alkyl;

Y is CH$_2$;

p is an integer from 2 to 4;

r is an integer from 1 to 2;

s is an integer from 0 to 1; and v is an integer from 0 to 1;

or a pharmaceutically acceptable salt or pro-drug form thereof.

Other preferred compounds of this invention include those of the formula:

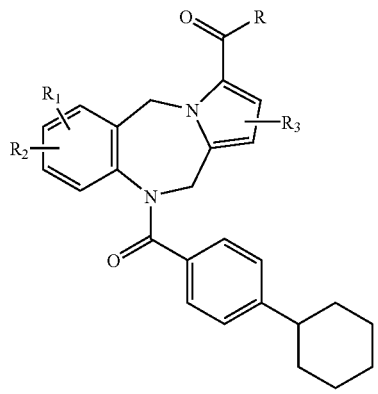

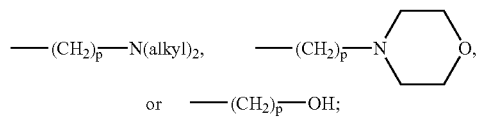

R$_8$ represents one to three substituents selected, independently, from H or C$_1$–C$_6$ alkyl;

R$_9$ and R$_{10}$ are, independently, selected from the group consisting of hydrogen or (C$_1$–C$_6$) lower alkyl, with the proviso that R$_9$ and R$_{10}$ taken together with the nitrogen to which they are attached may form a 5-membered saturated heterocycle; or 6-membered saturated heterocycle optionally containing one additional O, S, or N[lower alkyl];

R$_{11}$ is (C$_1$–C$_6$) lower alkyl;

R$_{12}$ is selected from the group consisting of hydrogen, or (C$_1$–C$_6$) lower alkyl;

R$_{13}$ and R$_{14}$ are, independently, selected from the group consisting of hydrogen, or (C$_1$–C$_6$)alkyl;

R$_{15}$ and R$_{16}$ are, independently, selected from hydrogen, (C$_1$–C$_6$) lower alkyl, with the proviso that R$_{15}$ and R$_{16}$ can be taken together with the nitrogen atom to which they are attached to form either:
  a) a 5 to 7 membered saturated heterocycle, optionally containing one additional O or S atom (all of the above rings being optionally substituted with from 1 to 3 C$_1$–C$_6$ alkyl groups, preferably C$_1$–C$_3$ alkyl groups); or
  b) a 5-membered unsaturated heterocycle containing 1 to 3 nitrogen atoms;

R$_{17}$ is selected from the group of hydrogen, or (C$_1$–C$_6$) lower alkyl;

R$_{18}$ represents one to three substituents selected, independently, from the group consisting of hydrogen, (C$_1$–C$_6$) lower alkyl, or (C$_7$–C$_{12}$) aryl lower alkyl;

R$_{24}$ is selected from hydrogen, (C$_1$–C$_6$) lower alkyl, (C$_1$–C$_{12}$) aryl lower alkyl, or —(CH$_2$)$_p$—N (lower alkyl)$_2$;

R$_{25}$ is (C$_1$–C$_6$) lower alkyl;

R$_{26}$ is selected from the group consisting of H, (C$_1$–C$_6$) alkyl, cycloalkylamino lower alkyl, or —N[lower alkyl]$_2$;

R$_{27}$ is either R$_{28}$, or —NHR$_{38}$;

R$_1$ and R$_2$ are, independently, selected from hydrogen, C$_1$–C$_6$ alkyl, halogen, cyano, trifluoromethyl, hydroxy, amino, C$_1$–C$_6$ alkylamino, C$_1$–C$_8$ alkoxy, —C(O)O—

($C_1$–$C_6$ alkyl), carboxy, —$CONH_2$, —CONH—($C_1$–$C_6$ alkyl), or, —CON[($C_1$–$C_6$) lower alkyl]$_2$;

$R_3$ is a substituent selected from hydrogen, $C_1$–$C_6$ alkyl, $C_1$–$C_6$ alkoxy, OH, amino, $C_1$–$C_6$ alkylamino, —CO—($C_1$–$C_6$ alkyl), or halogen;

R is selected from —$NHNH_2$, —$NHOR_{31}$; or —CH=CH—N[$R_{32}$]$_2$; —NH—NH—C(O)—($C_3$–$C_6$ cycloalkyl); —NHNH($C_1$–$C_6$ alkyl) or —NHN($C_1$–$C_6$ alkyl)$_2$; or a) phenyl optionally substituted by from one to three substituents selected from ($C_1$–$C_6$) lower alkyl, —C(O)—($C_1$–$C_6$) alkyl, —C(O)—$Cl_3$, halogen;

b) —NH-phenyl, —NH—NH—C(O)-phenyl or —NH—NH—C(O)—NH-phenyl, the phenyl rings of which are optionally substituted by from one to three substituents selected from $C_1$–$C_6$ alkyl, or halogen;

c) imidazolyl;

or a moiety of the formulae:

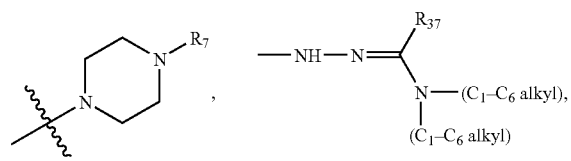

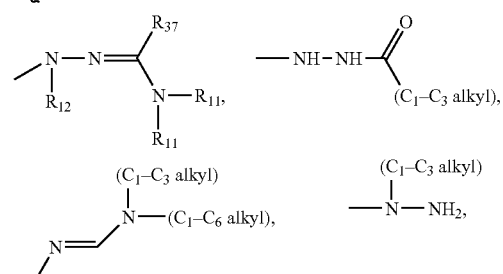

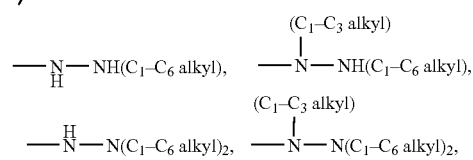

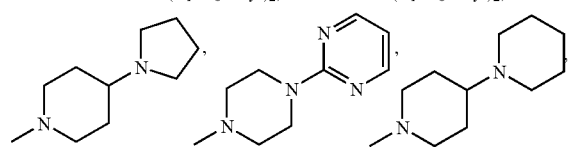

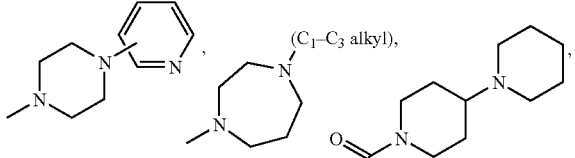

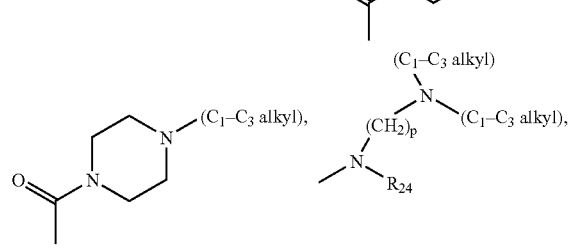

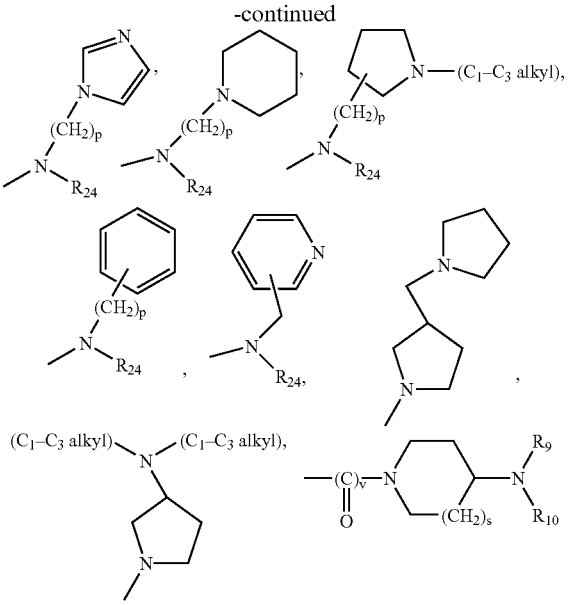

$R_7$ is selected from H, $C_1$–$C_6$ alkyl, $C_3$–$C_6$ alkenyl, $C_3$–$C_6$ alkynyl, —$C_1$–$C_6$ alkyl-OH, —$(CH_2)_p$—$NH_2$, —$(CH_2)_p$—NH[lower alkyl], —$(CH_2)_p$—N[lower alkyl]$_2$, —$(CH_2)_p$-morpholino; phenyl optionally substituted by from one to three substituents selected independently from the group consisting of H, halogen, $C_1$–$C_6$ alkyl, $C_3$–$C_6$ alkenyl, $C_3$–$C_6$ alkynyl, $C_3$–$C_6$ alkoxy, —$CF_3$, —$OCF_3$, —$OCF_2H$, —$OCH_2F$, —$OCH_2CF_3$, —$OCF_2CF_3$, —$OCH_2CHF_2$, —CO—$C_1$–$C_6$ alkyl, —CN, nitro, —$SCH_3$, $R_{11}$ is $C_1$–$C_6$ alkyl;

$R_{12}$ is H or $C_1$–$C_6$ alkyl;

$R_{24}$ is selected from H or $C_1$–$C_3$ alkyl;

$R_{36}$ and $R_{37}$ are independently selected from H or $C_1$–$C_3$ alkyl; and p is an integer from 2 to 4;

s is an integer from 0 to 1;

v is an integer from 0 to 1;

or a pharmaceutically acceptable salt form thereof.

As used herein the term "lower" in relation to alkoxy or alkyl is understood to refer to those groups having from 1 to 6 carbon atoms. Halogen refers to fluorine, chlorine, bromine or iodine.

The preferred compounds of this invention include:

Methyl 10-(4-cyclohexylbenzoyl)-3-[(4-methyl-1-piperazinyl)carbonyl]-10,11-dihydro-5H-pyrrolo[2,1-c][1,4]benzodiazepine-8-carboxylate hydrochloride salt;

10-(4-Cyclohexylbenzoyl)-10,11-dihydro-5H-pyrrolo[2,1-c][1,4]benzodiazepine-8-carboxylic acid sodium salt;

10-(4-Cyclohexyl-benzoyl)-3-[(4-methyl-1-piperazinyl)carbonyl]-10,11-dihydro-5H-pyrrolo[2,1-c][1,4]benzodiazepine-8-carboxylic acid;

10-(4-Cyclohexyl-benzoyl)-10,11-dihydro-5H-pyrrolo[2,1-c][1,4]benzodiazepine;

[4-(tert-Butyl)phenyl][10-(4-cyclohexyl-benzoyl)-10,11-dihydro-5H-pyrrolo[2,1-c][1,4]benzodiazepin-3-yl]methanone;

1-[10-(4-Cyclohexyl-benzoyl)-10,11-dihydro-5H-pyrrolo[2,1-c][1,4]benzodiazepin-3-yl]-ethanone;

2,2,2-Trichloro-1-[10-(4-cyclohexyl-benzoyl)-10,11-dihydro-5H-pyrrolo[2,1-c][1,4]benzodiazepin-3-yl]-1-ethanone;

10-(4-Cyclohexy-benzoyl)-10,11-dihydro-5H-pyrrolo[2,1-c][1,4]benzodiazepine-3-carboxylic acid hydrazide;

N'-{[10-(4-Cyclohexyl-benzoyl)-10,11-dihydro-5H-pyrrolo[2,1-c][1,4]benzodiazepin-3-yl]carbonyl}-N,N-dimethyl-ethanehydrazonamide;

N'-{[10-(4-Cyclohexyl-benzoyl)-10,11-dihydro-5H-pyrrolo[2,1-c][1,4]benzodiazepin-3-yl]carbonyl}-N,N-dimethyl-hydrazonoformamide;

N'-Acetyl-10-(4-cyclohexyl-benzoyl)-10,11-dihydro-5H-pyrrolo[2,1-c][1,4]benzodiazepine-3-carbonyl-hydrazide;

10-(4-Cyclohexyl-benzoyl)-N'-(2-methylbenzoyl)-10,11-dihydro-5H-pyrrolo[2,1-c][1,4]benzodiazepine-3-carbonyl-hydrazide;

10-(4-Cyclohexyl-benzoyl)-N'-(cyclopropylcarbonyl)-10,11-dihydro-5H-pyrrolo[2,1-c][1,4]benzodiazepine-3-carbonyl-hydrazide;

10-(4-Cyclohexylbenzoyl)-N'-(3-methylbenzoyl)-10,11-dihydro-5H-pyrrolo[2,1-c][1,4]benzodiazepine-3-carbonyl-hydrazide;

2-{[10-(4-Cyclohexyl-benzoyl)-10,11-dihydro-5H-pyrrolo[2,1-c][1,4]benzodiazepin-3-yl]carbonyl}-N-phenyl-1-hydrazinecarboxamide;

10-(4-Cyclohexyl-benzoyl)-10,11-dihydro-5H-pyrrolo[2,1-c][1,4]benzodiazepin-3-carboxamide;

10-(4-Cyclohexyl-benzoyl)-N-[(E)-(dimethylamino)methylidene-10,11-dihydro-5H-pyrrolo[2,1-c][1,4]benzodiazepine-3-carboxamide;

10-(4-Cyclohexyl-benzoyl)-N-[(E)-1-(dimethylamino)ethylidene-10,11-dihydro-5H-pyrrolo[2,1-c][1,4]benzodiazepine-3-carboxamide;

10-(4-Cyclohexyl-benzoyl)-N'-N'-dimethyl-10,11-dihydro-5H-pyrrolo[2,1-c][1,4]benzodiazepine-3-carbohydrazide;

(E)-1-[10-(4-Cyclohexyl-benzoyl)-10,11-dihydro-5H-pyrrolo[2,1-c][1,4]benzodiazepin-3-yl]-3-(dimethylamino)-2-propen-1-one;

10-(4-Cyclohexyl-benzoyl)-N-methyl-10,11-dihydro-5H-pyrrolo[2,1-c][1,4]benzodiazepine-3-carbohydrazide;

10-(4-Cyclohexyl-benzoyl)-10,11-dihydro-5H-pyrrolo[2,1-c][1,4]benzodiazepine-3-carboxylic acid;

[10-(4-Cyclohexyl-benzoyl)-10,11-dihydro-5H-pyrrolo[2,1-c][1,4]benzodiazepin-3-yl][4-(2-pyrimidinyl)-1-piperazinyl]methanone;

[10-(4-Cyclohexyl-benzoyl)-10,11-dihydro-5H-pyrrolo[2,1-c][1,4]benzodiazepin-3-yl](4-methyl-1-piperazinyl)-methanone;

[10-(4-Cyclohexyl-benzoyl)-10,11-dihydro-5H-pyrrolo[2,1-c][1,4]benzodiazepin-3-yl][4-(1-pyrrolidinyl)-1-piperidinyl]methanone;

[1,4']Bipiperidinyl-1'-yl-[10-(4-cyclohexyl-benzoyl)-10,11-dihydro-5H-pyrrolo[2,1-c][1,4]benzodiazepin-3-yl]-methanone;

[10-(4-Cyclohexyl-benzoyl)-10,11-dihydro-5H-pyrrolo[2,1-c][1,4]benzodiazepin-3-yl][4-(2-methylphenyl)-1-piperazinyl]-methanone;

[10-(4-Cyclohexyl-benzoyl)-10,11-dihydro-5H-pyrrolo[2,1-c][1,4]benzodiazepine 3-yl][4-(2-pyridinyl)-1-piperazinyl]-methanone;

10-(4-Cyclohexyl-benzoyl)-10,11-dihydro-5H-pyrrolo[2,1-c][1,4]benzaodiazepine-3-carboxylic acid (4-methoxyphenyl)-amide;

[10-(4-Cyclohexyl-benzoyl)-10,11-dihydro-5H-pyrrolo[2,1-c][1,4]benzodiazepin-3-yl](4-methyl-[1,4]-diazepan-1-yl)-methanone;

1-[1,4']Bipiperidinyl-1'-yl-2-[10-(4-cyclohexyl-benzoyl)-10,11-dihydro-5H-pyrrolo[2,1-c][1,4]benzodiazepin-3-yl]-ethane-1,2-dione;

1-[10-(4-Cyclohexyl-benzoyl)-10,11-dihydro-5H-pyrrolo[2,1-c][1,4]benzodiazepin-3-yl]-2-(4-methyl-1-piperazin-1-yl)-1,2-ethane-1,2-dione;

10-(4-Cyclohexyl-benzoyl)-N-[3-(dimethylamino)propyl]-10,11-dihydro-5H-pyrrolo[2,1-c][1,4]benzodiazepine-3-carboxamide;

10-(4-Cyclohexyl-benzoyl)-N-[2-(dimethylamino)-ethyl]-N-methyl-10,11-dihydro-5H-pyrrolo[2,1-c][1,4]benzodiazepine-3-carboxamide;

10-(4-Cyclohexyl-benzoyl)-N-[3-(dimethylamino)propyl]-N-methyl-10,11-dihydro-5H-pyrrolo[2,1-c][1,4]benzodiazepine-3-carboxamide;

10-(4-Cyclohexyl-benzoyl)-N-[3-(1H-imidazol-1-yl)propyl]-10,11-dihydro-5H-pyrrolo[2,1-c][1,4]benzodiazepine-3-carboxamide;

10-(4-Cyclohexyl-benzoyl)-N-[2-(1-piperidinyl)ethyl]-10,11-dihydro-5H-pyrrolo[2,1-c][1,4]benzodiazepine-3-carboxamide;

10-(4-Cyclohexyl-benzoyl)-N-[2-(1-methyl-2-pyrrolidinyl)ethyl]-10,11-dihydro-5H-pyrrolo[2,1-c][1,4]benzodiazepine-3-carboxamide;

10-(4-Cyclohexyl-benzoyl)-N-methyl-N-(1-methyl-4-piperidinyl)-10,11-dihydro-5H-pyrrolo[2,1-c][1,4]benzodiazepine-3-carboxamide;

10-(4-Cyclohexyl-benzoyl)-N-methyl-N-(1-methyl-3-pyrrolidinyl)-10,11-dihydro-5H-pyrrolo[2,1-c][1,4]benzodiazepine-3-carboxamide;

[10-(4-Cyclohexyl-benzoyl)-10,11-dihydro-5H-pyrrolo[2,1-c][1,4]benzodiazepin-3-yl]{4-[2-(dimethylamino)ethyl]-1-piperazinyl}methanone;

[10(4-Cyclohexyl-benzoyl)-10,11-dihydro-5H-pyrrolo[2,1-c][1,4]benzodiazepin-3-yl]{4-[2-(4-morpholinyl)ethyl]-1-piperazinyl}methanone;

(4-Allyl-1-piperazinyl)[10-(4-cyclohexyl-benzoyl)-10,11-dihydro-5H-pyrrolo[2,1-c][1,4]benzodiazepin-3-yl]methanone;

[10-(4-Cyclohexyl-benzoyl)-10,11-dihydro-5H-pyrrolo[2,1-c][1,4]benzodiazepin-3-yl](4-isopropyl-1-piperazinyl)methanone;

[10-(4-Cyclohexyl-benzoyl)-10,11-dihydro-5H-pyrrolo[2,1-c][1,4]benzodiazepin-3-yl]{4-[3-(dimethylamino)propyl]-1-piperazinyl}methanone;

[10-(4-Cyclohexyl-benzoyl)-10,11-dihydro-5H-pyrrolo[2,1-c][1,4]benzodiazepin-3-yl][(2S)-2-(1-pyrrolidinylmethyl)pyrrolidinyl]methanone;

[10-(4-Cyclohexyl-benzoyl)-10,11-dihydro-5H-pyrrolo[2,1-c][1,4]benzodiazepin-3-yl][(3R)-3-(dimethylamino)pyrrolidinyl]methanone;

[10-(4-Cyclohexyl-benzoyl)-10,11-dihydro-5H-pyrrolo[2,1-c][1,4]benzodiazepin-3-yl][4-(2-hydroxyethyl)-1-piperazinyl]methanone;

10-94-Cyclohexyl-benzoyl)-n-[2-(2-pyridinyl)ethyl]-10,11-dihydro-5H-pyrrolo[2,1-c][1,4]benzodiazepine-3-carboxamide;

10-(4-Cyclohexyl-benzoyl)-N-(2-pyridinylmethyl)-10,11-dihydro-5H-pyrrolo[2,1-c][1,4]benzodiazepine-3-carboxamide;

10-(4-Cyclohexyl-benzoyl)-N-(3-pyridinylmethyl)-10,11-dihydro-5H-pyrrolo[2,1-c][1,4]benzodiazepine-3-carboxamide;

10-(4-Cyclohexylbenzoyl)-N-methyl-N-[2-(2-pyridinyl)ethyl]-10,11-dihydro-5H-pyrrolo[2,1-c][1,4]benzodiazepine-3-carboxamide;

10-(4-Cyclohexyl-benzoyl)-N-(4-pyridinylmethyl)-10,11-dihydro-5H-pyrrolo[2,1-c][1,4]benzodiazepine-3-carboxamide;

[10-(4-Cyclohexyl-benzoyl)-10,11-dihydro-5H-pyrrolo[2,1-c][1,4]benzpdiazepin-3-yl][4-(4-pyridinyl)-1-piperazinyl]-methanone;

10-(4-Cyclohexyl-benzoyl)-N-methyl-N-[2(4-pyridinyl)ethyl]-10,11-dihydro-5H-pyrrolo[2,1-c][1,4]benzodiazepine-3-carboxamide;

1H-Imidazol-1-yl-[10-(4-cyclohexyl-benzoyl)-10,11-dihydro-5H-pyrrolo[2,1-c][1,4]benzodiazepin-3-yl]-methanone;

10-(4-Cyclohexyl-benzoyl)-N-methyl-N-(3-pyridinylmethyl)-10,11-dihydro-5H-pyrrolo[2,1-c][1,4]benzodiazepine-3-carboxamide It is understood by those practicing the art that some of the compounds of this invention depending on the definition of R, $R_1$, $R_2$, and $R_3$ may contain one or more asymmetric centers and may thus give rise to enantiomers and diastereomers. The present invention includes all stereoisomers including individual diastereomers and resolved, enantiomerically pure R and S stereoisomers; as well as racemates, and all other mixtures of the R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, E/Z isomers, endo-exo isomers, and mixtures thereof which possess the indicated activity. Such isomers may be obtained in pure form by standard separation procedures known to those skilled in the art. Also included in the present invention are all polymorphs and hydrates of the compounds of the present invention.

DETAILED DESCRIPTION OF THE INVENTION

The present invention comprises the compounds described above, as well as pharmaceutical compositions containing the compounds of this invention in combination or association with one or more pharmaceutically acceptable carrier or excipient. In particular, the present invention provides a pharmaceutical composition which comprises a therapeutically effective amount of one or more compounds of this invention in a pharmaceutically acceptable carrier or excipient.

This invention also comprises methods for treating conditions in a mammal, preferably a human, which are remedied or alleviated by oxytocin antagonist activity including, but not limited to, treatment, inhibition or prevention of preterm labor, dysmenorrhea and suppressing labor prior to caesarian delivery whenever desirable in a mammal, preferably in a human. The methods comprise administering to a mammal in need thereof a therapeutically effective but non-toxic amount of one or more of the compounds of this invention.

The present invention also comprises combinations of the compounds of the present invention with one or more agents useful in the treatment of disorders such as preterm labor, dysmenorrhea, and stopping labor prior to caesarian delivery. More specifically, the compounds of the present invention may be effectively administered in combination with effective amounts of other tocolytic agents used in the treatment or prevention of preterm labor, dysmenorrhea or suppressing labor prior to caesarean delivery including β-adrenergic agonists, calcium channel blockers, prostaglandin synthesis inhibitors, other oxytocin antagonists (e.g. atosiban), magnesium sulfate, ethanol, and other agents useful in the treatment of said disorders. The present invention is to be understood as embracing all simultaneous or alternating treatments of any combination of the compounds of the present invention with other tocolytic agents with any pharmaceutical composition useful for the treatment of preterm labor, dysmenorrhea, and suppressing labor prior to caesarean delivery in mammals.

The compositions are preferably adapted for intravenous (both bolus and infusion) and oral administration. However, they may be adapted for other modes of administration including subcutaneous, intraperitoneal, or intramuscular administration to a human or a farm animal in need of a tocolytic agent.

The compounds of the present invention can be used in the form of salts derived from non toxic pharmaceutically acceptable acids or bases. These salts include, but are not limited to, the following: salts with inorganic acids such as hydrochloric acid, hydrobromic acid, sulfuric acid, nitric acid, phosphoric acid and, as the case may be, such organic acids as acetic acid, oxalic acid, citric acid, tartaric acid, succinic acid, maleic acic, benzoic acid, benzene sulfonic acid, fumaric acid, malic acid, methane sulfonic acid, pamoic acid, and tosic acid. Other salts include salts with alkali metals or alkaline earth metals, such as sodium, potassium, calcium or magnesium, or with organic bases including quaternary ammonium salts. The compounds can also be used in the form of esters, carbamates and other conventional prodrug forms, which in general, will be functional derivatives of the compounds of this invention which are readily converted to the active moiety in vivo. This is meant to include the treatment of the various conditions described hereinbefore with a compound of this invention or with a compound which is not specifically disclosed but which converts to a compound of this invention in vivo upon administration. Also included are metabolites of the compounds of the present invention defined as active species produced upon introduction of these compounds into a biological system.

When the compounds of this invention are employed for the above utilities, they may be combined with one or more pharmaceutically acceptable excipients or carriers, for example, solvents, diluents and the like, and may be administered orally in such forms as tablets, capsules (including time release and sustained release formulations), pills, dispersible powders, granules, or suspensions containing, for example, from 0.05 to 5% of suspending agent, syrups containing, for example, from about 10 to 50% of sugar, and elixirs and the like, or parenterally in the form of sterile injectable solutions, suspensions or emulsions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredients employed may vary depending on the particular compound or salt employed, the mode of administration, age, weight, sex and medical condition of the patient, and the severity of the condition being treated. An ordinarily skilled physician, veterinarian or clinician can readily determine and prescribe the effective amount of the agent required to prevent, counter or arrest the progress of the condition. However, in general, satisfactory results are obtained when the compounds of the invention are administered at a daily dose of from about 0.5 to about 500 mg/Kg of mammal body weight, preferably given in divided doses two to four times a day, or in a sustained release form. For most large mammals the total daily dosage is from about 0.5 to 100 mg, preferably from 0.5 to 80 mg/Kg. Dosage forms suitable for internal use comprise from about 0.05 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, glycerol, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under conditions of manufacture and storage and must be preserved against the contaminating action of microorganisms such as bacteria and fungi. The carrier can be a solvent or dispersion medium containing, for example, water, ethanol (e.g. glycerol, propylene glycol, and liquid polyethylene glycol), suitable mixtures thereof, and vegetable oil.

Furthermore, active compounds of the present invention can be administered intranasally using vehicles suitable for intranasal delivery, or transdermally using transdermal skin patches known to those ordinarily skilled in the art. When using a transdermal delivery system, the dosage administration will be continuous rather than in a single or divided daily doses. The compounds of the present invention can also be administered in the form of liposome delivery system wherein the liposomal lipid bilayers are formed from a variety of phospholipids.

Compounds of the present invention may also be delivered by the use of carriers such as monoclonal antibodies to which the active compounds are coupled. The compounds of the present invention may also be coupled to soluble polymers as drug carriers or to biodegradable polymers useful in achieving controlled release of the active agent.

Also according to the present invention there are provided processes for producing the compounds of the present invention.

Process of the Invention

The compounds of the present invention may be prepared according to one of the general processes outlined below.

The compounds of general formula (I) wherein

$R_3$ and $R_4$ are defined hereinbefore, and R is selected from the group of —NHOR$_{31}$ wherein R$_{31}$ is as defined hereinbefore, and a, b, c (wherein v is zero), d (wherein v is zero), e, f, or i are defined hereinbefore, can be conveniently prepared as shown in Scheme I.

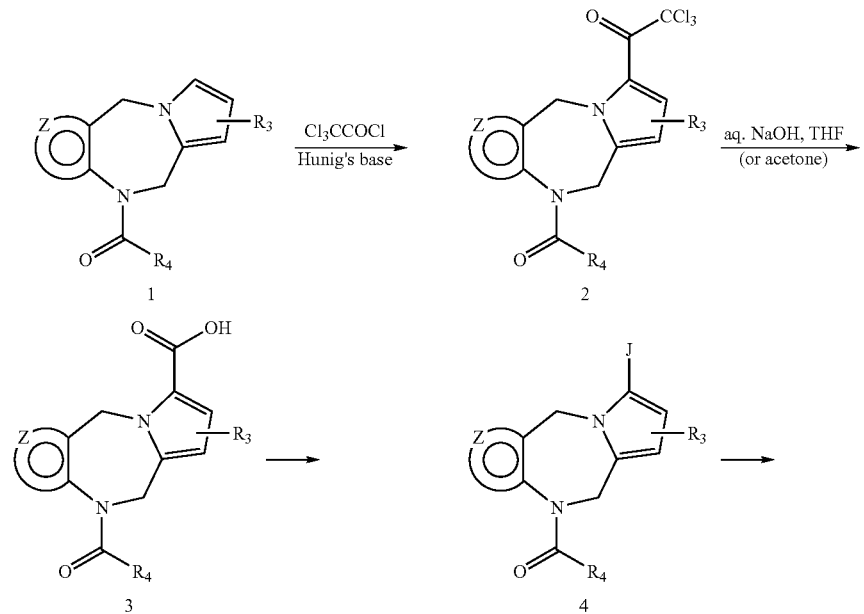

Scheme I

-continued

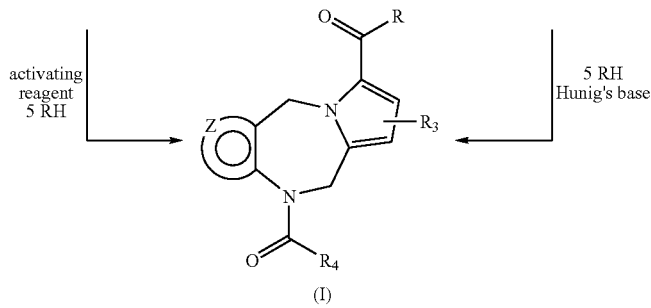

(I)

According to the above preferred process, a tricyclic diazepine of formula (1) wherein

$R_3$ and $R_4$ are defined hereinbefore, is reacted with perhaloalkanoyl halide preferable trichloroacetyl chloride in the presence of an organic base such as N,N-diisopropylethyl amine (Hünig's base) in an aprotic organic solvent such as dichloromethane at temperatures ranging from −10° C. to ambient to provide the desired trichloroacetyl intermediate of formula (2). Subsequent hydrolysis of (2) with aqueous base such as sodium hydroxide in an organic solvent such as tetrahydrofuran or acetone at temperatures ranging from −10° C. to ambient, yields the intermediate acid of formula (3). The required activation of the carboxylic acid (3) for the subsequent coupling with a primary or secondary amine, hydroxylamine or hydrazine of formula (5) can be accomplished in several ways. Thus, (3) can be converted to an acid halide preferably a chloride or bromide of formula (4, J=COCl or COBr) by reaction with thionyl chloride(bromide) or oxalyl chloride(bromide) or similar reagents known in the art, either neat or in the presence of an inorganic base such as potassium carbonate, or in the presence of an organic base such as pyridine, 4-(dimethylamino)pyridine, or a tertiary amine such as triethylamine in an aprotic solvent such as dichloromethane, N,N-dimethylformamide or tetrahydrofuran at temperatures ranging from −5° C. to 50° C. to yield the intermediate acylated derivative (4). Subsequent coupling of the acid chloride(bromide) (4, J=COCl or COBr) with an appropriately substituted primary or secondary amine, hydroxylamine or hydrazine of formula (5) in the presence of a stoichiometric amount of Hünig's base optionally in the presence of a catalytic amount of 4-(dimethylamino)pyridine, in an aprotic solvent such as dichloromethane, N,N-dimethylformamide or tetrahydrofuran at temperatures ranging from ambient to the reflux temperature of the solvent provides the desired compounds of formula (I) wherein

$R_3$ and $R_4$ are as defined hereinbefore, and R is selected from the group of —$NHOR_{31}$ wherein $R_{31}$ is as defined hereinbefore, and a, b, c (wherein v is zero), d (wherein v is zero), e, f, or i are defined hereinbefore.

Alternatively, the acylating species can be a mixed anhydride of the corresponding carboxylic acid, such as that prepared by treating said acid of formula (3) with 2,4,6-trichlorobenzoyl chloride in an aprotic organic solvent such as dichloromethane according to the procedure of Inanaga et al., Bull. Chem. Soc. Jpn. 52, 1989 (1979). Treatment of said mixed anhydride of formula (4) with an appropriately substituted primary or secondary amine, hydroxylamine or hydrazine of formula (5) in an aprotic solvent such as dichloromethane at temperatures ranging from ambient to the reflux temperature of the solvent provides the desired compounds of formula (I) wherein

R, $R_3$ and $R_4$ are as defined hereinbefore.

Alternatively, amidation of the carboxylic acids of formula (3) can be effectively carried out by treatment of said acid with triphosgene in an aprotic solvent such as dichloromethane followed by reaction of the activated intermediate with an appropriately substituted primary or secondary amine, hydroxylamine or hydrazine of formula (5) in the presence of an organic base such as Hünig's base at temperatures ranging from −10° C. to ambient.

Another preferred process for the preparation of the compounds of the present invention of formula (I) wherein

R, $R_3$ and $R_4$ are as defined hereinbefore, consists of treating the acid of formula (3) with an activating reagent such as N,N-dicyclohexylcarbodiimide or 1-ethyl-3-(3-dimethylamino-propyl) carbodiimide hydrochloride in the presence of 1-hydroxybenzotriazole followed by reaction of the activated intermediate with an appropriately substituted primary or secondary amine, hydroxylamine or hydrazine of formula (5) preferably in the presence of an organic base such as Hünig's base and a catalytic amount of 4-(dimethylamino) pyridine in an aprotic solvent such as dichloromethane, N,N-dimethylformamide or tetrahydrofuran at temperatures ranging from −10° C. to ambient.

In another preferred process, said acid (3) can be activated by treatment with other activating agents such as 1,1'- carbonyldiimidazole in an aprotic solvent such as dichloromethane or tetrahydrofuran at temperatures ranging from −10° C. to the reflux temperature of the solvent. Subsequent reaction of the intermediate activated imidazolide with an appropriately substituted primary or secondary amine, hydroxylamine or hydrazine of formula (5) provides the desired compounds of formula (I) wherein

R, $R_3$ and $R_4$ are as defined hereinbefore.

Alternatively, the coupling of the appropriately substituted primary or secondary amine of formula (5) with said acid of formula (3) can be effectively carried out by using hydroxybenzotriazole tetramethyluronium hexafluorophosphate as the coupling reagent in the presence of an organic base such as Hünig's base and in a solvent such as N,N-dimethylformamide at temperatures ranging from −10° C. to ambient to provide in good isolated yield and purity the desired compounds of formula (I) wherein

R, $R_3$ and $R_4$ are as defined hereinbefore.

Related coupling reagents such as diphenylphosphoryl azide, diethyl cyano phosphonate, benzotriazol-1-yl-oxy-tris-(dimethylamino) phosphonium hexafluorophosphate and all other reagents known in the literature that have been used in the formation of amide bonds in peptide synthesis can also be used for the preparation of compounds of formula (I) wherein

R, $R_3$ and $R_4$ are as defined hereinbefore.

As an alternative, reaction of the intermediate 3-trihalomethylketone of formula (2) directly with an appropriately substituted primary or secondary amine, hydroxylamine or hydrazine of formula (5) either in the presence or absence of a protic solvent such as ethanol at temperatures ranging from −10° C. to the reflux temperature of the solvent, also provides the desired compounds of formula (I) wherein

R, $R_3$ and $R_4$ are as defined hereinbefore.

The method of choice for the preparation of compounds of formula (I) from the intermediate carboxylic acid (3) is ultimately chosen on the basis of its compatibility with the R, $R_3$ and $R_4$ groups, and its reactivity with the tricyclic diazepine of formula (1).

Another preferred process for the preparation of (I) of Scheme I is shown in Scheme II. A tricyclic diazepine of formula (1) is reacted with diphosgene in an aprotic solvent such as dichloromethane preferably in the presence of an organic base such as triethylamine, followed by reaction of the resulting acylated intermediate with an appropriately substituted primary or secondary amine, hydroxylamine or hydrazine of formula (5) to provide the desired compounds of formula (I) wherein

R, $R_3$ and $R_4$ are as defined hereinbefore.

Scheme II

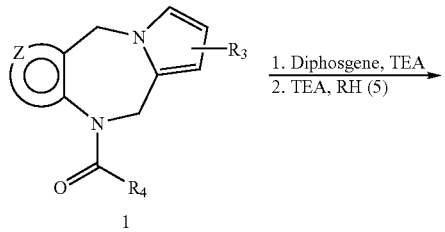

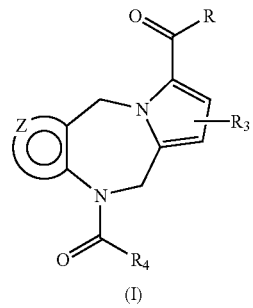

The tricyclic diazepines of formula (1) of Scheme (I) wherein $R_4$ is as defined hereinbefore, can be conveniently prepared as shown in Scheme III.

Scheme III

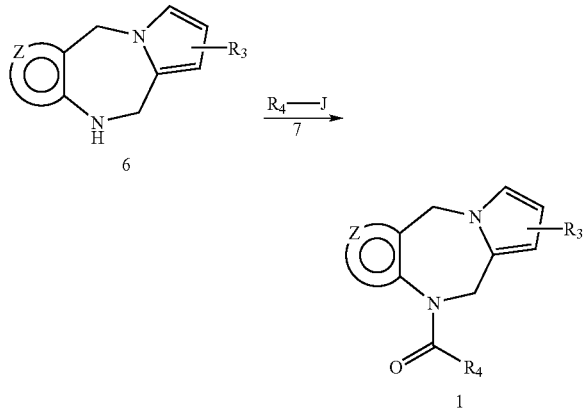

Thus, a tricyclic diazepine of formula (6) is treated with an acylating agent such as a substituted aroyl halide, preferably a substituted acyl chloride or bromide of formula (7, J=COCl or COBr) wherein $R_4$ is as defined hereinbefore, in the presence of an inorganic base such as potassium carbonate, or in the presence of an organic base such as pyridine, 4-(dimethylamino)pyridine, or a tertiary amine such as triethylamine or N,N-diisopropylethylamine in an aprotic solvent such as dichloromethane, N,N-dimethylformamide or tetrahydrofuran at temperatures ranging from −5° C. to 50° C. to provide intermediates of general formula (1) wherein

$R_3$, and $R_4$ are as defined hereinbefore.

Alternatively, the acylating species of formula (7) can be a mixed anhydride of the corresponding substituted carboxylic acid, such as that prepared by treating said acid with 2,4,6-trichlorobenzoyl chloride in an aprotic organic solvent such as dichloromethane according to the procedure of Inanaga et al., *Bull. Chem. Soc. Jpn.*, 52, 1989 (1979). Treatment of said mixed anhydride of general formula (7) with a tricyclic diazepine of formula (6) in a solvent such as dichloromethane and in the presence of an organic base such as 4-(dimethylamino)pyridine at temperatures ranging from 0° C. to the reflux temperature of the solvent, yields the intermediate acylated derivative (1) of Scheme III.

The acylating intermediate of formula (7) is ultimately chosen on the basis of its compatibility with the $R_4$ groups, and its reactivity with the tricyclic diazepine of formula (6).

A preferred process for the preparation of the desired compounds of general formula (I) of Scheme I wherein $R_4$ is as defined hereinbefore is shown in Scheme IV.

Scheme IV

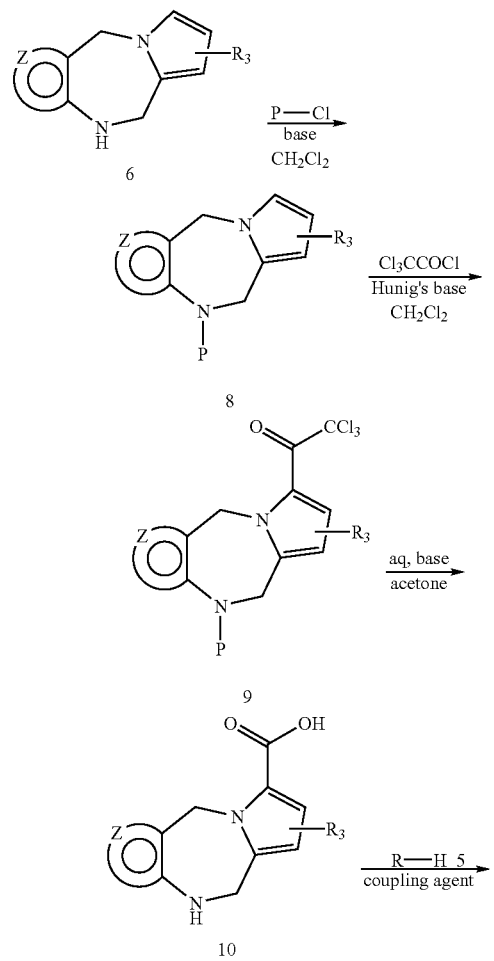

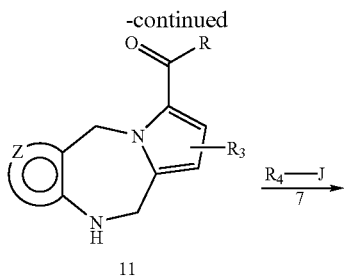

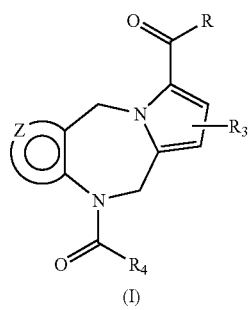

Thus, a tricyclic diazepine of formula (8) wherein

and $R_3$ are defined hereinbefore, carrying a protecting group such as a fluorenylalkoxycarbonyl group, preferably a fluorenylmethyloxycarbonyl (P=Fmoc) group, or an alkoxycarbonyl protecting group preferably a tert-butyloxycarbonyl (P=Boc) group is reacted with a perhaloalkanoyl halide preferably trichloroacetyl chloride in the presence of an organic base such as N,N-diisopropylethyl amine (Hünig's base) or a tertiary amine such as triethylamine optionally in the presence of catalytic amounts of 4-(dimethylamino) pyridine in an aprotic organic solvent such as dichloromethane at temperatures ranging from −10° C. to ambient to provide the desired trichloroacetyl intermediate of formula (9). Subsequent hydrolysis of the trichloroacetyl group with aqueous base such as sodium hydroxide in an organic solvent such as acetone or tetrahydrofuran at temperatures ranging from −10° C. to ambient, is accompanied by simultaneous removal of the protecting group and yields the intermediate acid of formula (10). The required amidation of the carboxylic acid (10) can be effectively accomplished by treating (10) with an activating reagent such as N,N-dicyclohexylcarbodiimide or 1-ethyl-3-(3-dimethylamino-propyl) carbodiimide hydrochloride in the presence of 1-hydroxybenzotriazole followed by reaction of the activated intermediate with an appropriately substituted primary or secondary amine of formula (5) preferably in the presence of Hünig's base or a catalytic amount of 4-dimethylamino) pyridine in an aprotic solvent such as dichloromethane, N,N-dimethylformamide or tetrahydrofuran at temperatures ranging from −10° C. to ambient.

Other coupling reagents known in the literature that have been used in the formation of amide bonds in peptide synthesis can also be used for the preparation of compounds of formula (11) wherein

R and R₃ are as defined hereinbefore. The method of choice for the preparation of compounds of formula (11) from the intermediate carboxylic acid (10) is ultimately chosen on the basis of its compatibility with the

and R₃ groups, and its reactivity with the tricyclic diazepine of formula (6). Subsequent reaction of a tricyclic diazepine amide (11) with an acylating agent of formula (7) provides the desired compounds of formula (I) wherein

R, and R₃ and R₄ are defined hereinbefore.

Alternatively, the intermediate acids of formula (10) of Scheme IV wherein

and R₃ are defined hereinbefore, can be obtained by reacting a tricyclic diazepine of formula (6) with an excess of the acylating agent preferably trifluoroacetic anhydride or trichloroacetyl chloride in the presence of an inorganic base such as potassium carbonate or an organic base such as N,N-diisopropylethyl amine in an aprotic solvent such as N,N-dimethylformamide followed by basic hydrolysis of the intermediate bis-trifluoroacetyl (trichloroacetyl) intermediate of formula (12 X=F or Cl) preferably with aqueous sodium hydroxide in a protic organic solvent such as ethanol at temperatures ranging from ambient to the reflux temperature of the solvent as exemplified in Scheme V.

Scheme V

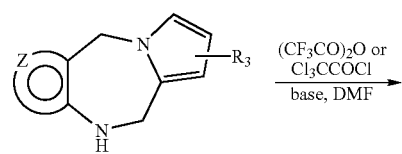

The tricyclic diazepines of formula (6) of Scheme III wherein

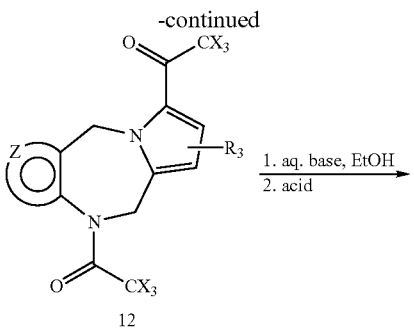

and R₃ are as defined hereinbefore, are conveniently prepared according to Scheme VI by condensation of a pyrrolo-2-carboxaldehyde with an appropriately substituted 2-nitro benzyl bromide (13) followed by reductive cyclization in the presence of tin(II) chloride in acid medium and catalytic hydrogenation of the intermediate imine also in acidic medium.

Scheme VI

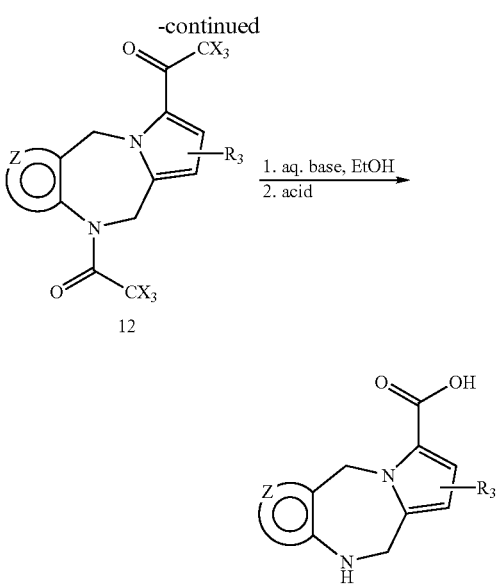

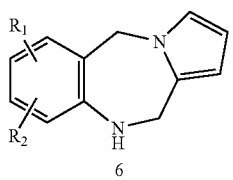

The compounds of general formula (I) wherein

, $R_3$ and $R_4$ are as defined hereinbefore and R is selected from the j group, wherein $R_{27}$ is $NHR_{38}$ wherein $R_{38}$ is defined hereinbefore, are conveniently prepared as shown in Scheme VII and VIII below.

Scheme VII

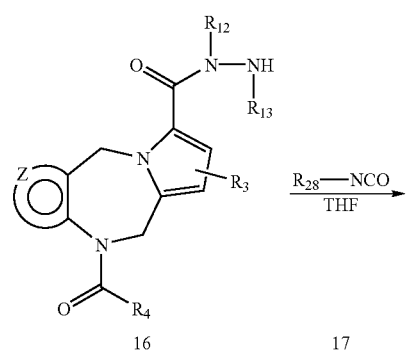

Thus, an appropriately substituted hydrazide of formula 16, wherein

, $R_3$, and $R_4$ are as defined hereinbefore, and R is selected from the group i defined hereinbefore wherein $R_{14}$ is hydrogen, is reacted with a substituted isocyanate of formula 17 wherein $R_{38}$ is defined hereinbefore, in an aprotic solvent such as tetrahydrofuran, at temperatures ranging from ambient to the reflux temperature of the solvent to provide the desired compound of formula (I) wherein

, $R_3$ and $R_4$ are as defined hereinbefore and R is selected from the j group, wherein $R_{27}$ is —$NHR_{38}$ and $R_{38}$ is defined hereinbefore.

Alternatively, the compounds of general formula (I) wherein

, $R_3$ and $R_4$ are as defined hereinbefore and R is selected from the j group, wherein $R_{27}$ is $R_{28}$ and $R_{28}$ is defined hereinbefore, are conveniently prepared by acylation of the hydrazide of formula 16, wherein $R_3$ and $R_4$, are as defined hereinbefore and R is selected from the group i defined hereinbefore wherein $R_{14}$ is hydrogen, with an alkanoyl, cycloalkanoyl or optionally substituted aroyl halide (18, preferably J=COCl) in an organic base such as pyridine, at temperatures ranging from ambient to the reflux temperature of the solvent, as shown in Scheme VIII below. Alternatively, the acylating agent 18 can be a carboxylic acid anhydride (such as acetic anhydride) also in pyridine.

Scheme VIII

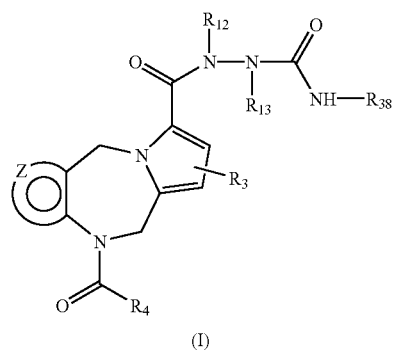

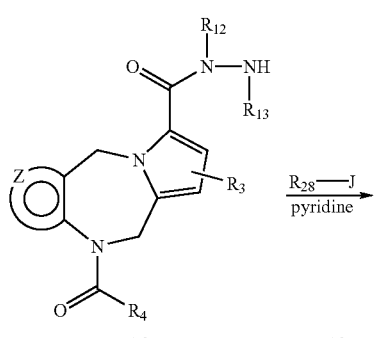

The compounds of general formula (I) wherein $R_3$ and $R_4$ are as defined hereinbefore and R is selected from the h group defined hereinbefore are conveniently prepared by treatment of the hydrazide of formula 19 wherein

, $R_3$ and $R_4$ are defined hereinbefore, and R is selected from the group i defined hereinbefore wherein $R_{13}$ and $R_{14}$ are hydrogen, with a di(lower alkyl)amide di(lower alkyl)acetal preferably N,N-dimethylformamide dimethyl acetal or N,N-dimethylacetamide dimethyl acetal of formula 20 without additional solvents, at temperatures ranging from ambient to the reflux temperature of the reagents, as shown in Scheme IX.

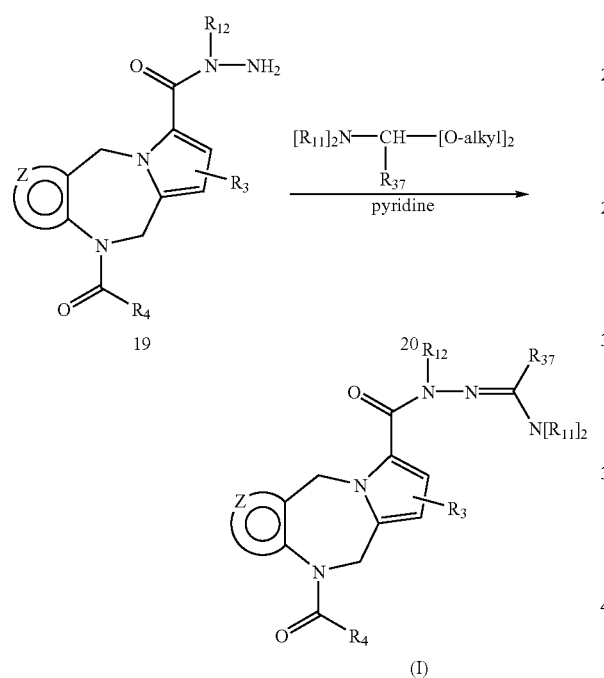

In a similar process the compounds of general formula (I) wherein $R_3$ and $R_4$ are as defined hereinbefore and R is selected from the g group defined hereinbefore are conveniently prepared by treatment of the carboxamide (21) wherein $R_3$ and $R_4$ are as defined hereinbefore and R is selected from the group a wherein $R_5$ and $R_6$ are both hydrogen, with a di(lower alkyl)amide di(lower alkyl)acetal, preferably N,N-dimethylformamide dimethyl acetal, or N,N-dimethylacetamide dimethyl acetal, of formula 20 without additional solvents, at temperatures ranging from ambient to the reflux temperature of the reagents, as shown in Scheme X.

The compounds of general formula (I) wherein $R_3$ and $R_4$ are as defined hereinbefore and R is $-CH=CH-N[R_{32}]_2$ and $R_{32}$ is defined hereinbefore, are conveniently prepared by enamination of the tricyclic diazepine ketone of formula 22 with a tert-butoxy-bis(di-lower-alkylamino)methane preferably tert-butoxy-bis(dimethylamino)methane (Bredereck's reagent, *J. Heterocycl. Chem.*, 28, 1043 (1991); *Tet. Lett.*, 31, 2105 (1990)) of formula 23, in an aprotic solvent such as dichloromethane, at temperatures ranging from ambient to the reflux temperature of the solvent, as shown in Scheme XI.

-continued

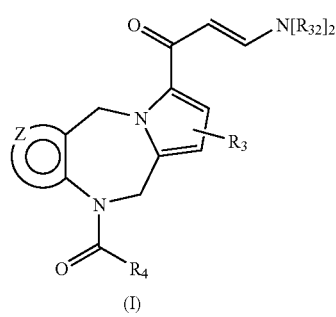

Finally, the compounds of general formula (I) wherein

$R_3$ and $R_4$ are defined hereinbefore, and R is selected from the c and d groups defined hereinbefore wherein v is 1, can be conveniently prepared as shown in Scheme XII by treatment of the tricyclic diazepine of formula (1) with oxalyl chloride in an aprotic solvent such as dichloromethane, followed by treatment of the activated intermediate with a secondary amine of formula (5), at temperatures ranging from ambient to the reflux temperature of the solvent.

Scheme XII

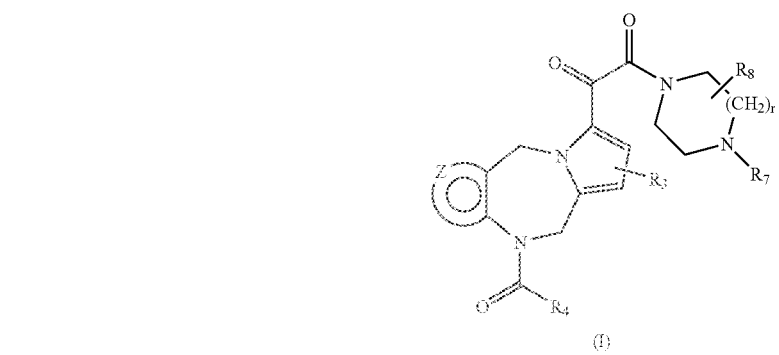

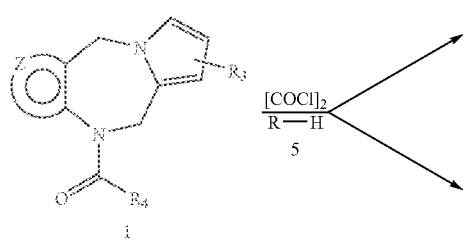

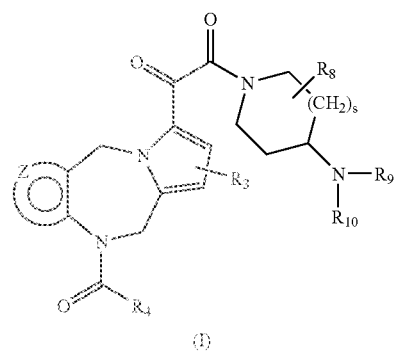

The subject compounds of the present invention were tested for biological activity according to the following procedures.

Vasopressin Binding in Chinese Hamster Ovary Cell Membranes Expressing Human Vasopressin $V_{1a}$ Subtype Receptors Receptor Source:

Chinese hamster ovary cells (CHO cells) stably transfected with the human vasopressin $V_{1a}$ subtype receptors were either obtained from Biosignal Inc., 1744 rue Williams, Montreal, Quebec, Canada or obtained from M. Thibonnier, Case Western Reserve University School of Medicine, Cleveland, Ohio.

A. Passaging and Amplification of Cells:

CHO cells transfected with the human vasopressin $V_{1a}$ subtype receptors obtained from M. Thibonnier (pZeoSV vector) are allowed to grow to confluency (approx. >90%) in T-150 flasks under sterile conditions, in a cell culture medium of F-12 Nutrient Mixture (HAM) with L-glutamine (Gibco Cat. # 11765-054) containing 15 mM HEPES (Gibco Cat. 15630-080), 1% antibiotic/antimycotic (add 5 mL 100×, Gibco Cat. 15240-062 per 500 mL F-12), 250 µg/mL Zeocin (add 1.25 mL of 100 mg/mL Invitrogen R-250-01 per 500 mL F-12) and 10% Fetal Bovine Serum (Qualified, heat inactivated, Gibco Cat. # 16140-063). The medium is removed by aspiration and the cells are washed with 10 mL of Hank's Balanced Salt solution (Gibco Cat. # 14175-095). The salt solution is removed by aspiration and the cells are trypsinized with 5 mL of trypsin-EDTA (0.05% trypsin, 0.53 mM EDTA-4Na, Gibco Cat. # 25300-070) for 1 min. The trypsin is removed by aspiration and the cells dislodged by tapping. Cell Culture medium (eg, 30 mL for 1:30 split) is immediately added and mixed well to inactivate trypsin. 1 mL of detached cells is added to new culture flasks containing fresh cell culture medium (eg, into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g,. use 10 mL per T-150 flask). The excess is removed and the cells are bathed for 15–30 min. in an enzyme-free Cell Dissociation Buffer (e.g. use 8 mL Hank's Based, Gibco Cat. # 13150-016 per T-150 flask) until the cells are loosened. The contents are transferred to centrifuge tubes (50 mL) kept in an ice bath. All subsequent steps are done at 4° C. The tubes are centrifuged at 300×g for 15 min (1380 rpm on SORVAL, Model RT6000D, using rotor for the 50 mL tubes). The supernatant is discarded and the cells suspended in homogeneizing buffer(10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogenizer and homogenized with 3 strokes. The homogenate is centrifuged at 1500× g for 10 min at 4° C. (3100 rpm using SORVAL, model RT6000D, using the rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 µL (to make up a final volume of 200 µL) of assay buffer containing 50 mM of Tris-HCl (pH 7.4), BSA (heat inactivated, protease-free), 0.1% of 5 mM $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 µL of unlabeled Manning ligand (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. 20 µL of 50% DMSO is added for Manning and other peptide ligands and the assay buffer volume is adjusted accordingly. To each well is added 50 µL of frozen membrane suspension thawed immediately prior to use and diluted in the assay buffer to the required concentration (equivalent to 25 to 50 µg of protein/well as needed). 20 µL of 8 nM [$^3$H]Manning ligand in the assay buffer, prepared just before use, is added, and incubated at room temperature for 60 min. shaking the plate on a mechanical shaker for the first 15 min. The incubation is stopped by rapid filtration of the the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Vasopressin Binding in Chinese Hamster Ovary Cell Membranes Expressing Human Vasopressin $V_2$ Subtype Receptors Receptor Source:

Chinese Hamster Ovary (CHO) cells stably transfected with the human $V_2$ subtype receptors were obtained from M. Thibonnier, Case Western Reserve University School of Medicine, Cleveland, Ohio.

A. Passaging and Amplification of Cells:

CHO cells transfected with the human vasopressin $V_2$ subtype receptors obtained from M. Thibonnier (pZeoSV vector) are allowed to grow to confluency (approx. >90%) in T-150 flasks under sterile conditions, in a cell culture medium of F-12 Nutrient Mixture (HAM) with L-glutamine (Gibco Cat. # 11765-054) containing 15 mM HEPES (Gibco Cat. # 15630-080), 1% antibiotic/antimycotic (add 5 mL 100×, Gibco Cat. # 15240-062 per 500 mL F-12), 250 µg/mL Zeocin (add 1.25 mL of 100 mg/mL Invitrogen R-250-01 per 500 mL F-12) and 10% Fetal Bovine Serum (Qualified, heat inactivated, Gibco Cat. # 16140-063). The medium is removed by aspiration and the cells washed with 10 mL of Hank's Balanced Salt solution (Gibco Cat. # 14175-095). The salt solution is removed by aspiration and the cells trypsinized with 5 mL of trypsin-EDTA (0.05% trypsin, 0.53 mM EDTA-4Na, Gibco Cat. # 25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 day interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g. use 10 mL per T-150 flask). The excess solution is removed and the cells bathed for 15–30 min. in an enzyme-free Cell Dissociation Buffer (e.g. use 8 mL Hank's Based, Gibco Cat. # 13150-016 per T-150 flask) until cells are loosened. The contents are transferred to centrifuge tubes (50 mL) kept in an ice bath. All subsequent steps are done at 4° C. The tubes are centrifuged at 300× g for 15 min (1380 rpm on SORVAL, Model RT6000D, using the rotor for 50 mL tubes). The supernatant is discarded and the cells suspended in homogeneizing buffer(10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with a Polytron at setting 6 for 10 sec. The homogenate is transferred into a Potter-Elvjehm homogeneizer and homogenized with 3 strokes. The homogenate is centrifuged at 1500×g for 60 min at 4° C. (3100 rpm using SORVAL, model RT6000D, using the rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernantant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 μL of unlabeled arginine vasopressin (AVP) (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For vasopressin and other peptide ligands 20 μL of 50% DMSO is added and the assay buffer volume is adjusted accordingly.

To each well is added 50 μL of frozen membrane suspension thawed immediately prior to use and diluted in assay buffer to the required concentration (equivalent to 25 to 50 μg of protein/well as needed). 20 μL of 8 nM[$^3$H]arginine vasopressin (AVP) ligand in the assay buffer, prepared just before use is added and incubated at room temperature for 60 min. shaking the plate on a mechanical shaker for the first 15 min. The incubation is stopped by rapid filtration of the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Oxytocin Binding in Chinese Hamster Ovary Cell Membranes Expressing Human Oxytocin Receptors Receptor Source:

Chinese Hamster Ovary (CHO) cells stably transfected with the human oxytocin receptor (cf. Tanizawa et al., U.S. Pat. No. 5,466,584 (1995) to Rohto Pharmaceutical Co. Ltd., Osaka, Japan) were obtained from M. Thibonnier, Case Western Reserve University School of Medicine, Cleveland, Ohio.

A. Passaging and Amplification of Cells:

CHO cells transfected with the human oxytocin receptors obtained from M. Thibonnier (pcDNA3.1 vector) are allowed to grow to confluency (approx. >90%) in T-150 flasks under sterile conditions, in a cell culture medium of F-12 Nutrient Mixture (HAM) with L-glutamine (Gibco Cat. # 11765-054) containing 15 mM HEPES (Gibco Cat. # 15630-080), 1% antibiotic/antimycotic (add 5 mL 100×, Gibco Cat. # 15240-062 per 500 mL F-12), 400 μg/mL of Geneticin (add 4 mL of 50 mg/mL per 500 mL F-12) and 10% Fetal Bovine Serum (Qualified, heat inactivated, Gibco Cat. # 16140-063). The medium is removed by aspiration and the cells are washed with 10 mL of Hank's Balanced Salt solution (Gibco Cat. # 14175-095). The salt solution is removed by aspiration and the cells trypsinized with 5 mL of trypsin-EDTA (0.05% trypsin, 0.53 mM EDTA-4Na, Gibco Cat. # 25300-070) for 1 min The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation:

The cells are washed twice gently with Hank's Balanced Salt solution (eg, use 10 mL per T-150 flask). The excess solution is removed and the cells bathed for 15–30 min. in an enzyme-free Cell Dissociation Buffer (eg, use 8 mL Hank's Based, Gibco Cat. # 13150-016 per T-150 flask) until cells are loosened. The contents are transferred to centrifuge tubes (50 mL size) kept in ice bath. All subsequent steps are done at 4° C. The tubes are centrifuged at 300×g for 15 min (1380 rpm on SORVAL, Model RT6000D, using rotor for 50 mL tubes). The supernatant is discarded and the cells suspended in homogenizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with a Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using rotor for 50 mL tubes).

The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 µL (to make up a final volume of 200 µL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 µL of unlabeled oxytocin (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For oxytocin and other peptide ligands, 20 µL of 50% DMSO is added and the assay buffer volume is adjusted accordingly.

To each well is added 50 µL of frozen membrane suspension thawed immediately prior to use and diluted in assay buffer to the required concentration (equivalent to 25 to 50 µg of protein/well as needed). 20 µL of 8 nM [$^3$H]oxytocin in the assay buffer, prepared just before use is added and incubated at room temperature for 60 min. shaking the plate on a mechanical shaker for the first 15 min. The incubation is stopped by rapid filtration of the the plate contents followed by washing with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Binding data is either reported as percent inhibition at a certain concentration or if an $IC_{50}$ was calculated, as a nanomolar concentration. The results of these tests on representative compounds of this invention are shown in Table 1.

TABLE 1

Binding to membranes of Chinese Hamster Ovary (CHO) cell line stably transfected with human vasopressin $V_{1a}$ receptor subtype, human $V_2$ vasopressin receptor subtype and human oxytocin receptor

| Example | OT % inhibition at 100 nM ($IC_{50}$, nM)* | $V_{1a}$ % inhibition at 100 nM ($IC_{50}$, nM)* | $V_2$ % inhibition at 100 nM ($IC_{50}$, nM)* |
|---|---|---|---|
| 1 | 14 | −7 | 3 |
| 3 | −2 | −19 | −4 |
| 5 | 46 | 3 | 2 |
| 6 | (104.7) | (258) | (>1000) |
| 7 | 12 | 4 | 10 |
| 8 | (126.79) | (542.72) | (>1000) |
| 9 | (35.43) | (146.3) | (>1000) |
| 10 | (75.73) | (365.56) | (1162) |
| 11 | (52.1) | (367.18) | (>1000) |
| 12 | 47 | 31 | 7 |

TABLE 1-continued

Binding to membranes of Chinese Hamster Ovary (CHO) cell line stably transfected with human vasopressin $V_{1a}$ receptor subtype, human $V_2$ vasopressin receptor subtype and human oxytocin receptor

| Example | OT % inhibition at 100 nM ($IC_{50}$, nM)* | $V_{1a}$ % inhibition at 100 nM ($IC_{50}$, nM)* | $V_2$ % inhibition at 100 nM ($IC_{50}$, nM)* |
|---|---|---|---|
| 13 | 73 | 35 | 18 |
| 14 | 53 | 23 | 4 |
| 15 | 16 | −4 | 11 |
| 16 | (132.87) | (376.83) | (>1000) |
| 17 | (51.36) | (306.42) | (476.89) |
| 18 | (4.36) | (87.54) | (293.72) |
| 19 | (130.1) | (879.7) | (>1000) |
| 20 | 43 | 21 | 11 |
| 21 | 68 | 21 | 13 |
| 22 | 34 | 13 | 19 |
| 23 | (41.77) | (634.93) | (>1000) |
| 24 | (18.3) | (202.91) | (>1000) |
| 25 | (13.25) | (90.36) | (>1000) |
| 26 | (19.71) | (199.66) | (>1000) |
| 27 | 44 | 6 | 9 |
| 28 | (111.21) | (>1000) | (>1000) |
| 29 | 42 | 2 | 8 |
| 30 | 94 | 49 | 15 |
| 31 | 89 | 69 | 2 |
| 32 | 87 | 56 | 6 |
| 33 | 66 | 27 | 14 |
| 34 | −5 | 3 | 17 |
| 35 | 55 | 12 | 16 |
| 36 | 13 | 3 | 1 |
| 37 | 61 | 23 | 8 |
| 38 | 57 | 31 | 1 |
| 39 | 85 | 43 | 13 |
| 40 | 60 | 22 | −3 |
| 41 | 31 | 14 | 6 |
| 42 | 65 | 28 | 4 |
| 43 | 1 | 1 | 8 |
| 44 | 2 | 1 | 1 |
| 45 | 71 | 31 | 10 |
| 46 | 91 | 21 | 14 |
| 47 | 82 | 28 | 0 |
| 48 | 78 | 35 | 14 |
| 49 | −2 | 0 | 10 |
| 50 | −8 | 3 | 15 |
| 51 | −8 | −1 | 7 |
| 52 | 45 | 19 | 8 |
| 53 | 25 | 20 | 2 |
| 54 | 4 | 0 | 6 |
| 55 | 91 | 50 | 6 |
| 56 | 61 | 16 | −2 |
| 57 | −4 | −5 | 4 |

*Binding in Chinese Hamster Ovary cell membranes expressing human vasopressin $V_{1a}$ and $V_2$ subtype receptors, and human oxytocin receptors The following examples are presented to illustrate rather than limit the scope of this invention.

EXAMPLE 1

Methyl 10-(4-cyclohexylbenzoyl)-3-[(4-methyl-1-piperazinyl)carbonyl]-10,11-dihydro-5H-pyrrolo[2,1-c][1,4]benzodiazepine-8-carboxylate hydrochloride salt Step A. [4-(2-Formyl-1H-pyrrole-1-yl)methyl]-3-nitro]-benzoic acid methyl ester To a suspension of sodium hydride (8.1 g, 60% suspension in oil) in N,N-dimethylformamide (25 mL) was added dropwise over 15 minutes a solution of pyrrole 2-carboxaldehyde (9.1 g, 1 equiv.) in N,N-dimethylformamide (25 mL). After the addition, the reaction mixture was stirred for 30 minutes and then cooled to 0° C. A solution of 4-bromomethyl-2-nitrobenzoic acid (25.0 g, 1 equiv.) in N,N-dimethylformamide (50 mL) was added dropwise over 20 minutes. After the addition, the reaction mixture was stirred at room temperature for 1 hour and then iodomethane (1.2 eq.) was added. The mixture was stirred at room temperature overnight and diluted with water (200 mL). The solid was filtered, washed with water and dried over anhydrous potassium carbonate in vacuo at 50° C. to provide the crude title compound as a brown solid (26 g), which was used as such in the next step.

Step B. 10,11-Dihydro-5H-pyrrolo[2,1-c][1,4]benzodiazepine-8-carboxylic acid methyl ester To a stirred solution of tin(II) chloride dihydrate (23 g, 3.5 equiv.) in 2 N hydrochloric acid (106 mL) was added the [4-(2-formyl-1H-pyrrole-1-yl)methyl]-3-nitro]-benzoic acid methyl ester of Step A (8 g). Methanol (200 mL) was then added and the reaction mixture was stirred at 40° C. for 2 hours. The reaction was then cooled to room temperature, quenched by the addition of saturated aqueous sodium carbonate (20 mL) and filtered through Celite. The filter pad was washed with methanol and hot ethyl acetate. The filtrate and washings were combined, concentrated in vacuo to a volume of 300 mL and extracted with ethyl acetate. The combined extracts were dried over anhydrous magnesium sulfate, filtered and concentrated in vacuo to a volume of 200 mL. Acetic acid (1 g) and 10% palladium on charcoal (1.5 g) were added and the mixture was hydrogenated overnight at atmospheric pressure. The reaction was then filtered through Celite and the solvent removed in vacuo to give a dark brown crystalline solid (16.4 g). This was dissolved in dichloromethane and filtered through a silica gel pad eluting with dichloromethane to provide the title compound which was recrystallized from 1,2-dichloroethane to yield a yellow crystalline solid (5.7 g), m.p. 198–200° C.

$^1$H NMR (CDCl$_3$, 200 MHz): δ 3.95 (s, 3H), 4.50 (s, 2H), 5.20 (s, 2H), 6.05 (t, 2H), 6.70 (t, 1H), 7.05 (d, 1H), 7.15 (s, 1H), 7.20 (d, 1H), 7.30 (s, 1H).

Step C. Methyl 10-(4-cyclohexylbenzoyl)-10,11-dihydro-5H-pyrrolo[2,1-c][1,4]benzodiazepine-8-carboxylate To a solution of 10,11-dihydro-5H-pyrrolo[2,1-c][1,4]benzodiazepine-8-carboxylic acid methyl ester of Step B (9.9 mmol) in 1,2-dichloroethane (25 mL) was added 4-cyclohexyl benzoyl chloride (1.1 equiv.) and triethylamine (2.5 equiv.) and the mixture was stirred at room temperature overnight. The solvent was then removed in vacuo and the residue chromatographed on silica gel eluting with 5% ethyl acetate in petroleum ether to provide the title compound as a white crystalline solid, m.p. 174–176° C.

$^1$H NMR (DMSO-d$_6$, 400 MHz): δ 1.20 (m, 1H), 1.30 (t, 4H), 1.65 (d, 3H), 1.75 (d, 2H), 2.40 (m, 1H), 3.70 (s, 3H), 5.20 (br, 2H), 5.35 (br, 2H), 5.90 (m, 2H), 6.82 (t, 1H), 7.08 (d, 2H), 7.19 (d, 2H), 7.40 (s, 1H), 7.60 (d, 1H), 7.74 (dd, 1H).

Anal. Calcd. for C$_{27}$H$_{28}$N$_2$O$_3$: C, 75.68; H, 6.59; N, 6.54. Found: C, 75.13; H, 6.58; N, 6.54.

MS [(+)APCI, m/z]: 429 [M+H]$^+$. Calcd. for C$_{27}$H$_{29}$N$_2$O$_3$: 429.2178

Step D. Methyl 10-(4-cyclohexyl-benzoyl)-3-[(4-methyl-1-piperazinyl)carbonyl]-10,11-dihydro-5H-pyrrolo[2,1-c][1,4]benzodiazepine-8-carboxylate hydrochloride salt A solution of methyl 10-(4-cyclohexylbenzoyl)-10,11-dihydro-5H-pyrrolo[2,1-c][1,4]benzodiazepine-8-carboxylate of Step C (3.38 mmol) in dichloromethane (20 mL) was treated with diphosgene (1.1 equiv.) and triethylamine (1.5 equiv.) and stirred at room temperature overnight. The solvent was then removed in vacuo and the residue was dissolved in dichloromethane (20 mL), and then treated with triethylamine (1.5 equiv) and 1-methylpiperazine (1.5 equiv). The reaction mixture was washed with water, dried over anhydrous magnesium sulfate, filtered and evaporated to dryness. The residue was first chromatographed on silica gel eluting with 2% methanol in dichloromethane, and then chromatographed again eluting with 2% methanol in ethyl acetate to provide the title compound as a white crystalline solid, m.p. 166–168° C. This was converted to the hydrochloride salt by treatment of the free base in anhydrous ethanol with anhydrous hydrogen chloride in dioxane (1.1 equiv.). The salt so obtained was a white crystalline solid, m.p. 203° C. (dec.).

$^1$H NMR (DMSO-d$_6$, 400 MHz): δ 1.25 (m, 1H), 1.30 (t, 4H), 1.70 (m, 5H), 2.40 (m, 1H), 2.80 (s, 3H), 3.20 (br, 2H), 3.40 (br, 4H), 3.70 (s, 3H), 4.40 (br, 2H), 5.15 (br, 2H), 5.50 (s, 2H), 6.10 (d, 1H), 6.40 (d, 1H), 7.05 (d, 2H), 7.15 (d, 2H), 7.30 (s, 1H), 7.60 (d, 1H), 7.70 (d, 1H), 10.40 (br, 1H).

Anal. Calcd. for C$_{33}$H$_{38}$N$_4$O$_4$+HCl+H$_2$O: C, 65.07; H, 6.78; N, 9.20; Found: C, 64.68; H, 6.71; N, 8.91.

MS [EI, m/z]: 554 [M]$^+$. Calcd. for C$_{33}$H$_{38}$N$_4$O$_4$: 554.6794.

EXAMPLE 2

10-(4-Cyclohexylbenzoyl)-10,11-dihydro-5H-pyrrolo[2,1-c][1,4]benzodiazepine-8-carboxylic acid sodium salt To a stirred solution of the methyl 10-(4-cyclohexylbenzoyl)-10,11-dihydro-5H-pyrrolo[2,1-c][1,4]benzodiazepine-8-carboxylate of Example 1, Step C (0.200 g) in anhydrous ethanol (2 mL) was added 2.5 N sodium hydroxide (1 equiv.). The reaction mixture was stirred for three days at room temperature and the solvent removed in vacuo to provide the title compound as a pale-yellow hygroscopic solid after drying over phosphorus pentoxide at 60° C.

$^1$H NMR (DMSO-d$_6$, 400 MHz): δ 1.20 (m, 1H), 1.39 (t, 4H), 1.70 (m, 5H), 2.40 (m, 1H), 5.20 (br, 4H), 5.90 (m, 2H), 6.80 (t, 1H), 7.05 (d, 2H), 7.20 (d, 2H), 7.35 (d, 2H), 7.64 (dd, 1H).

Anal. Calcd. for C$_{26}$H$_{25}$N$_2$O$_3$Na+1.5H$_2$O: C, 67.38; H, 6.09; N, 6.04. Found: C, 67.14; H, 5.9; N, 5.93.

MS [(+)ESI, m/z]: 415 [M+H]$^+$. Calcd. for C$_{26}$H$_{27}$N$_2$O$_3$: 415.2022.

EXAMPLE 3

10-(4-Cyclohexyl-benzoyl)-3-[(4-methyl-1-piperazinyl)carbonyl]-10,11-dihydro-5H-pyrrolo[2,1-c][1,4]benzodiazepine-8-carboxylic acid To a solution of the methyl 10-(4-cyclohexylbenzoyl)-3-[(4-methyl-1-piperazinyl)carbonyl]-10,11-dihydro-5H-pyrrolo[2,1-c][1,4]benzodiazepine-8-carboxylate of Example 1, Step D (1.1 g, 1.93 mmol) in ethanol (10 mL) was added 2.5 N sodium hydroxide (1.5 equiv.) and the reaction mixture was stirred overnight at room temperature. The solution was neutralized by the addition of one equivalent of 2 N hydrochloric acid and the solvent was removed in vacuo. The residue was extracted with dichloromethane, filtered and the solvent removed in vacuo. The residue was then chromatographed on silica gel eluting with 10% methanol in dichloromethane to provide the title product as a white crystalline solid, m.p. 195–210° C.

$^1$H NMR (DMSO-d$_6$, 400 MHz): δ 1.20 (m, 1H), 1.30 (t, 4H), 1.70 (m, 5H), 2.20 (s, 3H), 2.30 (s, 4H), 2.40 (m, 1H), 3.40 (br, 2H), 3.60 (t, 2H), 5.15 (br, 2H), 5.40 (s, 2H), 6.15 (d, 1H), 6.20 (d, 1H), 7.05 (d, 2H), 7.15 (d, 2H), 7.30 (s, 1H), 7.50 (d, 1H), 7.65 (d, 1H).

Anal. Calcd. for $C_{32}H_{36}N_4O_4+H_2O$: C, 68.80; H, 6.86; N, 10.03. Found: C, 68.27; H, 6.72; N, 9.95.

MS [(−)ESI, m/z]: 539 [M−H]$^−$. Calcd. for $C_{32}H_{35}N_4O_4$: 539.2658.

EXAMPLE 4

10-(4-Cyclohexyl-benzoyl)-10,11-dihydro-5H-pyrrolo[2,1-c][1,4]benzodiazepine

4-Cyclohexylbenzoic acid (0.50 g, 2.45 mmol) was suspended in thionyl chloride (3 mL) and heated at reflux for 30 minutes. After cooling, the thionyl chloride was removed in vacuo. The residue was dissolved in toluene and concentrated in vacuo to give the crude acid chloride as a yellow oil which was then dissolved in dichloromethane (5 mL) and slowly added to a solution of 10,11-dihydro-5H-pyrrolo[2,1-c][1,4]benzodiazepine (0.67 g, 3.64 mmol) and N,N-diisopropylethyl amine (0.94 mL, 5.4 mmol) in dichloromethane (15 mL). After stirring for 2 hours, the reaction was quenched with water. The organic layer was washed with 1 N hydrochloric acid, 1 N sodium hydroxide and brine, dried over anhydrous sodium sulfate, filtered and concentrated in vacuo to give a yellow oil. Purification by flash chromatography using a solvent system of 50% dichloromethane in hexane followed by 25% ethyl acetate in hexane gave a white foam which crystallized upon sonication from hexane/ethyl acetate to provide the title compound (0.60 g) as a white solid, m.p. 127–129° C.

NMR (DMSO-d$_6$, 400 MHz): δ 1.15–1.32 (m, 5H), 1.64–1.74 (m, 5H), 2.39–2.42 (m, 1H), 4.80–5.40 (broad s, 4H), 5.91–5.94 (m, 2H), 6.81 (t, 1H), 6.90 (d, 1H), 7.05–7.11 (m, 3H), 7.15–7.19 (m, 3H), 7.45–7.47 (m, 1H).

Anal. Calcd. for $C_{25}H_{26}N_2O+0.05\ C_4H_8O_2$: C, 80.74; H, 7.10; N, 7.47. Found: C, 80.36; H, 7.11; N, 7.53.

MS [EI, m/z]: 370 [M]$^+$. Calcd. for $C_{25}H_{26}N_2O$: 370.4868.

EXAMPLE 5

[4-(tert-Butyl)phenyl][10-(4-cyclohexyl-benzoyl)-10,11-dihydro-5H-pyrrolo[2,1-c][1,4]benzodiazepin-3-yl]methanone A mixture of 10-(4-cyclohexyl-benzoyl)-10,11-dihydro-5H-pyrrolo[2,1-c][1,4]benzodiazepine of Example 4 (1.85 g), dry xylene (25 mL) and 4-tert-butylbenzoylchloride (1.97 g) was refluxed overnight. The reaction mixture was poured into water, washed with saturated aqueous sodium bicarbonate, dried over anhydrous sodium sulfate and filtered through a short column of Magnesol®. After eluting with several additional volumes of dichloromethane, the combined eluate was refluxed with the gradual addition of hexane until crystallization was noted. Cooling and trituration provided the desired title product (0.18 g) as off-white crystals, m.p. 143–145° C.

Anal. Calc'd for $C_{36}H_{38}N_2O_2$: C, 81.48; H, 7.22; N, 5.28. Found: C, 81.84; H, 7.21; N, 5.18.

MS [(+)ESI, m/z]: 531 [M+H]$^+$. Calc'd for $C_{36}H_{39}N_2O_2$: 531.3012.

EXAMPLE 6

1-[10-(4-Cyclohexyl-benzoyl)-10,11-dihydro-5H-pyrrolo[2,1-c][1,4]benzodiazepin-3-yl]-ethanone Step A. 1-[10-(4-Cyclohexyl-benzoyl)-10,11-dihydro-5H-pyrrolo[2,1-c][1,4]benzodiazepine-3-carbaldehyde 10-(4-Cyclohexyl-benzoyl)-10,11-dihydro-5H-pyrrolo[2,1-c][1,4]benzodiazepine of Example 4 (1.065 g) in dichloromethane (50 mL) was reacted with formic acetic anhydride. After stirring at room temperature overnight, the reaction mixture was washed with water and saturated aqueous sodium bicabonate, dried over anhydrous sodium sulfate and evaporated to dryness. The residue was filtered through a short column of Magnesol® to provide the desired title compound which was used as such in the next step.

Step B. 1-[10-(4-Cyclohexyl-benzoyl)-10,11-dihydro-5H-pyrrolo[2,1-c][1,4]benzodiazepin-3-yl]-ethanone 10-(4-Cyclohexylbenzoyl)-10,11-dihydro-5H-pyrrolo[2,1-c][1,4]benzodiazepine-3-carbaldehyde of Step A (3.7 g) dissolved in dichloromethane (75 mL) was treated with acetyl chloride (1.9 g) and tin (IV) chloride in dichloromethane (12.5 mL, 1N). After stirring overnight at room temperature, water was added. The organic solution was washed with saturated aqueous sodium bicarbonate, dried over anhydrous sodium sulfate and filtered through a short column of Magnesol® to provide the desired title compound as a pale yellow amorphous solid (1.3 g).

MS [(+)ESI, m/z]: 413 [M+H]$^+$. Calcd. for $C_{27}H_{29}N_2O_2$: 413.2229.

EXAMPLE 7

2,2,2-Trichloro-1-[10-(4-cyclohexyl-benzoyl)-10,11-dihydro-5H-pyrrolo[2,1-c][1,4]benzodiazepin-3-yl]-1-ethanone To a solution of 10-(4-cyclohexylbenzoyl)-10,11-dihydro-5H-pyrrolo[2,1-c][1,4]benzodiazepine of Example 4 (1.85 g) in dichloromethane (50 mL) was added trichloroacetyl chloride (1 g). After stirring overnight at room temperature, the mixture was washed with saturated aqueous sodium bicarbonate, dried over anhydrous sodium sulfate, and filtered through a short column of Magnesol®. After eluting with several additional volumes of dichloromethane, the eluate was combined and refluxed with gradual addition of hexane until crystallization was observed. The title compound (1.5 g) was obtained upon cooling, as colorless crystals, m.p. 172–174° C.

Anal. Calcd. for $C_{27}H_{25}Cl_3N_2O_2$: C, 62.86; H, 4.88; N, 5.43; Cl, 20.62. Found: C, 62.79; H, 4.64; N, 5.47; Cl, 20.25.

MS [(+) ESI, m/z]: 516.9 [M+H]$^+$. Calcd. for $C_{27}H_{26}Cl_3N_2O_2$: 516.1138

EXAMPLE 8

10-(4-Cyclohexy-benzoyl)-10,11-dihydro-5H-pyrrolo[2,1-c][1,4]benzodiazepine-3-carboxylic acid hydrazide 2,2,2-Trichloro-1-[10-cyclohexyl-benzoyl]10,11-dihydro-5H-pyrrolo[2,1-c][1,4]benzodiazepin-3-yl]-1-ethanone of Example 7 (1.3 g) was added to a solution of anhydrous hydrazine (0.24 g) in absolute ethanol (50 mL). After stirring overnight at room temperature, the volatiles were removed in vacuo and the residue extracted with dichloromethane.

The combined extracts were dried over anhydrous sodium sulfate and filtered through a short column of Magnesol®. Removal of the solvent provided the title compound as a pale yellow amorphous solid.

Anal. Calcd. for $C_{26}H_{28}N_4O_2$: C, 72.87; H, 6.59; N, 13.07. Found: C, 72.28; H, 6.67; N, 12.84.

MS [(+)ESI, m/z]: 429.1 [M+H]$^+$. Calcd. for $C_{26}H_{29}N_4O_2$: 429.2291.

EXAMPLE 9

N'-{[10-(4-Cyclohexyl-benzoyl)-10,11-dihydro-5H-pyrrolo[2,1-c][1,4]benzodiazepin-3-yl]carbonyl}-N,N-dimethylethanehydrazonamide A stirred mixture of 10-(4-cyclohexyl-benzoyl)-10,11-dihydro-5H-pyrrolo[2,1-c][1,4]benzodiazepine-3-carboxylic acid hydrazide of Example 8 (0.50 g) and N,N-dimethylacetamide dimethyl acetal (5 mL) was refluxed for one hour and then evaporated to dryness under reduced pressure. The residue was dissolved in dichloromethane, washed with aqueous saturated sodium chloride, dried over anhydrous sodium sulfate and filtered through a short column of Magnesol®. After eluting with several additional volumes of dichloromethane, the combined eluate was evaporated to provide the title compound as a light tan amorphous solid, m.p. 164–175° C.

MS [(+)ESI, m/z]: 498.2 [M+H]$^+$. Calcd. for $C_{30}H_{36}N_6O_2$: 498.2869.

EXAMPLE 10

N'-{[10-(4-Cyclohexyl-benzoyl)-10,11-dihydro-5H-pyrrolo[2,1-c][1.4]benzodiazepin-3-yl]carbonyl}-N,N-dimethylhydrazonoformamide A mixture of 10-(4-cyclohexylbenzoyl)-10,11-dihydro-5H-pyrrolo[2,1-c][1,4]benzodiazepine-3-carboxylic acid hydrazide of Example 8 (1 g) and N,N-dimethylformamide dimethyl acetal (10 mL) was refluxed for four hours. All volatiles were removed in vacuo and the residue was dissolved in dichloromethane and filtered through a short column of Magnesol®. Removal of the solvent in vacuo provided the title compound as a colorless amorphous solid, m.p. 167–190° C.

MS [(+)ESI, m/z]: 484.1 [M+H]$^+$. Calcd. for $C_{29}H_{34}N_5O_2$: 484.2713

EXAMPLE 11

N'-Acetyl-10-(4-cyclohexyl-benzoyl)-10,11-dihydro-5H-pyrrolo[2,1-c][1,4]benzodiazepine-3-carbonyl-hydrazide To a solution of 10-(4-cyclohexyl-benzoyl)-10,11-dihydro-5H-pyrrolo[2,1-c][1.4]benzodiazepin-3-carboxylic acid hydrazide of Example 8 (1.01 g) in pyridine (10 mL) was added acetic anhydride (0.25 g). After stirring overnight at room temperature, the mixture was poured into water and extracted with dichloromethane. The extracts were dried over anhydrous sodium sulfate and filtered through a short column of Magnesol®. Removal of all volatiles in vacuo provided the title compound as a pale yellow amorphous solid (0.26 g).

MS [(+)ESI, m/z]: 471 [M+H]$^+$. Calcd. for $C_{29}H_{31}N_4O_3$: 471.2396.

EXAMPLE 12

10-(4-Cyclohexyl-benzoyl)-N'-(2-methylbenzoyl)-10,11-dihydro-5H-pyrrolo[2,1-c][1,4]benzodiazepine-3-carbonyl-hydrazide To a solution of 10-(4-cyclohexyl-benzoyl)-10,11-dihydro-5H-pyrrolo[2,1-c][1.4]benzodiazepin-3-carboxylic acid hydrazide of Example 8 (1.07 g) in pyridine (10 mL) was added o-toluoyl chloride (0.50 g). After stirring at room temperature overnight, the reaction mixture was washed with water and saturated aqueous sodium bicarbonate, and dried over anhydrous sodium sulfate. The solution was filtered though a short column of Magnesol®. After eluting with several additional volumes of dichloromethane, the combined eluate was refluxed with the gradual addition of hexane until crystallization occurred. The title compound (0.57 g) was obtained upon cooling and filtering as colorless crystals, m.p. 156–158° C.

Anal. Calcd. for $C_{34}H_{34}N_4O_3$: C, 74.70; H, 6.27; N, 10.25. Found: C, 74.91; H, 6.48; N, 10.19.

MS [(+)ESI, m/z]: 547.2 [M+H]$^+$, 564.3 [M+NH$_4$]$^+$. Calcd. for $C_{34}H_{35}N_4O_3$: 547.2709.

EXAMPLE 13

10-(4-Cyclohexyl-benzoyl)-N'-(cyclopropylcarbonyl)-10,11-dihydro-5H-pyrrolo[2,1-c][1,4]benzodiazepine-3-carbonyl-hydrazide To a solution of 10-(4-cyclohexyl-benzoyl)-10,11-dihydro-5H-pyrrolo[2,1-c][1.4]benzodiazepin-3-carboxsylic acid hydrazide of Example 8 (1.07 g) in dry pyridine (10 mL) was added dropwise under stirring cyclopropylcarbonyl chloride (0.3 g). After overnight stirring at room temperature the mixture was poured into water and extracted with dichloromethane. The combined extracts were dried over anhydrous sodium sulfate and the solution filtered through a short column of Magnesol®. After elution with several additional volumes of dichloromethane, the combined eluate was evaporated to dryness to provide the title compound as a colorless amorphous solid (0.38 g).

Anal, Calcd. for $C_{30}H_{32}N_4O_3$: C, 72.56; H, 6.49; N, 11.28. Found: C, 72.34; H, 6.60; N, 11.07.

MS [(+)ESI, m/z]: 497.1 [M+H]$^+$. Calcd. for $C_{30}H_{33}N_4O_3$: 497.2553.

EXAMPLE 14

10-(4-Cyclohexyl-benzoyl)-N'-(3-methyl-benzoyl)-10,11-dihydro-5H-pyrrolo[2,1-c][1,4]benzodiazepine-3-carbonyl-hydrazide To a solution of 10-(4-cyclohexyl-benzoyl)-10,11-dihydro-5H-pyrrolo[2,1-c][1.4]benzodiazepin-3-carboxylic acid hydrazide of Example 8 (2.14 g) in dry pyridine (20 mL) was added dropwise under stirring m-toluoyl chloride (1 g). After overnight stirring at room temperature the mixture was poured into water and extracted with dichloromethane. The combined extracts were dried over anhydrous sodium sulfate and the solution filtered through a short column of Magnesol®. After elution with several additional volumes of dichloromethane, the combined eluate was evaporated to dryness to provide the title compound as a colorless amorphous solid (2.1 g).

Anal. Calcd for $C_{34}H_{34}N_4O_3$: C, 74.70; H, 6.27; N, 10.25. Found: C, 74.22; H, 6.61; N, 10.14.

MS [(+)ESI, m/z]: 547.11 [M+H]$^+$, 569.0 [M+Na]$^+$. Calcd for $C_{34}H_{35}N_4O_3$: 547.2709.

EXAMPLE 15

2-{[10-(4-Cyclohexyl-benzoyl)-10,11-dihydro-5H-pyrrolo[2,1-c][1,4]benzodiazepin-3-yl]carbonyl}-N-phenyl-1-hydrazinecarboxamide A mixture of 10-(4-cyclohexyl-benzoyl)-10,11-dihydro-5H-pyrrolo[2,1-c][1,4]benzodiazepin-3-carboxylic acid hydrazide of Example 8 (0.56 g) and phenylisocyanate (0.17 g) in tetrahydrofuran (25 mL) was refluxed under stirring for four hours. After removal of all volatiles at reduced pressure, the residue was treated with water and extracted with dichloromethane. The combined extracts were dried over anhydrous sodium sulfate and the solution filtered through a short column of Magnesol®. After elution with several additional volumes of dichloromethane, the combined eluate was evaporated to dryness to provide the title compound as a yellow amorphous solid (0.18 g).

Anal. Calcd. for $C_{33}H_{33}N_5O_3$: C, 72.37; H, 6.07; N, 12.24. Found: C, 71.90; H, 6.23; N, 12.50.

MS [(+)ESI, m/z]: 548.1 [M+H]$^+$, 565.1 [M+NH$_4$]$^+$. Calcd. for $C_{33}H_{33}N_5O_3$: 548.2662.

EXAMPLE 16

10-(4-Cyclohexyl-benzoyl)-10,11-dihydro-5H-pyrrolo[2,1-c][1,4]benzodiazepin-3-carboxamide 2,2,2-Trichloro-1-[10-cyclohexyl-benzoyl)-pyrrolo[2,1-c][1,4]benzodiazepin-3-yl]-1-ethanone of Example 7 (0.60 g) was added to a pressure flask containing concentrated ammonium hydroxide (25 mL) and absolute ethanol (25 mL). The mixture was heated in an oil bath held at 110° C. for four hours. On cooling the title compound crystallized out and was filtered off to provide colorless crystals (0.66 g), m.p. 122–123° C.

Anal. Calcd. for $C_{26}H_{27}N_3O_2+0.25H_2O$: C, 74.70; H, 6.71; N, 10.05. Found: C, 74.83; H, 6.52; N, 9.71.

MS [(+)ESI, m/z]: 414.1 [M+H]$^+$. Calcd. for $C_{26}H_{28}N_3O_2$: 414.2182.

EXAMPLE 17

10-(4-Cyclohexyl-benzoyl)-N-[(E)-(dimethylamino)methylidene-10,11-dihydro-5H-pyrrolo[2,1-c][1,4]benzodiazepine-3-carboxamide 10-(4-Cyclohexyl-benzoyl)-10,11-dihydro-5H-pyrrolo[2,1-c][1,4]benzodiazepine-3-carboxamide of Example 16 (0.50 g) and N,N-dimethylformamide dimethyl acetal (10 mL) were refluxed for several hours. All volatiles were removed at reduced pressure and the residue dissolved in dichloromethane. The solution was washed with saturated aqueous sodium bicarbonate, dried over anhydrous sodium sulfate and filtered through a short column of Magnesol®. Hexane was gradually added to the refluxing solution until crystallization was noted. On cooling the desired title compound was obtained as colorless crystals (0.45 g), m.p. 216–218° C.

Anal. Calcd. for $C_{29}H_{32}N_4O_2$: C, 74.33; H, 6.88; N, 11.96. Found: C, 73.58; H, 6.92; N, 11.55.

MS [(+)ESI, m/z]: 469.9 [M+H]$^+$. Calcd. for $C_{29}H_{33}N_4O_2$: 469.2604.

EXAMPLE 18

10-(4-Cyclohexyl-benzoyl)-N-[(E)-1-(dimethylamino)ethylidene-10,11-dihydro-5H-pyrrolo[2,1-c][1,4]benzodiazepine-3-carboxamide A mixture of 10-(4-cyclohexyl-benzoyl)-10,11-dihydro-5H-pyrrolo[2,1-c][1,4]benzodiazepine-3-carboxamide of Example 16 (0.57 g) and N,N-dimethylacetamide dimethyl acetal (10 mL) was refluxed for six hours. All volatiles were removed under reduced pressure and the residue dissolved in dichloromethane. The solution was washed with water and saturated aqueous sodium bicarbonate, dried over anhydrous sodium sulfate and filtered through a short column of Magnesol®. After eluting with several additional volumes of dichloromethane, the combined eluate was evaporated to dryness. The title compound (0.20 g) crystallized upon addition of hexane, m.p. 128–131° C.

Anal. Calcd. for $C_{30}H_{34}N_4O_2$: C, 74.66; H, 7.10; N, 11.61. Found: C, 74.57; H, 7.30; N, 11.50.

MS [(+)ESI, m/z]: 483.1 [M+H]$^+$. Calcd. for $C_{30}H_{34}N_4O_2$: 483.2760.

EXAMPLE 19

10-(4-Cyclohexyl-benzoyl)-N'-N'-dimethyl-10,11-dihydro-5H-pyrrolo[2,1-c][1,4]benzodiazepine-3-carbohydrazide A mixture of 2,2,2-trichloro-1-[10-(cyclohexylbenzoyl)-10,11-dihydro-5H-pyrrolo[2,1-c][1,4]benzodiazepin-3-yl]-1-ethanone of Example 7 (0.52 g) and 1,1-dimethylhydrazine (1.0 mL) was stirred for several days. The yellow solid was collected, dissolved in dichloromethane and the solution filtered through a short column of Magnesol®. The eluate was refluxed with the gradual addition of hexane until crystallization occurred. The title compound (0.42 g) was recovered by filtration as yellow crystals, m.p. 182–183° C.

Anal. Calcd. for $C_{28}H_{32}N_4O_2$: C, 73.46; H, 7.06; N, 12.27. Found: C, 73.28; H, 7.36; N, 12.06.

MS [(+)ESI, m/z]: 457.3 [M+H]$^+$. Calcd. for $C_{28}H_{32}N_4O_2$: 457.2604.

EXAMPLE 20

(E)-1-[10-(4-Cyclohexyl-benzoyl)-10,11-dihydro-5H-pyrrolo[2,1-c][1,4]benzodiazepin-3-yl]-3-(dimethylamino)-2-propen-1-one A mixture of 1-[10-(4-cyclohexylbenzoyl)-10,11-dihydro-5H-pyrrolo[2,1-c][1,4]benzodiazepin-3-yl]-ethanone of Example 6 Step B (1.0 g), tert-butoxybis(dimethylamino)methane (5 mL) and dichloromethane (25 mL) was refluxed for six hours and then allowed to stir at room temperature overnight. All volatiles were then removed at reduced pressure and the residue was dissolved in dichloromethane. The solution was washed with water, dried over anhydrous sodium sulfate and filtered through a short column of Magnesol®. The eluate was refluxed with the gradual addition of hexane to provide pale yellow crystals of the title compound (0.16 g), m.p. 237–240° C.

MS [(+)ESI, m/z]: 468.2 [M+H]$^+$. Calcd. for $C_{30}H_{34}N_3O_2$: 468.2651.

EXAMPLE 21

10-(4-Cyclohexyl-benzoyl)-N-methyl-10,11-dihydro-5H-pyrrolo[2,1-c][1,4]benzodiazepine-3-carboxylic acid hydrazide A solution of 2,2,2-trichloro-1-[(10-cyclohexyl-benzoyl)-10,11-dihydro-5H-pyrrolo[2,1-c][1,4]benzodiazepin-3-yl]-1-ethanone of Example 7 (2.32 g) in absolute ethanol (50 mL) was treated with methylhydrazine (0.626 g). The mixture was refluxed for four hours and then all volatiles were removed in vacuo. The residue was treated with water and extracted with dichloromethane. The extracts were filtered through a short column of Magnesol®. The eluate was evaporated to dryness to provide the title compound as an amorphous yellow solid (0.18 g).

MS [EI, m/z]: 443.0 [M]$^+$. Calcd. for $C_{27}H_{31}N_4O_2$: 443.2447.

EXAMPLE 22

10-(4-Cyclohexyl-benzoyl)-10,11-dihydro-5H-pyrrolo[2,1 c][1,4]benzodiazepine-3-carboxylic acid 2,2,2-Trichloro-1-[(10-cyclohexylbenzoyl)-10,11-dihydro-5H-pyrrolo[2,1-c][1,4]bernzodiazepin-3-yl]-ethanone of Example 7 (5.83 g) was added to a mixture of acetone (100 mL) and 2.5 N sodium hydroxide (8.5 mL). The reaction mixture was refluxed for one hour and then evaporated to dryness. Water was added to the residue and the solution was extracted with dichloromethane. The aqueous layer was acidified with glacial acetic acid and evaporated to dryness. The residual oil crystallized to provide the title compound as a light tan solid (3.03 g), m.p. 193–194° C.

Anal. Calcd. for $C_{26}H_{26}N_2O_3$: C, 75.34; H, 6.32; N, 6.76. Found: C, 75.23; H, 6.19; N, 6.59.

MS [(+)ESI, m/z]: 415.3 [M+H]$^+$. Calcd. for $C_{26}H_{27}N_2O_3$: 415.2022.

EXAMPLE 23

[10-(4-Cyclohexyl-benzoyl)-10,11-dihydro-5H-pyrrolo[2,1-c]1,4]benzodiazepin-3-yl][4-(2-pyrimidinyl)-1-piperazinyl]methanone To a stirred suspension of 10-(4-cyclohexy-benzoyl)-10,11-dihydro-5H-pyrrolo[2,1-c][1,4]benzodiazepine-3-carboxylic acid of Example 22 (3.14 g) in dichloromethane (25 mL) was added oxalyl chloride (3.0 g). The reaction mixture was stirred for five hours at room temperature and then evaporated to dryness. The crude acid chloride thus obtained (1 g) was dissolved in dichloromethane (25 mL) and treated with 2-piperazinyl pyrimidine hydrochloride (0.87 g), N,N-diisopropylethyl amine (0.78 g) and 4-(dimethylamino)pyridine (0.05 g). After stirring overnight at room temperature, the mixture was washed with water and saturated aqueous sodium bicarbonate, The organic phase was dried over anhydrous sodium sulfate and the solution was filtered through a short column of Magnesol®. Evaporation of the solvent provided the title compound (0.62 g) as pale yellow amorphous solid.

MS [(+)ESI, m/z]: 561.1 [M+H]$^+$. Calcd. for $C_{34}H_{37}N_6O_2$: 561.2978.

EXAMPLE 24

[10-(4-Cyclohexyl-benzoyl)-10,11-dihydro-5H-pyrrolo[2,1-c][1,4]benzodiazepin-3-yl](4-methyl-1-piperazinyl)-methanone To a stirred suspension of 10-(4-cyclohexyl-benzoyl)-10,11-dihydro-5H-pyrrolo[2,1-c][1,4]benzodiazepine-3-carboxylic acid of Example 22 (3.14 g) in dichloromethane (25 mL) was added oxalyl chloride (3.0 g). The reaction mixture was stirred for five hours at room temperature and then evaporated to dryness. The crude acid chloride thus obtained was dissolved in dichloromethane (50 mL) and added to a mixture of N,N-diisopropylethyl amine (1.0 g) and N-methyl piperazine (1.52 g) in dichloromethane (50 mL). The mixture was stirred at room temperature overnight, then washed with water and saturated aqueous sodium bicarbonate. The solution was dried over anhydrous sodium sulfate and then filtered through a short column of Magnesol®. Removal of the solvent followed by the addition of diethyl ether provided the title compound (2.50 g) as a pale yellow solid, m.p. 134–136° C.

Anal. Calcd. for $C_{31}H_{36}N_4O_2$: C, 74.97; H, 7.31; N, 11.28. Found: C, 75.10; H, 7.11; N, 11.34.

MS [(+)ESI, m/z]: 497.0 [M+H]$^+$. Calcd. for $C_{31}H_{36}N_4O_2$: 497.2917.

EXAMPLE 25

[10-(4-Cyclohexyl-benzoyl)-10,11-dihydro-5H-pyrrolo[2,1-c][1,4]benzodiazepin-3-yl][4-(1-pyrrolidinyl)-1-piperidinyl]methanone A stirred solution of the crude 10-(4-cyclohexyl-benzoyl)-10,11-dihydro-5H-pyrrolo[2,1-c][1,4]benzodiazepine-3-carbonyl chloride (prepared in the manner of Example 23, from 1 g of the corresponding carboxylic acid of Example 22) in dichloromethane (25 mL) was treated with 4-(1-pyrrolidinyl) piperidine (0.74 g), N,N-diisopropylethyl amine (0.31 g) and 4-(dimethylamino)pyridine (0.05 g). The reaction mixture was stirred at room temperature overnight, washed with water and saturated aqueous sodium bicarbonate and dried over anhydrous sodium sulfate. Filtration of this solution through a short column of Magnesol® gave a pale yellow eluate which was evaporated to dryness to provide the title compound as a pale yellow amorphous material (0.42 g).

MS [(+)ESI, m/z]: 551.2 [M+H]$^+$. Calcd. for $C_{35}H_{43}N_4O_2$: 551.3386.

EXAMPLE 26

[1,4']Bipiperidinyl-1'-yl-[10-(4-cyclohexyl-benzoyl)-10,11-dihydro-5H-pyrrolo[2,1-c][1,4]benzodiazepin-3-yl]-methanone A stirred suspension of 10-(4-cyclohexyl-benzoyl)-10,11-dihydro-5H-pyrrolo[2,1-c][1,4]benzodiazepine-3-carboxylic acid of Example 22 (1.0 g) in dichloromethane (25 mL) was treated with oxalyl chloride (1.0 g) followed by one drop of N,N-dimethylformamide. After stirring at room temperature for four hours the volatiles were removed at reduced pressure to give the crude acid chloride (1.03 g) which was used in the next step without further purification.

The crude acid chloride was dissolved in dichloromethane (25 mL) and the solution treated with N,N-diisopropylethyl amine (0.16 g), 4-(dimethylamino)pyridine (0.05 g) and 4-(1-piperidino)piperidine (0.29 g). After stirring overnight at room temperature, the reaction mixture was washed with water and saturated aqueous sodium bicarbonate and dried over anhydrous sodium sulfate. The solution was filtered through a short column of Magnesol® and the eluate refluxed with the gradual addition of hexane to provide the title compound as a pale yellow amorphous solid (0.068 g).

MS [(+) ESI, m/z]: 565.2 [M+H]$^+$.Calcd. for $C_{36}H_{45}N_4O_2$: 565.3543.

EXAMPLE 27

[10-(4-Cyclohexyl-benzoyl)-10,11-dihydro-5H-pyrrolo[2,1-c][1,4]benzodiazepin-3-yl][4-(2-methylphenyl)-1-piperazinyl]-methanone The crude 10-(4-cyclohexyl-benzoyl)-10,11-dihydro-5H-pyrrolo[2,1-c][1,4]benzodiazepine-3-carbonyl chloride prepared in the manner of Example 23 (0.5 g) was added to a stirred mixture of N,N-diisopropylethyl amine (0.47 g), 4-(2-toluoyl)piperazine hydrochloride (0.51 g) and 4-(dimethylamino)pyridine (0.05 g) in dichloromethane (25 mL). After stirring overnight at room temperature the reaction mixture was washed with water and saturated aqueous sodium bicarbonat, and dried over anhydrous sodium sulfate. The solution was filtered through a short column of Magnesol®. Refluxing the eluate with the gradual addition of hexane resulted in crystallization of the desired title compound (0.46 g) as colorless crystals, m.p. 141–143° C.

MS [(+)ESI, m/z]: 573.2 [M+H]$^+$. Calcd. for $C_{37}H_{41}N_4O_2$: 573.3230.

EXAMPLE 28

[10-(4-Cyclohexyl-benzoyl)-10,11-dihydro-5H-pyrrolo[2,1-c][1,4]benzodiazepine 3-yl][4-(2-pyridinyl)-1-piperazinyl]-methanone The crude 10-(4-cyclohexyl-benzoyl)-10,11-dihydro-5H-pyrrolo[2,1-c][1,4]benzodiazepine-3-carbonyl chloride prepared in the manner of Example 23 (0.5 g) was added to a stirred mixture of N,N-diisopropylethyl amine (0.32 g), 4-(2-pyridyl)piperazine (0.39 g) and 4-(dimethylamino)pyridine (0.05 g) in dichloromethane (25 mL). After stirring overnight at room temperature the reaction mixture was washed with water and saturated aqueous sodium bicarbonate, and dried over anhydrous sodium sulfate. The solution was filtered through a short column of Magnesol®. and the eluate evaporated to dryness to provide the desired title compound (0.30 g) as a pale yellow amorphous solid.

MS [(+)ESI, m/z]: 560.2 [M+H]$^+$. Calcd. for $C_{35}H_{38}N_5O_2$: 560.3026.

EXAMPLE 29

10-(4-Cyclohexyl-benzoyl)-10,11-dihydro-5H-pyrrolo[2,1-c][1,4]benzodiazepine-3-carboxylic acid (4-methoxy-phenyl)-amide The crude 10-(4-cyclohexyl-benzoyl)-10,11-dihydro-5H-pyrrolo[2,1-c][1,4]benzodiazepine-3-carbonyl chloride prepared in the manner of Example 23 (1.0 g) was added to a stirred mixture of N,N-diisopropylethyl amine (0.31 g) and 4-methoxy aniline (0.35 g) in dichloromethane (25 mL). After stirring overnight at room temperature the reaction mixture was washed with water and saturated aqueous sodium bicarbonate, and dried over anhydrous sodium sulfate. The solution was filtered through a short column of Magnesol® and the eluate evaporated to dryness to provide the desired title compound (1.0 g) as an off-white amorphous solid.

Anal. Calcd. for $C_{33}H_{33}N_3O_3$: C, 76.28; H, 6.40; N, 8.09. Found: C, 75.63; H, 6.53; N, 7.62.

EXAMPLE 30

[10-(4-Cyclohexyl-benzoyl)-10,11-dihydro-5H-pyrrolo[2,1-c][1,4]benzodiazepin-3-yl](4-methyl-[1,4]-diazepan-1-yl)-methanone The crude 10-(4-cyclohexyl-benzoyl)-10,11-dihydro-5H-pyrrolo[2,1-c][1,4]benzodiazepine-3-carbonyl chloride (prepared from 2.5 g of the corresponding acid of Example 22, in the manner of Example 23) was added to a stirred mixture of N,N-diisopropylethyl amine (1.73 g), 4-(dimethylamino)pyridine (0.1 g) and N-methyl homopiperazine (1.52 g) in dichloromethane (25 mL). After stirring overnight at room temperature the reaction mixture was washed with water and saturated aqueous sodium bicarbonate, and dried over anhydrous sodium sulfate. The solution was filtered through a short column of Magnesol® and the eluate refluxed with the slow addition of hexane to provide the title compound as off-white crystals (0.46 g), m.p. 133–136° C.

Anal. Calcd. for $C_{32}H_{38}N_4O_2$: C, 75.26; H, 7.50; N, 10.97. Found: C, 75.31; H, 7.56; N, 10.81.

MS [(+)ESI, m/z]: 511.1 [M+H]$^+$. Calcd. for $C_{32}H_{38}N_4O_2$: 511.3073.

EXAMPLE 31

1-[1.4']Bipiperidinyl-1'-yl-2-[10-(4-cyclohexyl-benzoyl)-10,11-dihydro-5H-pyrrolo[2,1-c][1,4]benzodiazepin-3-yl]-ethane-1,2-dione To a stirred solution of 10-(4-cyclohexyl-benzoyl)-10,11-dihydro-5H-pyrrolo[2,1-c][1,4]benzodiazepine of Example 4 (1.0 g) in dichloromethane (20 mL) was added oxalyl chloride (0.34 g). The reaction mixture was allowed to stir at room temperature for three hours, and then 4-(1-piperidino) piperidine (0.91 g) was added. After stirring overnight at room temperature, the mixture was washed with water and saturated aqueous sodium bicarbonate and dried over anhydrous sodium sulfate. The solution was filtered through a short column of Magnesol® and the eluate refluxed with the slow addition of hexane to provide the title compound as pale pink crystals (0.43 g), m.p. 190–195° C.

Anal, Calcd. for $C_{37}H_{44}N_4O_3$: C, 74.97; H, 7.48; N, 9.45. Found: C, 74.63; H, 7.41; N, 9.28.

MS [(+)ESI, m/z]: 593.2 [M+H]$^+$. Calcd. for $C_{37}H_{45}N_4O_3$: 593.3492.

EXAMPLE 32

1-[10-(4-Cyclohexyl-benzoyl)-10,11-dihydro-5H-pyrrolo[2,1-c][1,4]benzodiazepin-3-yl]-2-(4-methyl-1-piperazin-1-yl)-1,2-ethane-1,2-dione To a stirred solution of 10-(4-cyclohexyl-benzoyl)-10,11-dihydro-5H-pyrrolo[2,1-c][1,4]benzodiazepine of Example 4 (1.0 g) in dichloromethane (20 mL) was added oxalyl chloride (0.38 g) followed a short time later by N-methylpiperazine (0.54 g). The reaction mixture was stirred overnight at room temperature, then washed with water and saturated aqueous sodium bicarbonate, and dried over anhydrous sodium sulfate. The solution was filtered through a short column of Magnesol®. After eluting with several additional volumes of dichloromethane, the combined eluate was refluxed with the gradual addition of hexane until crystallization occurred. The title compound (0.85 g) was obtained as colorless crystals, m.p. 135–137° C.

Anal. Calcd. for $C_{32}H_{36}N_4O_3$: C, 73.26; H, 6.92; N, 10.68. Found: C, 72.81; H, 7.12; N, 10.36.

MS [(+)ESI, m/z]: 525.1 [M+H]$^+$. Calcd. for $C_{32}H_{37}N_4O_3$: 525.2866.

The following examples were prepared according to one of the general procedures (A–D) shown below.

General Procedure A

Triphosgene (742 mg, 2.5 mmol) was added to a stirred solution of 10-(4-cyclohexyl-benzoyl)-10,11-dihydro-5H-pyrrolo[2,1-c][1,4]benzodiazepine-3-carboxylic acid of Example 22 (5.0 mmol) in dichloromethane (10 mL). The clear solution was allowed to stir at room temperature (14 hours) after which time the solution turned red. To the reaction mixture was added a solution of the required amine (10.0 mmol) and N,N-diisopropylethyl amine (10.0 mmol) in dichloromethane (5 mL). The mixture was diluted with dichloromethane and washed with water and brine. The organic phase was dried, filtered and concentrated to afford a brown foam which was purified by flash chromatography on silica gel. The column (prepacked in 2.5% methanol in dichloromethane contaning 1% triethylamine) was eluted with a solvent gradient from 2.5 to 5% methanol in dichloromethane, to provide the desired title compound.

General Procedure B

To a stirred solution of 10-(4-cyclohexyl-benzoyl)-10,11-dihydro-5H-pyrrolo[2,1 c][1,4]benzodiazepine-3-carboxylic acid of Example 22 (1.85 mmol) in anhydrous tetrahydrofuran (14 mL) was added 1,1'-carbonyldiimidazole (1.85 mmol) in one portion. The mixture was stirred at room temperature (6–8 hours). The progress of the reaction was monitored by HPLC and when the carboxylic acid was consumed an aliquot of the solution containing the imidazolide (0.05 mmol) was treated with a 0.25 M solution of the required amine in tetrahydrofuran (0.1 mmol). The mixture was heated at 60° C. and the progress of the reaction followed by HPLC. The solvent was removed and the residue dissolved in dichloromethane (1 mL). The organic phase was washed with brine-water (1:1, v/v, 1 mL) and the aqueous layer extracted with additional dichloromethane. The combined extracts were dried and evaporated to dryness and the residue purified as described in General Procedure A to provide the desired title compound.

General Procedure C

A stirred solution of 10-(4-cyclohexyl-benzoyl)-10,11-dihydro-5H-pyrrolo[2,1c][1,4]benzodiazepine-3-carboxylic acid of Example 22 (3.54 mmol) and the required amine (3.72 mmol) in N,N-dimethylformamide (10 mL) was cooled to 0° C. N,N-diisopropylethylamine (3.89 mmol) was added and the mixture stirred for five minutes. 1-Hydroxybenzotriazole tetramethyluronium hexafluorophosphate (HBTU) (1.42 g, 3.72 mmol) was added to the mixture in one portion. HPLC analysis revealed that the reaction was complete within five minutes. The solvent was removed at reduced pressure. The residue was diluted with water and extracted with ethyl acetate, The combined extracts were dried and concentrated to dryness. The residue was purified by flash chromatography on silica gel (prepacked in ethyl acetate containing 2% triethylamine and eluted with 100% ethyl acetate) to provide the desired title compound.

General Procedure D

To a stirred solution of 10-(4-cyclohexyl-benzoyl)-10,11-dihydro-5H-pyrrolo[2,1-c][1,4]benzodiazepine-3-carboxylic acid of Example 22 (2 mmol), 1-ethyl-3-(3-dimethylamino-propyl) carbodiimide (0.229 g, 2.2 mmol) and a catalytic amount of 4-(dimethylamino)pyridine in dichloromethane (6 mL) was added the required amine (2.2 mmol) in dichloromethane (2 mL). The reaction was allowed to stir at room temperature for 16 hours, then diluted with dichloromethane. The organic layer was washed with water and saturated aqueous sodium bicarbonate, dried over anhydrous sodium sulfate and evaporated to dryness. The residue was purified by flash chromatography on silica gel (prepacked in dichloromethane containing 2.5% methanol and 1% triethylamine and eluted with a solvent gradient of 2.5 to 5% methanol in dichloromethane) to provide the title compound.

EXAMPLE 33

10-(4-Cyclohexyl-benzoyl)-N-[3-(dimethylamino) propyl]-10,11-dihydro-5H-pyrrolo[2,1-c][1,4]benzodiazepine-3-carboxamide HRMS [(+)ESI, m/z]: 499.30603 [M+H]$^+$. Calcd. for $C_{31}H_{39}N_4O_2$: 499.30676.

EXAMPLE 34

10-(4-Cyclohexyl-benzoyl)-N-[2-(dimethylamino)-ethyl]-N-methyl-10,11-dihydro-5H-pyrrolo[2,1-c][1,4]benzodiazepine-3-carboxamide HRMS [(+)ESI, m/z]: 499.30614 [M+H]$^+$. Calcd. for $C_{31}H_{39}N_4O_2$: 499.30676

EXAMPLE 35

10-(4-Cyclohexyl-benzoyl)-N-[3-(dimethylamino) propyl]N-methyl-10,11-dihydro-5H-pyrrolo[2,1-c][1,4]benzodiazepine-3-carboxamide HRMS [(+)ESI, m/z]: 513.32179 [M+H]$^+$. Calcd. for $C_{32}H_{41}N_4O_2$: 513.32241

EXAMPLE 36

10-(4-Cyclohexyl-benzoyl)-N-[3-(1H-imidazol-1-yl) propyl]-10,11-dihydro-5H-pyrrolo[2,1-c][1,4]benzodiazepine-3-carboxamide HRMS [(+)ESI, m/z]: 522.28660 [M+H]$^+$. Calcd. for $C_{32}H_{36}N_5O_2$: 522.28636

EXAMPLE 37

10-(4-Cyclohexyl-benzoyl)-N-[2-(1-piperidinyl) ethyl]-10,11-dihydro-5H-pyrrolo[2,1-c][1,4]benzodiazepine-3-carboxamide HRMS [(+)ESI, m/z]: 525.32280 [M+H]$^+$. Calcd. for $C_{33}H_{41}N_4O_2$: 525.32241

EXAMPLE 38

10-(4-Cyclohexyl-benzoyl)-N-[2-(1-methyl-2-pyrrolidinyl)ethyl]-10,11-dihydro-5H-pyrrolo[2,1-c][1,4]benzodiazepine-3-carboxamide HRMS [(+)ESI, m/z]: 525.32274 [M+H]$^+$. Calcd. for $C_{33}H_{41}N_4O_2$: 525.32241

EXAMPLE 39

10-(4-Cyclohexyl-benzoyl)-N-methyl-N-(1-methyl-4-piperidinyl)-10,11-dihydro-5H-pyrrolo[2,1-c][1,4]benzodiazepine-3-carboxamide HRMS [(+)ESI, m/z]: 525.32312 [M+H]$^+$. Calcd. for $C_{33}H_{39}N_4O_2$: 525.32241

EXAMPLE 40

10-(4-Cyclohexyl-benzoyl)-N-methyl-N-(1-methyl-3-pyrrolidinyl)-10,11-dihydro-5H-pyrrolo[2,1-c][1,4]benzodiazepine-3-carboxamide MS [(+)ESI, m/z]: 511.30732 [M+H]$^+$. Calcd. for $C_{32}H_{39}N_4O_2$: 511.30676.

EXAMPLE 41

[10-(4-Cyclohexyl-benzoyl)-10,11-dihydro-5H-pyrrolo[2,1-c][1,4]benzodiazepin-3-yl]{4-[2-(dimethylamino)ethyl]-1-piperazinyl}methanone HRMS [(+)ESI, m/z]: 554.34902 [M+H]$^+$. Calcd. for $C_{34}H_{44}N_5O_2$: 554.34896

EXAMPLE 42

[10(4-Cyclohexyl-benzoyl)-10,11-dihydro-5H-pyrrolo[2,1-c][1,4]benzodiazepin-3-yl]{4-[2-(4-morpholinyl)ethyl]-1-piperazinyl}methanone HRMS [(+)ESI, m/z]: 596.36024 M+H]$^+$. Calcd. for $C_{36}H_{46}N_5O_3$: 596.35952

EXAMPLE 43

(4-Allyl-1-piperazinyl)[10-(4-cyclohexyl-benzoyl)-10,11-dihydro-5H-pyrrolo[2,1-c][1,4]benzodiazepin-3-yl]methanone HRMS [(+)ESI, m/z]: 523.30711 [M+H]$^+$. Calcd. for $C_{33}H_{39}N_4O_2$: 523.30676.

EXAMPLE 44

[10-(4-Cyclohexyl-benzoyl)-10,11-dihydro-5H-pyrrolo[2,1-c][1,4]benzodiazepin-3-yl](4-isopropyl-1-piperazinyl)methanone HRMS [(+)ESI, m/z]: 525.32244 [M+H]$^+$. Calcd. for $C_{33}H_{41}N_4O_2$: 525.32241.

EXAMPLE 45

[10-(4-Cyclohexyl-benzoyl)-10,11-dihydro-5H-pyrrolo[2,1-c][1,4]benzodiazepin-3-yl]{4-[3-(dimethylamino)propyl]-1-piperazinyl}methanone HRMS [(+)ESI, m/z]: 568.36487 [M+H]$^+$. Calcd. for $C_{35}H_{46}N_5O_2$: 568.36461.

EXAMPLE 46

[10-(4-Cyclohexyl-benzoyl)-10,11-dihydro-5H-pyrrolo[2,1-c][1.4]benzodiazepin-3-yl][(2S)-2-(1-pyrrolidinylmethyl)pyrrolidinyl]methanone HRMS [(+)ESI, m/z]: 551.33859 [M+H]$^+$. Calcd. for $C_{35}H_{43}N_4O_2$: 551.33806.

EXAMPLE 47

[10-(4-Cyclohexyl-benzoyl)-10,11-dihydro-5H-pyrrolo[2,1-C][1,4]benzodiazepin-3-yl][(3R)-3-(dimethylamino)pyrrolidinyl]methanone HRMS [(+)ESI, m/z]: 511.30682 [M+H]$^+$. Calcd. for $C_{32}H_{39}N_4O_2$: 511.30676.

EXAMPLE 48

[10-(4-Cyclohexyl-benzoyl)-10,11-dihydro-5H-pyrrolo[2,1-c][1,4]benzodiazepin-3-y][4-(2-hydroxyethyl)-1-piperazinyl]methanone HRMS [(+)ESI, m/z]: 527.30100 [M+H]$^+$.Calcd. for $C_{32}H_{39}N_4O_3$: 527.30167.

EXAMPLE 49

10-(4-Cyclohexyl-benzoyl)-N-[2-(2-pyridinyl)ethyl]-10,11-dihydro-5H-pyrrolo[2,1-c][1,4]benzodiazepine-3-carboxamide HRMS [(+)EI, m/z]: 519.27489 [M+H]$^+$.??? Calcd. for $C_{33}H_{35}N_4O_2$: 519.27546

EXAMPLE 50

10-(4-Cyclohexyl-benzoyl)-N-(2-pyridinylmethyl)-10,11-dihydro-5H-pyrrolo[2,1-c][1,4]benzodiazepine-3-carboxamide HRMS [(+)ESI, m/z]: 505.25935 [M+H]$^+$. Calcd. for $C_{32}H_{33}N_4O_2$: 505.25981

EXAMPLE 51

10-(4-Cyclohexyl-benzoyl)-N-(3-pyridinylmethyl)-10,11-dihydro-5H-pyrrolo [2,1-c][1,4]benzodiazepine-3-carboxamide HRMS [(+)ESI, m/z]: 505.25926 [M+H]+. Calcd. for $C_{32}H_{33}N_4O_2$: 505.25981

EXAMPLE 52

10-(4-Cyclohexyl-benzoyl)-N-methyl-N-[2-(2-pyridinyl)-ethyl]-10,11-dihydro-5H-pyrrolo[2,1-c][1,4]benzodiazepine-3-carboxamide HRMS [(+)ESI, m/z]: 533.29146 [M+H]$^+$. Calcd. for $C_{34}H_{36}N_4O_2$: 533.29111.

EXAMPLE 53

10-(4-Cyclohexyl-benzoyl)-N-(4-pyridinylmethyl)-10,11-dihydro-5H-pyrrolo[2,1-c][1,4]benzodiazepine-3-carboxamide HRMS [(+)ESI, m/z]: 505.26061 [M+H]$^+$. Calcd. for $C_{32}H_{33}N_4O_2$: 505.25981.

EXAMPLE 54

[10-(4-Cyclohexyl-benzoyl)-10,11-dihydro-5H-pyrrolo[2,1-c][1,4]benzpdiazepin-3-yl][4-(4-pyridinyl)-1-piperazinyl]-methanone HRMS [(+)ESI, m/z]: 560.30298 [M+H]$^+$. Calcd. for $C_{35}H_{38}N_5O_2$: 560.30201

EXAMPLE 55

10-(4-Cyclohexyl-benzoyl)-N-methyl-N-[2(4-pyridinyl)ethyl]-10,11-dihydro-5H-pyrrolo[2,1-c][1,4]benzodiazepine-3-carboxamide HRMS [(+)ESI, m/z]: 533.29142 [M+H]$^+$. Calcd. for $C_{34}H_{37}N_4O_2$: 533.29111

EXAMPLE 56

1H-Imidazol-1-yl-[10-(4-cyclohexyl-benzoyl)-10,11-dihydro-5H-pyrrolo[2,1-c][1,4]benzodiazepin-3-yl]-methanone HRMS [ESI(+), m/z]: 465.22831 [M+H]$^+$. Calcd. for $C_{29}H_{29}N_4O_2$: 465.22851

EXAMPLE 57

10-(4-Cyclohexyl-benzoyl)-N-methyl-N-(3-pyridinylmethyl)-10,11-dihydro-5H-pyrrolo[2,1-c][1,4]benzodiazepine-3-carboxamide HRMS [EI, m/z]: 519.27559 [M]$^+$. Calcd. for $C_{33}H_{34}N_4O_2$: 519.27546

What is claimed is:

1. A compound of the general formula (I):

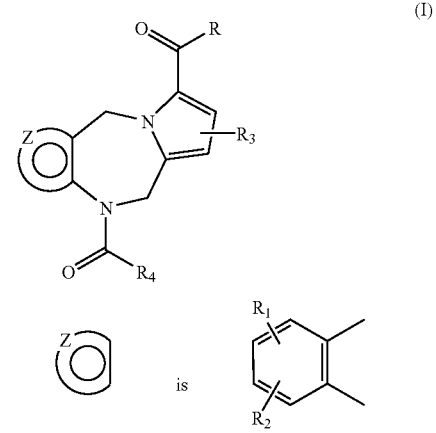

wherein: 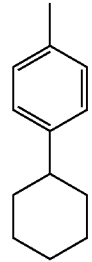 is $R_1$ and $R_2$ are, independently, hydrogen, ($C_1$–$C_6$)lower alkyl, halogen, cyano, trifluoromethyl, hydroxy, amino, ($C_1$–$C_6$) lower alkylamino, ($C_1$–$C_6$) lower alkoxy, ($C_1$–$C_6$) lower alkoxycarbonyl, carboxy, —$CONH_2$, —CONH ($C_1$–$C_6$) lower alkyl, or —CON[($C_1$–$C_6$) lower alkyl]$_2$;

$R_3$ is hydrogen, ($C_1$–$C_6$) lower alkyl, ($C_1$–$C_6$) lower alkoxy, hydroxy, amino, ($C_1$–$C_6$) lower alkylamino, —CO lower alkyl ($C_1$–$C_6$), or halogen;

$R_4$ consists of the moiety:

and R is selected from the group consisting of ($C_1$–$C_6$) lower alkyl, —$CCl_3$, —$CF_3$, hydroxy, —O[($C_1$–$C_6$) lower alkyl], aryl (optionally substituted with one to three substituents selected from the group consisting of ($C_1$–$C_6$) lower alkyl and halogen), —$NHOR_{31}$, —CH=CH—$N[R_{32}]_2$, and any of the following groups:

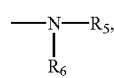   a

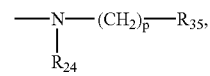   b

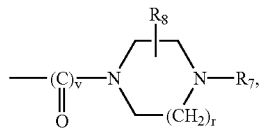   c

-continued

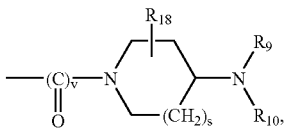  d

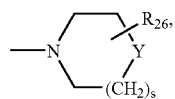  e

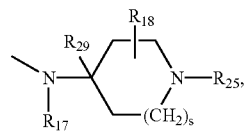  f

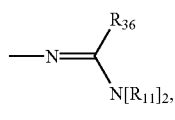  g

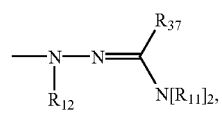  h

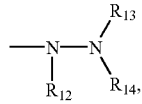  i

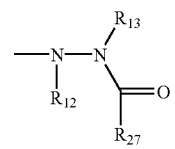  j wherein:
$R_5$ and $R_6$ are independently, hydrogen, $(C_1-C_6)$ lower alkyl, $(C_3-C_6)$ lower alkenyl, $(C_3-C_8)$ cycloalkyl optionally mono- or di-(lower alkyl) substituted, bicycloalkyl selected from the group consisting of adamantanyl, adamantane lower alkyl, bornyl, norbornyl, or quinuclidyl;

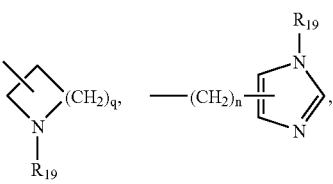

-continued

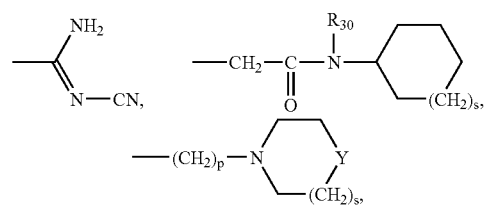

cycloalkyl lower alkyl, halo lower alkyl, cyano lower alkyl, lower alkyl thiol, alkoxycarbonyl lower alkyl, alkylthio lower alkyl, indolyl lower alkyl; aryl, optionally substituted with one to three substituents selected independently, from lower alkyl, hydroxy, lower alkoxy, aryl lower alkoxy, halogen, —$CF_3$, —$OCF_3$, —$OCF_2H$, —$OCH_2F$, —$OCH_2CF_3$, —$OCF_2CF_3$, —$OCH_2CHF_2$, alkylamido lower alkyl, dialkylamido lower alkyl, morpholinyl, thiomorpholinyl, pyrrolidinyl, piperidinyl, —$SCF_3$, —$SO_2$[lower alkyl], sulfonyl cycloalkyl,

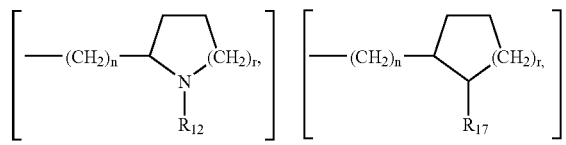  or  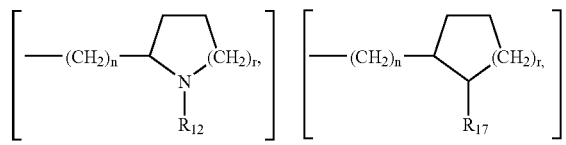  or $(C_7-C_{12})$ aryl lower alkyl, wherein the aryl moiety is optionally substituted with halogen or alkoxy; with the proviso that $R_5$ and $R_6$ can be taken together with the nitrogen to which they are attached to form a 5-membered unsaturated heteroaromatic ring containing 2 nitrogen atoms, the other ring atoms being carbon atoms;

$R_7$ is hydrogen, $(C_1-C_6)$ lower alkyl, $(C_3-C_6)$ lower alkenyl, $(C_3-C_6)$ lower alkynyl, $(C_3-C_8)$ cycloalkyl, —$CONH_2$, —$CON$[lower alkyl]$_2$, carbonyl lower alkyl, lower alkyl $CONH$[lower alkyl], lower alkyl $CON$[lower alkyl]$_2$, cycloalkylamino carbonyl, cycloalkylamino carbonyl lower alkyl, arylamino carbonyl lower alkyl, lower alkoxy carbonyl, lower alkoxy carbonyl lower alkyl, —$(CH_2)_p$—$N$[lower alkyl]$_2$, —$(CH_2)_p$—$N$[lower alkenyl]$_2$, —$CH$[aryl]$_2$ wherein the aryl is optionally substituted by $(C_1-C_6)$ lower alkyl or halogen;

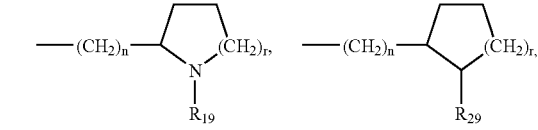

benzodioxolyl, benzodioxolyl lower alkyl, benzodioxanyl, benzodioxanyl lower alkyl, pyridyl, pyrimidinyl, pyridazinyl, furancarbonyl, —$SO_2$[lower alkyl], aryl optionally substituted by one to three substituents selected independently, from hydrogen, halogen, lower alkyl, lower alkenyl, lower alkynyl, lower alkoxy, —$CF_3$, —$OCF_3$, —$OCF_2H$, —$OCH_2F$, —$OCH_2CF_3$, —$OCF_2CF_3$, —$OCH_2CHF_2$, —$CO$ lower alkyl, —$CN$, nitro, —$SCH_3$, aryl lower alkoxy, aryl lower alkoxy carbonyl, indolyl, morpholino or thiomorpholino; or $(C_7-C_{12})$ lower aralkyl wherein the aryl moiety is optionally substituted with halogen, or lower alkoxy; or is a substituent selected from $$-\underset{R_{34}}{\overset{R_{33}}{(C)_p}}-R_{20}, \quad -CH_2-\underset{R_{20}}{CH}-R_{21}, \quad -CH_2-\underset{R_{20}}{CH}-R_{22},$$

$$-\underset{R_{34}}{\overset{R_{33}}{(C)_p}}-O-\underset{R_{34}}{\overset{R_{33}}{(C)_p}}-R_{20}$$

or a substituent selected from the group of

[pyridine structure with $R_{33}$, $R_{23}$, $(C)_t$, $R_{34}$, $(O)_v$];

$R_8$ represents one to three substituents selected, independently, from hydrogen or $(C_1-C_6)$ lower alkyl;

$R_9$ and $R_{10}$ are, independently, hydrogen or $(C_1-C_6)$ lower alkyl, with the proviso that $R_9$ and $R_{10}$ taken together with the nitrogen to which they are attached may form a 5-membered saturated heterocycle having 4 carbon ring atoms; or 6-membered saturated heterocycle optionally containing one additional O, S, or N[lower alkyl], the other ring atoms being carbon atoms;

$R_{11}$ is $(C_1-C_6)$ lower alkyl;

$R_{12}$ is hydrogen, or $(C_1-C_6)$ lower alkyl;

$R_{13}$ and $R_{14}$ are, independently, hydrogen, $(C_1-C_6)$ lower alkyl, or $(C_7-C_{11})$ aryl lower alkyl;

$R_{15}$ and $R_{16}$ are, independently, hydrogen, $(C_1-C_6)$ lower alkyl, or $(C_7-C_{12})$ aryl lower alkyl, with the proviso that $R_{15}$ and $R_{16}$ can be taken together with the nitrogen atom to which they are attached to form a 5 to 7 membered saturated heterocycle, optionally containing one additional O or S atom, the other ring atoms being carbon atoms (all of the above rings being optionally substituted with 1 or more alkyl groups); or a 5-membered unsaturated heterocycle containing 1 to 3 nitrogen atoms, the other ring atoms being carbon atoms;

$R_{17}$ is hydrogen, $(C_1-C_6)$ lower alkyl, or $(C_7-C_{12})$ aryl lower alkyl;

$R_{18}$ represents one to three substituents selected, independently, from hydrogen, $(C_1-C_6)$ lower alkyl, or $(C_7-C_{12})$ aryl lower alkyl;

$R_{19}$ is hydrogen, $(C_1-C_6)$ lower alkyl, or $(C_7-C_{12})$ aryl lower alkyl;

$R_{20}$ is hydroxy, lower alkoxy, or OP wherein P is a hydroxy protecting group;

$R_{21}$ is hydroxy lower alkyl, lower alkoxy lower alkyl, or lower alkyl OP wherein P is a hydroxy protecting group;

$R_{22}$ is $(C_1-C_6)$ lower alkyl, or $(C_7-C_{12})$ aryl lower alkyl;

$R_{23}$ represents one or two substituents selected, independently, from the group consisting of hydrogen, $(C_1-C_6)$ lower alkyl, halogen, trifluoromethyl, $(C_1-C_6)$ lower alkoxy, and $$-CH_2-N\underset{}{\diagdown}(CH_2)_r;$$

$R_{24}$ is hydrogen, $(C_1-C_6)$ lower alkyl, $(C_1-C_{12})$ aryl lower alkyl, or $-(CH_2)_p-N$ (lower alkyl)$_2$;

$R_{25}$ is $(C_1-C_6)$ lower alkyl, $(C_7-C_{12})$ aryl lower alkyl, lower alkoxy carbonyl, or SO$_2$[lower alkyl];

$R_{26}$ is hydrogen, $(C_1-C_6)$ lower alkyl, —N[lower alkyl]$_2$, cycloalkylamino lower alkyl or

[pyridine structure with $R_{23}$, $(O)_v$];

when Y=CH$_2$; or is selected from the group of hydrogen and $(C_1-C_6)$ lower alkyl when Y=X;

$R_{27}$ is either $R_{28}$, or —NHR$_{38}$;

$R_{28}$ is $(C_1-C_6)$ lower alkyl, $(C_3-C_8)$ cycloalkyl, or aryl optionally substituted by one to three substituents chosen from the group of halogen or $(C_1-C_6)$ lower alkyl;

$R_{29}$ is hydrogen, or $(C_1-C_6)$ lower alkyl;

$R_{30}$ is hydrogen, $(C_1-C_6)$ lower alkyl, or $(C_7-C_{12})$ aryl lower alkyl;

$R_{31}$ is hydrogen or $(C_1-C_6)$ lower alkyl;

$R_{32}$ is $(C_1-C_6)$ lower alkyl;

$R_{33}$ and $R_{34}$ are, independently, hydrogen, $(C_1-C_6)$ lower alkyl, or $(C_7-C_{12})$ aryl lower alkyl;

$R_{35}$ is:

$$-\underset{}{\overset{R_{15}}{N}}-R_{16}, \quad -\underset{R_{34}}{\overset{R_{33}}{(C)_p}}-R_{20} \quad \text{or} \quad -CH_2-\underset{R_{20}}{CH}-R_{21};$$

$R_{36}$ and $R_{37}$ are hydrogen or $(C_1-C_6)$ lower alkyl;

$R_{38}$ is $(C_1-C_6)$ lower alkyl, $(C_3-C_8)$ cycloalkyl; or aryl, optionally substituted by one to three substituents chosen from the group of halogen, or $(C_1-C_6)$ lower alkyl;

X is O, S, SO, SO$_2$, or N[lower alkyl];

Y is CH$_2$, or X;

n is an integer from 1 to 4;

p is an integer from 2 to 4;

q is an integer from 1 to 5;

r is an integer from 1 to 2;

s is an integer from 0 to 1;

t is an integer from 0 to 2; and v is an integer from 0 to 1;

or a pharmaceutically acceptable salt form thereof.

2. A compound of the formula:

[Structure: tricyclic pyrrolo-benzodiazepine bearing C(O)R at one position, R$_1$ and R$_2$ on the benzene ring, R$_3$ on the pyrrole ring, and an N-C(O)-phenyl-cyclohexyl group]

R$_1$ and R$_2$ are, independently, hydrogen, C$_1$–C$_6$ alkyl, halogen, cyano, trifluoromethyl, hydroxy, amino, (C$_1$–C$_6$) alkylamino, C$_1$–C$_6$ alkoxy, —C(O)O—(C$_1$–C$_6$ alkyl), carboxy, —CONH$_2$, —CONH (C$_1$–C$_6$) lower alkyl, or —CON[(C$_1$–C$_6$) lower alkyl]$_2$;

R$_3$ is hydrogen, (C$_1$–C$_6$) lower alkyl, (C$_1$–C$_6$) lower alkoxy, hydroxy, amino (C$_1$–C$_6$) lower alkylamino, —CO lower alkyl (C$_1$–C$_6$), or halogen;

R is selected from lower alkyl, —NHNH$_2$, —NHOR$_{31}$; —CH=CH—N[R$_{32}$]$_2$; lower alkoxy; phenyl optionally substituted by from one to three substituents selected from (C$_1$–C$_6$) lower alkyl or halogen; or a moiety of the formulae:

a  —N(R$_5$)R$_6$ b  —N(R$_{24}$)—(CH$_2$)$_p$—R$_{35}$ c  —(C)$_v$(=O)—N[CH$_2$CH$_2$]N—R$_7$, with R$_8$ substituent and (CH$_2$)$_r$ d  —(C)$_v$(=O)—N[piperidine with R$_{18}$]—CH(R$_9$)(R$_{10}$) with (CH$_2$)$_s$ e  —N[CH$_2$CH$_2$]Y(R$_{26}$)(CH$_2$)$_s$ f  —N(R$_{17}$)—C(R$_{29}$)—[piperidine with R$_{18}$]—N—R$_{25}$ with (CH$_2$)$_s$ g  —N=C(R$_{36}$)N[R$_{11}$]$_2$ h  —N(R$_{12}$)—N=C(R$_{37}$)N[R$_{11}$]$_2$, i  —N(R$_{12}$)—N(R$_{13}$)(R$_{14}$), j  —N(R$_{12}$)—N(R$_{13}$)—C(=O)—R$_{27}$ R$_5$ and R$_6$ are independently, selected from the group consisting of hydrogen, lower alkyl, (C$_3$–C$_6$) lower alkenyl, (C$_3$–C$_8$) cycloalkyl optionally mono- or di-(C$_1$–C$_6$) lower alkyl substituted; and phenyl, optionally substituted with one to three substituents selected independently, from the group consisting of lower alkyl, hydroxy, lower alkoxy, aryl lower alkoxy, halogen, —CF$_3$, —OCF$_3$, —OCF$_2$H, —OCH$_2$F, —OCH$_2$CF$_3$, —OCF$_2$CF$_3$, —OCH$_2$CHF$_2$, alkylamido lower alkyl, and dialkylamido lower alkyl; or R$_5$ and R$_6$ can be taken together with the nitrogen to which they are attached to form a 5-membered unsaturated heteroaromatic ring containing 2 nitrogen atoms, the other ring atoms being carbon atoms;

R$_7$ is hydrogen, (C$_1$–C$_6$) lower alkyl, (C$_3$–C$_6$) lower alkenyl, (C$_3$–C$_6$) lower alkynyl, (C$_3$–C$_8$) cycloalkyl, —CONH$_2$, —CON[lower alkyl]$_2$, carbonyl lower alkyl, lower alkyl CONH[lower alkyl], lower alkyl CON[lower alkyl]$_2$, or cycloalkylamino carbonyl; or R$_7$ is —CH[aryl]$_2$ wherein the aryl is phenyl optionally substituted by (C$_1$–C$_6$) lower alkyl, lower alkoxy, or halogen; or R$_7$ is a pyridine or pyrimidine moiety; or R$_7$ is a moiety selected from the group consisting of:

—(CH$_2$)$_p$—N(alkyl)$_2$,  —(CH$_2$)$_p$—N[morpholine]O,  or
—(CH$_2$)$_p$—OH;

R$_8$ represents one to three substituents selected, independently, from H or C$_1$–C$_6$ alkyl;

R$_9$ and R$_{10}$ are, independently, hydrogen or (C$_1$–C$_6$) lower alkyl, with the proviso that R$_9$ and R$_{10}$ taken together with the nitrogen to which they are attached may form a 5-membered saturated heterocycle having 4 carbon ring atoms; or a 6-membered saturated heterocycle optionally containing one additional O, S, or N[lower alkyl], the other ring atoms being carbon atoms;

R$_{11}$ is (C$_1$–C$_6$) lower alkyl;

R$_{12}$ is hydrogen, or (C$_1$–C$_6$) lower alkyl;

R$_{13}$ and R$_{14}$ are, independently hydrogen, or (C$_1$–C$_6$) alkyl;

R$_{15}$ and R$_{16}$ are, independently, hydrogen, or (C$_1$–C$_6$) lower alkyl, with the proviso that R$_{15}$ and R$_{16}$ can be taken together with the nitrogen atom to which they are attached to form either:

a) a 5 to 7 membered saturated heterocycle, optionally containing one additional O or S atom (all of the above rings being optionally substituted with from 1 to 3 $C_1$–$C_6$ alkyl groups), the other ring atoms being carbon atoms; or
b) a 5-membered unsaturated heterocycle containing 1 to 3 nitrogen atoms, the other ring atoms being carbon atoms;

$R_{17}$ is hydrogen or ($C_1$–$C_6$) lower alkyl;

$R_{18}$ represents one to three substituents selected, independently, from the group consisting of hydrogen, ($C_1$–$C_6$) lower alkyl, and ($C_7$–$C_{12}$) aryl lower alkyl;

$R_{24}$ is hydrogen, ($C_1$–$C_6$) lower alkyl, ($C_1$–$C_{12}$) aryl lower alkyl, or —$(CH_2)_p$—N (lower alkyl)$_2$;

$R_{25}$ is ($C_1$–$C_6$) alkyl;

$R_{26}$ is H, ($C_1$–$C_6$) alkyl, cycloalkylamino lower alkyl, or —N[lower alkyl]$_2$;

$R_{27}$ is either $R_{28}$, or —$NHR_{38}$;

$R_{28}$ is ($C_1$–$C_6$) alkyl, ($C_3$–$C_8$) cycloalkyl, or phenyl optionally substituted by 1 to 3 groups selected from halogen or ($C_1$–$C_6$) alkyl;

$R_{29}$ is hydrogen, or ($C_1$–$C_6$) lower alkyl;

$R_{31}$ is hydrogen or ($C_1$–$C_6$) lower alkyl;

$R_{32}$ is ($C_1$–$C_6$) lower alkyl;

$R_{35}$ is the moiety

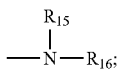

$R_{36}$ and $R_{37}$ are selected, from the group consisting of hydrogen and ($C_1$–$C_6$) lower alkyl;

$R_{38}$ is selected from the group consisting of ($C_1$–$C_6$) lower alkyl, ($C_3$–$C_8$) cycloalkyl; and aryl, optionally substituted by one to three substituents chosen from the group consisting of halogen and ($C_1$–$C_6$) lower alkyl;

Y is $CH_2$;

p is an integer from 2 to 4;

r is an integer from 1 to 2;

s is an integer from 0 to 1; and v is an integer from 0 to 1;

or a pharmaceutically acceptable salt form thereof.

3. A compound of the formula:

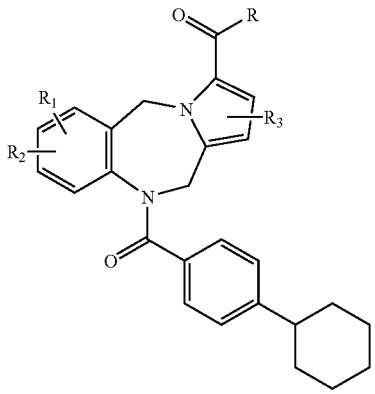

$R_1$ and $R_2$ are, independently, hydrogen, $C_1$–$C_6$ alkyl, halogen, cyano, trifluoromethyl, hydroxy, amino, $C_1$–$C_6$ alkylamino, $C_1$–$C_6$ alkoxy, —C(O)O—($C_1$–$C_6$ alkyl), carboxy, —$CONH_2$, —CONH—($C_1$–$C_6$ alkyl), or —CON[($C_1$–$C_6$) lower alkyl]$_2$;

$R_3$ is hydrogen, $C_1$–$C_6$ alkyl, $C_1$–$C_6$ alkoxy, OH, amino, $C_1$–$C_6$ alkylamino, —CO—($C_1$–$C_6$ alkyl), or halogen;

R is —$NHNH_2$, —$NHOR_{31}$; or —CH=CH—$N[R_{32}]_2$; —NH—NH—C(O)—($C_3$–$C_6$ cycloalkyl); —NHNH ($C_1$–$C_6$ alkyl) or —NHN($C_1$–$C_6$ alkyl)$_2$; or a) phenyl optionally substituted by from one to three substituents selected from ($C_1$–$C_6$) lower alkyl, —C(O)—($C_1$–$C_6$) alkyl, or halogen;

b) —NH-phenyl, —NH—NH—C(O)-phenyl or —NH—NH—C(O)—NH-phenyl, the phenyl rings of which are optionally substituted by from one to three substituents selected from $C_1$–$C_6$ alkyl, or halogen; or c) imidazolyl;

or a moiety of the formulae:

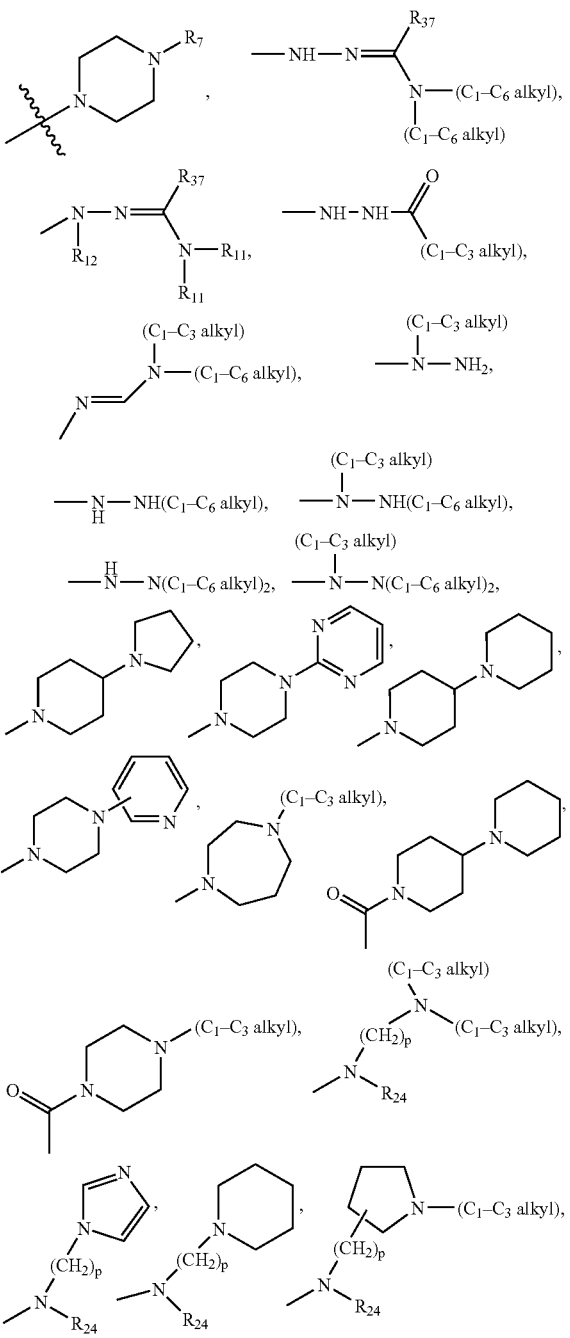

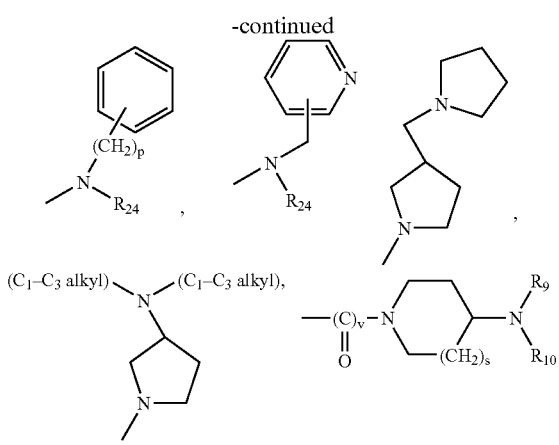

R₇ is hydrogen, $C_1$–$C_6$ alkyl, $C_3$–$C_6$ alkenyl, $C_3$–$C_6$ alkynyl, —$C_1$–$C_6$ alkyl-OH, —$(CH_2)_p$—$NH_2$, —$(CH_2)_p$—NH[lower alkyl], —$(CH_2)_p$—N[lower alkyl]$_2$, —$(CH_2)_p$-morpholino; or phenyl optionally substituted by from one to three substituents selected independently from the group consisting of H, halogen, $C_1$–$C_6$ alkyl, $C_3$–$C_6$ alkenyl, $C_3$–$C_6$ alkynyl, $C_3$–$C_6$ alkoxy, —$CF_3$, —$OCF_3$, —$OCF_2H$, —$OCH_2F$, —$OCH_2CF_3$, —$OCF_2CF_3$, —$OCH_2CHF_2$, —CO—$C_1$–$C_6$ alkyl, —CN, nitro, and —$SCH_3$;

R₉ and R₁₀ are, independently, hydrogen or ($C_1$–$C_6$) lower alkyl, with the proviso that R₉ and R₁₀ taken together with the nitrogen to which they are attached may form a 5-membered saturated heterocycle having 4 carbon ring atoms; or 6-membered saturated heterocycle optionally containing one additional O, S, or N[lower alkyl], the other ring atoms being carbon atoms;

R₁₁ is $C_1$–$C_6$ alkyl;
R₁₂ is H or $C_1$–$C_6$ alkyl;
R₂₄ is H or $C_1$–$C_3$ alkyl;
R₃₁ is hydrogen or ($C_1$–$C_6$) lower alkyl;
R₃₂ is ($C_1$–$C_6$) lower alkyl;
R₃₇ is independently H or $C_1$–$C_3$ alkyl;
p is an integer from 2 to 4;
s is an integer from 0 to 1; and
v is an integer from 0 to 1;
or a pharmaceutically acceptable salt form thereof.

4. A compound of claim 1 which is:
a) Methyl 10-(4-cyclohexylbenzoyl)-3-[(4-methyl-1-piperazinyl)carbonyl]-10,11-dihydro-5H-pyrrolo[2,1-c][1,4]benzodiazepine-8-carboxylate;
b) 10-(4-Cyclohexyl-benzoyl)-3-[(4-methyl-1-piperazinyl)carbonyl]-10,11-dihydro-5H-pyrrolo[2,1-c][1,4]benzodiazepine-8-carboxylic acid;
c) [4-(tert-Butyl)phenyl][10-(4-cyclohexyl-benzoyl)-10,11-dihydro-5H-pyrrolo[2,1-c][1,4]benzodiazepin-3-yl] methanone;
d) 1-[10-(4-Cyclohexyl-benzoyl)-10,11-dihydro-5H-pyrrolo[2,1-c][1,4]benzodiazepin-3-yl]-ethanone;
e) 2,2,2-Trichloro-1-[10-(4-cyclohexyl-benzoyl)-10,11-dihydro-5H-pyrrolo[2,1-c][1,4]benzodiazepin-3-yl]-1-ethanone;
f) 10-(4-Cyclohexyl-benzoyl)-10,11-dihydro-5H-pyrrolo[2,1-c][1,4]benzodiazepine-3-carboxylic acid hydrazide;
g) N'-{[10-(4-Cyclohexyl-benzoyl)-10,11-dihydro-5H-pyrrolo[2,1-c][1,4]benzodiazepin-3-yl]carbonyl}-N,N-dimethylethanehydrazonamide; or
h) N'-{[10-(4-Cyclohexyl-benzoyl)-10,11-dihydro-5H-pyrrolo[2,1-c][1,4]benzodiazepin-3-yl]carbonyl}-N,N-dimethylhydrazonoformamide;

or a pharmaceutically acceptable salt form thereof.

5. A compound of claim 1 which is:
a) N'-Acetyl-10-(4-cyclohexyl-benzoyl)-10,11-dihydro-5H-pyrrolo[2,1-c][1,4]benzodiazepine-3-carbonyl-hydrazide;
b) 10-(4-Cyclohexyl-benzoyl)-N'-(2-methylbenzoyl)-10,11-dihydro-5H-pyrrolo[2,1-c][1,4]benzodiazepine-3-carbonyl-hydrazide;
c) 10-(4-Cyclohexyl-benzoyl)-N'-(cyclopropylcarbonyl)-10,11-dihydro-5H-pyrrolo[2,1-c][1,4]benzodiazepine-3-carbonyl-hydrazide;
d) 10-(4-Cyclohexylbenzoyl)-N'-(3-methylbenzoyl)-10,11-dihydro-5H-pyrrolo[2,1-c][1,4]benzodiazepine-3-carbonyl-hydrazide;
e) 2-{[10-(4-Cyclohexyl-benzoyl)-10,11-dihydro-5H-pyrrolo[2,1-c][1,4]benzodiazepin-3-yl]carbonyl}-N-phenyl-1-hydrazinecarboxamide;
f) 10-(4-Cyclohexyl-benzoyl)-10,11-dihydro-5H-pyrrolo[2,1-c][1,4]benzodiazepin-3-carboxamide;
g) 10-(4-Cyclohexyl-benzoyl)-10,11-dihydro-5H-pyrrolo[2,1-c][1,4]benzodiazepine-3-carboxylic acid (1-dimethylamino-ethylidene)-amide;
h) 10-(4-Cyclohexyl-benzoyl)-10,11-dihydro-5H-pyrrolo[2,1-c][1,4]benzodiazepine-3-carboxylic acid (1-dimethylamino-ethylidene)-amide;
i) 10-(4-Cyclohexyl-benzoyl)-N'-N'-dimethyl-10,11-dihydro-5H-pyrrolo[2,1-c][1,4]benzodiazepine-3-carbohydrazide; or
j) (E)-1-[10-(4-Cyclohexyl-benzoyl)-10,11-dihydro-5H-pyrrolo[2,1-c][1,4]benzodiazepin-3-yl]-3-(dimethylamino)-2-propen-1-one;

or a pharmaceutically acceptable salt form thereof.

6. A compound of claim 1 which is:
a) 10-(4-Cyclohexyl-benzoyl)-N-methyl-10,11-dihydro-5H-pyrrolo[2,1-c][1,4]benzodiazepine-3-carbohydrazide;
b) 10-(4-Cyclohexyl-benzoyl)-10,11-dihydro-5H-pyrrolo[2,1c][1,4]benzodiazepine-3-carboxylic acid;
c) [10-(4-Cyclohexyl-benzoyl)-10,11-dihydro-5H-pyrrolo[2,1-c][1,4]benzodiazepin-3-yl][4-(2-pyrimidinyl)-1-piperazinyl]methanone;
d) [10-(4-Cyclohexyl-benzoyl)-10,11-dihydro-5H-pyrrolo[2,1-c][1,4]benzodiazepin-3-yl](4-methyl-1-piperazinyl)-methanone;
e) [10-(4-Cyclohexyl-benzoyl)-10,11-dihydro-5H-pyrrolo[2,1-c][1,4]benzodiazepin-3-yl][4-(1-pyrrolidinyl)-1-piperidinyl]methanone;
f) [1,4']Bipiperidinyl-1'-yl-[10-(4-cyclohexyl-benzoyl)-10,11-dihydro-5H-pyrrolo[2,1-c][1,4]benzodiazepin-3-yl]-methanone;
g) [10-(4-Cyclohexyl-benzoyl)-10,11-dihydro-5H-pyrrolo [2,1-c][1,4]benzodiazepin-3-yl][4-(2-methylphenyl)-1-piperazinyl]-methanone;
h) [10-(4-Cyclohexyl-benzoyl)-10,11-dihydro-5H-pyrrolo [2,1-c][1,4]benzodiazepine 3-yl][4-(2-pyridinyl)-1-piperazinyl]-methanone;
i) 10-(4-Cyclohexyl-benzoyl)-10,11-dihydro-5H-pyrrolo[2,1-c][1,4]benzaodiazepine-3-carboxylic acid (4-methoxy-phenyl)-amide; or
j) [10-(4-Cyclohexyl-benzoyl)-10,11-dihydro-5H-pyrrolo[2,1-c][1,4]benzodiazepin-3-yl](4-methyl-[1,4]-diazepan-1-yl)-methanone;

or a pharmaceutically acceptable salt form thereof.

7. A compound of claim 1 which is:
a) 1-[1,4']Bipiperidinyl-1'-yl-2-[10-(4-cyclohexyl-benzoyl)-10,11-dihydro-5H-pyrrolo[2,1-c][1,4]benzodiazepin-3-yl]-ethane-1,2-dione;
b) 1-[10-(4-Cyclohexyl-benzoyl)-10,11-dihydro-5H-pyrrolo[2,1-c][1,4]benzodiazepin-3-yl]-2-(4-methyl-1-piperazin-1-yl)-1,2-ethane-1,2-dione;
c) 10-(4-Cyclohexyl-benzoyl)-N-[3-(dimethylamino)propyl]-10,11-dihydro-5H-pyrrolo[2,1-c][1,4]benzodiazepine-3-carboxamide;
d) 10-(4-Cyclohexyl-benzoyl)-N-[2-(dimethylamino)-ethyl]-N-methyl-10,11-dihydro-5H-pyrrolo[2,1-c][1,4]benzodiazepine-3-carboxamide;
e) 10-(4-Cyclohexyl-benzoyl)-N-[3-(dimethylamino)propyl]N-methyl-10,11-dihydro-5H-pyrrolo[2,1-c][1,4]benzodiazepine-3-carboxamide;
f) 10-(4-Cyclohexyl-benzoyl)-N-[3-(1H-imidazol-1-yl)propyl]-10,11-dihydro-5H-pyrrolo[2,1-c][1,4]benzodiazepine-3-carboxamide;
g) 10-(4-Cyclohexyl-benzoyl)-N-[2-(1-piperidinyl)ethyl]-10,11-dihydro-5H-pyrrolo[2,1-c][1,4]benzodiazepine-3-carboxamide;
h) 10-(4-Cyclohexyl-benzoyl)-N-[2-(1-methyl-2-pyrrolidinyl)ethyl]-10,11-dihydro-5H-pyrrolo[2,1-c][1,4]benzodiazepine-3-carboxamide;
i) 10-(4-Cyclohexyl-benzoyl)-N-methyl-N-(1-methyl-4-piperidinyl)-10,11-dihydro-5H-pyrrolo[2,1-c][1,4]benzodiazepine-3-carboxamide; or
j) 10-(4-Cyclohexyl-benzoyl)-N-methyl-N-(1-methyl-3-pyrrolidinyl)-10,11-dihydro-5H-pyrrolo[2,1-c][1,4]benzodiazepine-3-carboxamide
or a pharmaceutically acceptable salt form thereof.

8. A compound of claim 1 which is:
a) [10-(4-Cyclohexyl-benzoyl)-10,11-dihydro-5H-pyrrolo[2,1-c][1,4]benzodiazepin-3-yl]{4-[2-(dimethylamino)ethyl]-1-piperazinyl}methanone;
b) [10-(4-Cyclohexyl-benzoyl)-10,11-dihydro-5H-pyrrolo[2,1-c][1,4]benzodiazepin-3-yl]{4-[2-(4-morpholinyl)ethyl]-1-piperazinyl}methanone;
c) (4-Allyl-1-piperazinyl)[10-(4-cyclohexyl-benzoyl)-10,11-dihydro-5H-pyrrolo[2,1-c][1,4]benzodiazepin-3-yl]methanone;
d) [10-(4-Cyclohexyl-benzoyl)-10,11-dihydro-5H-pyrrolo[2,1-c][1,4]benzodiazepin-3-yl](4-isopropyl-1-piperazinyl)methanone;
e) [10-(4-Cyclohexyl-benzoyl)-10,11-dihydro-5H-pyrrolo[2,1-c][1,4]benzodiazepin-3-yl]{4-[3-(dimethylamino)propyl]-1-piperazinyl}methanone;
f) [10-(4-Cyclohexyl-benzoyl)-10,11-dihydro-5H-pyrrolo[2,1-c][1,4]benzodiazepin-3-yl][(3R)-3-(dimethylamino)pyrrolidinyl]methanone;
g) [10-(4-Cyclohexyl-benzoyl)-10,11-dihydro-5H-pyrrolo[2,1-c][1,4]benzodiazepin-3-yl][4-(2-hydroxyethyl)-1-piperazinyl]methanone;
h) 10-(4-Cyclohexyl-benzoyl)-N-[2-(2-pyridinyl)ethyl]-10,11-dihydro-5H-pyrrolo[2,1-c][1,4]benzodiazepine-3-carboxamide or
i) 10-(4-Cyclohexyl-benzoyl)-N-(2-pyridinylmethyl)-10,11-dihydro-5H-pyrrolo[2,1-c][1,4]benzodiazepine-3-carboxamide;
or a pharmaceutically acceptable salt form thereof.

9. A compound of claim 1 which is:
a) 10-(4-Cyclohexyl-benzoyl)-N-(3-pyridinylmethyl)-10,11-dihydro-5H-pyrrolo[2,1-c][1,4]benzodiazepine-3-carboxamide;
b) 10-(4-Cyclohexylbenzoyl)-N-methyl-N-[2-(2-pyridinyl)-ethyl]-10,11-dihydro-5H-pyrrolo[2,1-c][1,4]benzodiazepine-3-carboxamide;
c) 10-(4-Cyclohexyl-benzoyl)-N-(4-pyridinylmethyl)-10,11-dihydro-5H-pyrrolo[2,1-c][1,4]benzodiazepine-3-carboxamide;
d) [10-(4-Cyclohexyl-benzoyl)-10,11-dihydro-5H-pyrrolo[2,1-c][1,4]benzpdiazepin-3-yl][4-(4-pyridinyl)-1-piperazinyl]-methanone;
e) 10-(4-Cyclohexyl-benzoyl)-N-methyl-N-[2(4-pyridinyl)ethyl]-10,11-dihydro-5H-pyrrolo[2,1-c][1,4]benzodiazepine-3-carboxamide;
f) 1H-Imidazol-1-yl-[10-(4-cyclohexyl-benzoyl)-10,11-dihydro-5H-pyrrolo[2,1-c][1,4]benzodiazepin-3-yl]-methanone; or
g) 10-(4-Cyclohexyl-benzoyl)-N-methyl-N-(3-pyridinylmethyl)-10,11-dihydro-5H-pyrrolo[2,1-c][1,4]benzodiazepine-3-carboxamide;
or a pharmaceutically acceptable salt form thereof.

10. A pharmaceutical composition comprising a pharmaceutically effective amount of a compound of claim 1 and a pharmaceutically acceptable carrier of excipient.

11. A method of suppressing preterm labor or for suppressing labor prior to caesarean delivery in a mammal, the method comprising administering to the mammal in need thereof a pharmaceutically effective amount of a compound of claim 1.

12. A method of treating dysmenorrhea or endometritis in a mammal, the method comprising administering to the mammal in need thereof a pharmaceutically effective amount of a compound of claim 1.

13. A pharmaceutical composition comprising a pharmaceutically effective amount of a compound of claim 3 and a pharmaceutically acceptable carrier or excipient.

14. A method of suppressing preterm labor or for suppressing labor prior to caesarean delivery in a mammal, the method comprising administering to the mammal in need thereof a pharmaceutically effective amount of a compound of claim 3.

15. A method of treating dysmenorrhea or endometritis in a mammal, the method comprising administering to the mammal in need thereof a pharmaceutically effective amount of a compound of claim 3.

16. A pharmaceutical composition comprising a compound of claim 2 and a pharmaceutically acceptable carrier or excipient.

17. A method of suppressing preterm labor or for suppressing labor prior to caesarean delivery in a mammal, the method comprising administering to the mammal in need thereof an effective amount of a compound of claim 2.

18. A method of treating dysmenorrhea or endometritis in a mammal, the method comprising administering to the mammal in need thereof an effective amount of a compound of claim 2.

19. A compound of claim 3 that is [10-(4-Cyclohexyl-benxoyl)-10,11-dihydro-5H-pyrrolo[2,1-c][1,4]benzodiazepin-3-yl][(2S)-2-(1-pyrrolidinylmethyl) pyrrolidinyl]methanone or a pharmaceutically acceptable salt form thereof.

20. A pharmaceutical composition comprising a compound of claim 19 and a pharmaceutically acceptable carrier or excipient.

21. A method for suppressing preterm labor in mammal, suppressing labor prior to caesarean delivery in a mammal, treating dysmenorrhea in a mammal, or treating endometritis in a mammal, the method comprising administering to the mammal in need thereof an effective amount of a compound of claim 19.

* * * * *